US007754718B2

(12) United States Patent
Yeo et al.

(10) Patent No.: US 7,754,718 B2

(45) Date of Patent: Jul. 13, 2010

(54) ANTIVIRAL HELIOXANTHIN ANALOGS

(75) Inventors: Hosup Yeo, Daegu (KR); David J. Austin, New York, NY (US); Ling Li, Bellaire, TX (US); Yung-chi Cheng, Woodbridge, CT (US)

(73) Assignee: Yale University, New Haven, CT (US)

( * ) Notice: Subject to any disclaimer, the term of this patent is extended or adjusted under 35 U.S.C. 154(b) by 178 days.

(21) Appl. No.: 11/579,284

(22) PCT Filed: May 2, 2005

(86) PCT No.: PCT/US2005/014698

§ 371 (c)(1), (2), (4) Date: Sep. 18, 2007

(87) PCT Pub. No.: WO2005/107742

PCT Pub. Date: Nov. 17, 2005

(65) Prior Publication Data

US 2008/0167353 A1 Jul. 10, 2008

Related U.S. Application Data

(60) Provisional application No. 60/568,348, filed on May 5, 2004.

(51) Int. Cl.
*A61K 31/502* (2006.01)
*C07D 237/26* (2006.01)

(52) U.S. Cl. ...................................... 514/248; 544/233

(58) Field of Classification Search ................. 514/463, 514/248, 410; 549/433, 235, 298, 432; 544/233; 548/421
See application file for complete search history.

(56) References Cited

U.S. PATENT DOCUMENTS 4,840,951 A * 6/1989 Iwasaki et al. ........... 514/239.5
4,957,924 A 9/1990 Beauchamp
4,999,428 A 3/1991 Saksena et al.
5,003,087 A * 3/1991 Iwasaki et al. .............. 549/299
5,015,739 A 5/1991 Saksena et al.
5,142,051 A 8/1992 Holy et al.
5,372,808 A 12/1994 Blatt et al.
5,641,763 A 6/1997 Holy et al.
5,676,942 A 10/1997 Testa et al.
5,684,010 A 11/1997 Schinazi
5,726,174 A 3/1998 Kim et al.
5,738,845 A 4/1998 Imakawa
5,777,116 A 7/1998 Onishi et al.
5,817,638 A 10/1998 Hostetler
5,821,242 A 10/1998 Colacino et al.
5,830,455 A 11/1998 Valtuena et al.
5,830,881 A 11/1998 Lin et al.
5,837,871 A 11/1998 Kim et al.
5,849,696 A 12/1998 Chretien et al.
5,869,467 A 2/1999 Holy et al.
5,891,874 A 4/1999 Colacino et al.
5,908,621 A 6/1999 Glue et al.
5,928,636 A 7/1999 Alber et al.
5,929,038 A 7/1999 Chang
5,942,223 A 8/1999 Bazer et al.
5,980,884 A 11/1999 Blatt et al.
6,030,967 A 2/2000 Marui et al.
6,306,899 B1 10/2001 Cheng et al.
6,323,180 B1 11/2001 Linas-Brunet et al.
2004/0033959 A1 2/2004 Chen et al.

FOREIGN PATENT DOCUMENTS

WO WO00/10991 3/2000
WO WO 01/32153 5/2001
WO WO 01/60315 8/2001
WO WO 01/96353 12/2001
WO WO 02/18404 3/2002
WO WO 02/057287 7/2002
WO WO 02/057425 7/2002

OTHER PUBLICATIONS

Vippagunta et al., Crystalline solids, 2001, Advanced Drug Delivery Reviews, 48, pp. 3 and 18.*
Seeger, C., et al., 2000, Microbiol Mol Biol Rev. 64(1):51-68.
Tiollais et al., 1985, Nature 317 (6037):489-495.
De Clercq, 1999, Int J Antimicrob Agents. 12(2):81-95.
Summers et al., 1982, Cell 29(2):403-415.
Weimer et al., 1987, J Virol. 61 (10):3109-3113.
Fu et al., 2000, Antimicrob Agents Chemother. 44:3402-3407.
Chang et al., 1992. J. Biol. Chem. 267:13938-13942.
Dong et al. 1991, Proc. Natl. Acad. Sci. U.S.A. 88:8495-8499.
Angus et al., 2003, Gastroenterology 125:292-297.
Fu et al., 1999, Biochem Pharmacol. 57(12):1351-1359.
Leung et al., 2001, Hepatology 33(6):1527-1532.
Liaw et al., 2000, Gastroenterology 119(1):172-180.
Liaw et al., 2003, J Gastroenterol Hepatol. 18:239-245.
Mutimer, 2001, J. Clin. Virol. 21:239-242.
Levine et al., 2002, Antimicrob. Agents Chemother. 46:2525-2532.
McCaffrey et al., 2003, Nature Biotechnol. 21(6):639-644.
Shlomai et al., 2003, Hepatology 37(4):764-770.
Morrisey et al., 2002, J Viral Hepat. 9(6):411-418.
Kwon et al., 2002, Biochem Cell Biol. 80(4):445-455.
Butz et al., 2001, Oncogene 20(45):6579-6586.
Deres et al., 2003, Science 299(5608):893-896.
Gitlin et al., 2003, J. Virol. 77(13):7159-7165.
Davis, 2000, Gastroenterology 118:S104-S114.
Bymock et al., 2000, Antiviral Chemistry & Chemotherapy 11:2, 79-95.
Ukita et al., 1999, J Med. Chem. 42:1293-1305.

(Continued)

*Primary Examiner*—Kamal A Saeed
*Assistant Examiner*—Kristin Bianchi
(74) *Attorney, Agent, or Firm*—Henry D. Coleman; R. Neil Sudol; William J. Sapone

(57) ABSTRACT

The present invention relates to novel antiviral helioxanthin analogs. These compounds may particularly be used alone or in combination with other drugs for the treatment of the following: hepadnaviruses, flaviviruses, herpesviruses and human immunodeficiency virus. In addition, compounds according to the present invention can be used to prevent or reduce the likelihood of the occurrence of tumors secondary to virus infection as well as other infections or disease states that are secondary to the virus infection.

25 Claims, 10 Drawing Sheets

OTHER PUBLICATIONS

Therien et al., 1993, Bioorg. Med. Chem. Lett. 3:2063-2066.
Iwasaki et al.,1995, Chem. Pharm. Bull. 43:1701-1705.
Ward et al., 1997, Nat. Prod. Rep. 14:43-74.
Cow et al., 2000, Can. J. Chem. 78:553-561.
Charlton et al., 1998, J. Nat. Prod. 61:1447-1451.
Burden et al., 1968. Tetrahedron Lett. 1035-1039.
He et al., 1997, J. Nat. Prod. 60:38-40.
Holmes et a1.,1971, J. Chem. Soc. ( C ) 2091-2094.
Stevenson et al., 1989, J. Nat. Prod. 52:367-375.
Charlton et al., 1996, J. Org. Chem. 61:3452-3457.
Mizufune et al., 2001, Tetrahedron Lett. 42:439.
Mellors et al., 1992, Mol. Pharmacol. 41:446-451.
Grove et al., 1995, Cancer Res. 55:3008-3011.

* cited by examiner

A
(μM)
integrated form →
replicative form →
0
0.3
1.0
3.0
10.0
0.3
Lamivudine
Percentage of control
Helioxanthin concentration (μM)
B
(μM)
integrated form →
replicative form →
0
0.03
0.1
0.3
1.0
3.0
Percentage of control
5-4-2 concentration (μM)

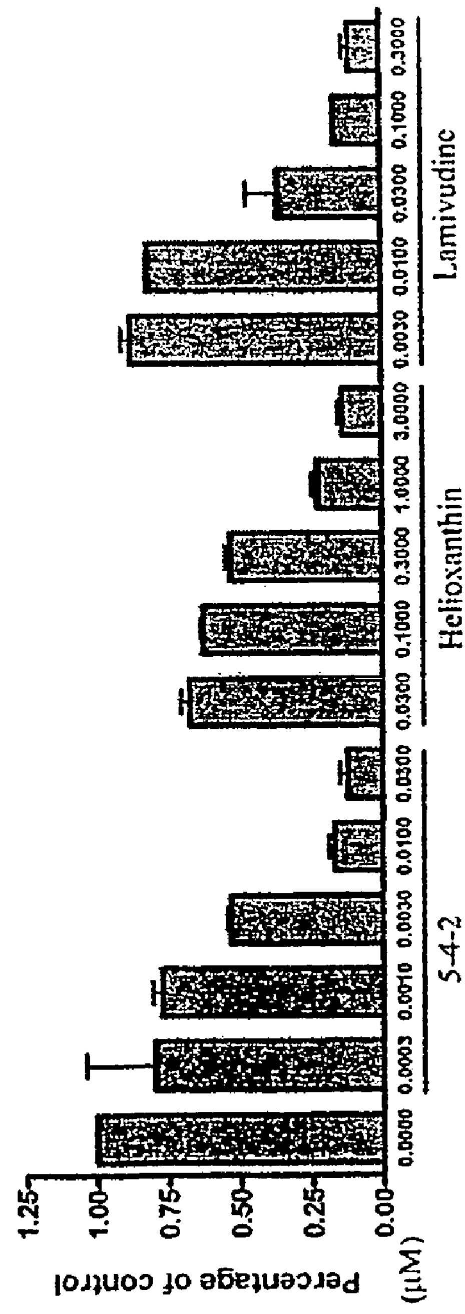
Fig 3 A
Percentage of control
1.25
1.00
0.75
0.50
0.25
0.00
(μM)
0.0000
0.0003
0.0010
0.0030
0.0100
0.0300
5-4-2
0.0300
0.1000
0.3000
1.0000
3.0000
Helioxanthin
0.0030
0.0100
0.0300
0.1000
0.3000
Lamivudine
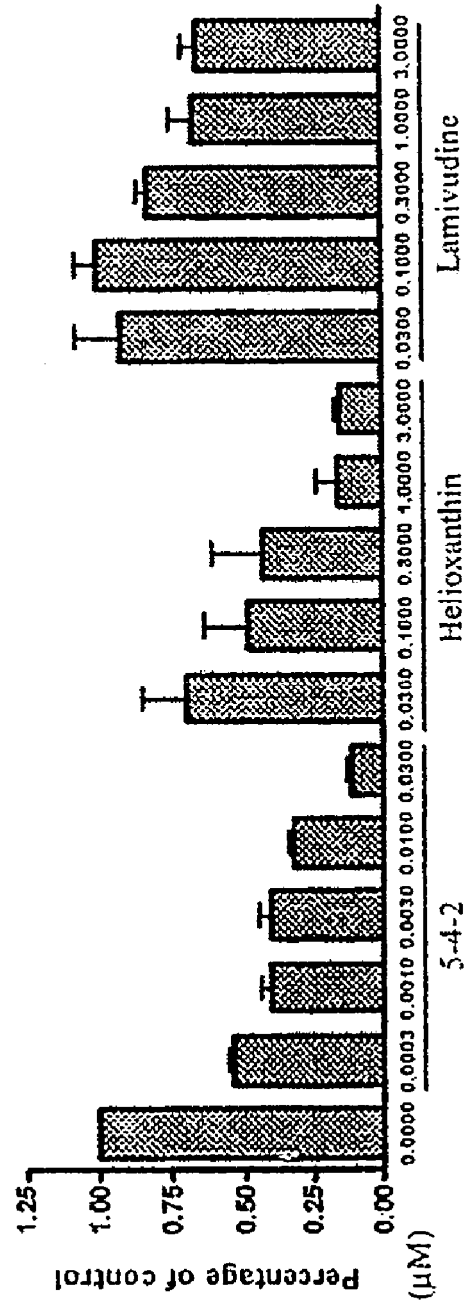
B
Percentage of control
1.25
1.00
0.75
0.50
0.25
0.00
(μM)
0.0000
0.0003
0.0010
0.0030
0.0100
0.0300
5-4-2
0.0300
0.1000
0.3000
1.0000
3.0000
Helioxanthin
0.0300
0.1000
0.3000
1.0000
3.0000
Lamivudine (μM)
0
0.1
0.3
1.0
3.0
10.0
0
0.1
0.3
1.0
3.0
10.0
3.5 Kb
2.4 Kb
2.1 Kb
GAPDH
B
(μM)
0
0.03
0.1
0.3
1.0
Lamivudine
0.3
3.5 Kb
2.4 Kb
2.1 Kb
GAPDH

B helioxanthin

22

ANTIVIRAL HELIOXANTHIN ANALOGS

RELATED APPLICATIONS AND SUPPORT

This application claims the benefit of priority of provisional application no. US60/568,348, filed May 5, 2004, the entire contents of which is incorporated by reference herein.

This invention was made with government support under Grant Number AI073299 awarded by the National Institutes of Health. The government has certain rights in the invention.

FIELD OF THE INVENTION

This invention relates to novel antiviral helioxanthin analogs. These compounds may particularly be used alone or in combination with other drugs for the treatment of the following: hepadnaviruses, flaviviruses, herpesviruses and human immunodeficiency virus. In addition, compounds according to the present invention can be used to prevent tumors secondary to virus infection as well as other infections or disease states that are secondary to the virus infection.

BACKGROUND OF THE INVENTION

Hepadnavirus

The family hepadnaviridae is a family of enveloped animal viruses with a core of DNA that cause hepatitis B in humans. The hepadnaviridae are not responsible for human hepatitis A (a single-stranded RNA enterovirus), human hepatitis C (Flaviridae family of single stranded RNA virus), or human hepatitis D (a closed circular negative-sense RNA satellite virus, "delta virus", that requires hepatitis B virus (HBV for replication). The hepadnaviridae family includes hepatitis viruses of other species, e.g. woodchuck, duck, ground squirrel, and heron, in addition to human and simian hepatitis B.

The HBV genome consists of a 3.2 kb partially double-stranded circular DNA with four overlapping reading frames that encode the viral DNA polymerase, the viral core antigen (HbcAg), the viral surface antigens and the X antigens (Seeger, C., and Mason, 2000, *Microbiol Mol Biol Rev.* 64 (1): 51-68; Tiollais et al., 1985, *Nature* 317 (6037): 489-495). There are four HBV transcripts synthesized: 3.5 kb, 2.4 kb, 2.1 kb and 0.7 kb. Synthesis of the HBV RNAs is under the control of the pregenomic/preC, S1, S2, X promoters and enhancer I, II (De Clercq, 1999, *Int J Antimicrob Agents.* 12(2): 81-95).

The 3.5 kb mRNA serves as the template for reverse transcription but also encodes the HBV DNA polymerase and the core antigen (Summers et al., 1982, *Cell* 29 (2): 403-415, Weimer et al., 1987, *J Virol.* 61 (10): 3109-3113).

Hepatitis B virus infection is a major health problem worldwide. Conservative estimates place the number of persons chronically infected with hepatitis B virus (HBV) at more than 300 million (Fu et al., 2000, *Antimicrob Agents Chemother.* 44: 3402-3407). This is a viral disease with a long incubation period (about 50 to 160 days) in contrast to Hepatitis A virus (infectious hepatitis virus) which has a short incubation period. The virus is usually transmitted by injection of infected blood or blood derivatives or merely by use of contaminated needles, lancets or other instruments. Clinically and pathologically, the disease is similar to viral hepatitis type A; however, there is no cross-protective immunity. HBV is a causative agent of both an acute and chronic form of hepatitis. More than 300 million people throughout the world are chronic carriers of HBV. Typically, the human host is unaware of infection and HBV infection leads to acute hepatitis and liver damage, abdominal pain, jaundice and elevated blood levels of certain enzymes. Additionally, HBV contributes to the formation of hepatocellular carcinoma and is second only to tobacco as a cause of human cancer. The mechanism by which HBV induces cancer is unknown, although it has been postulated that it may directly trigger tumor development or indirectly trigger tumor formation through chronic inflammation, cirrhosis and cell regeneration associated with the infection. Viral antigen (HBAg) is found in the serum after infection.

The best defense to date has been vaccination. Human serum-derived vaccines, through genetic engineering, have been developed. Although the vaccine has been found effective, production has been hampered by the limited supply of human serum from chronic carriers and a long and expensive purification process. Furthermore, each batch of vaccine must be tested in chimpanzees to ensure safety. Additionally, vaccines do not help the patients already infected with the virus.

Great efforts have been made to develop clinically useful treatments for hepatitis B but they have been met with limited success. For example, interferon and several nucleoside analogs have shown relatively low cure rate of hepatitis B and they have often produced serious adverse effects. IFN-α treatment has a very limited efficacy and patients have exhibited variable adverse effects (De Clercq, 1999, *Int J Antimicrob Agents.* 12(2): 81-95), which some patients cannot tolerate. Lamivudine (also known as 3TC) and adefovir are very potent HBV inhibition agents that target the HBV DNA polymerase (Chang et al., 1992. J. Biol. Chem. 267:13938-13942; Doong et al. 1991, *Proc. Natl. Acad. Sci. U.S.A.* 88: 8495-8499) and adefovir dipivoxil (Angus et al., 2003, *Gastroenterology* 125: 292-297). 2',3'-Dideoxycytidine (ddC) has been shown to have high toxicity on the central and peripheral nervous system. Another nucleoside analog, ara-AMP, was found to transiently suppress HBV infection but also has been shown to be extremely toxic as well.

Cyclopentyl purine derivatives have also shown anti-viral activity. The process for preparing such compositions have been disclosed in U.S. Pat. Nos. 4,999,428 and 5,015,739. Additionally, Onishi et al., in U.S. Pat. No. 5,777,116 have disclosed a method of making cyclopropane derivatives that include a xanthin-9-yl group.

Schinazi et al., in U.S. Pat. No. 5,684,010, have produced enationtiomerically pure beta-D-dioxolane nucleosides which show selective anti-hepatitis B activity. Additionally, Lin et al., in U.S. Pat. No. 5,830,881, have discovered that certain dideoxynucleoside analogs which contain a ribofuranosyl moiety having a L-configuration instead of the usual D-configuration showed potent inhibition of viral replication. However, unlike other nucleoside analogs, these analogs have shown very low toxicity to the host cells such as animal or human.

Hostetler, in U.S. Pat. No. 5,817,638, have produced nucleoside analogs such as 2',3'-dideoxycytosine, which are linked through a 5' phosphate of the pentose group to selected lipids such as dioleoylphosphatidylcholine. The lipophilic nature provides an advantage over the use of the nucleoside analog alone and makes it possible to incorporate them into the lamellar structure of liposomes. This form enables them to be taken up by liver cells which harbor the hepatitis B virus.

Processes have been disclosed by in U.S. Pat. Nos. 5,142,051, 5,641,763 and 5,869,467 for the production of N-(2-phosphonylmethoxyethyl) and N-(3-hydroxy-2-phosphonylmethoxypropyl) derivatives of pyrimidine and purine bases. These compounds also could include a xanthin-9-yl group. These compounds are regarded as acyclic analogues of nucleosides in which the nucleoside sugar moiety is replaced by a substituted carbon chain bearing hydroxy groups.

Although the compounds developed by Holly and others have not been tested specifically against hepatitis B viruses, they have shown in-vitro anti-viral activity against other DNA viruses such as the herpes viruses. Other analogs that show anti-Hepatitis B virus activity include phosphonomethyoxymethyl purine and pyrimidine derivatives as described by in U.S. Pat. Nos. 5,726,174 and 5,837,871.

Chang et al., on the other hand, in U.S. Pat. No. 5,929,038, have developed an anti-HBV compound that is an iridoid aglycone compound produced from the parent iridoid glycosides which are monoteropenoid compounds and are derived from medicinal plants. In addition to inhibiting HBV DNA synthesis, these compounds also protect the liver from hepatic damage such as that induced by carbon tetrachloride intoxication.

In the past, anti-HBV nucleotide analogues such as (−)-(2R,5S)-1-[2-(hydroxymethyl)oxathiolan-5-yl]cytosine (3TC), 9-[2-(phosphonomethoxy)ethyl]adenine (PMEA) and 9-[4-hydroxy-3-(hydroxymethyl)but-1-yl]guanine (PCV) have been used in clinical trials. However, some HBV-infected patients often experience a recurrence of HBV after a period of treatment with 3TC or PCV; this recurrence is due to the emergence of viral resistance. Additionally, the 3TC-resistant HBV, for example, becomes cross-resistant to other anti-HBV nucleotide analogs.

Therefore, one major concern of nucleoside analogue treatment is the emergence of drug-resistant variants of HBV (Fu et al., 1999, *Biochem Pharmacol.* 57 (12):1351-1359; Leung et al., 2001, *Hepatology.* 33 (6): 1527-1532; Liaw et al., 2000, *Gastroenterology.* 119(1): 172-180). Given the longer period of treatment using lamivudine, resistance was shown to increase from 14% at 1 year to 57% and 70% for years 3 and 5 respectively, (Liaw et al., 2003, *J Gastroenterol Hepatol.* 18:239-245) with respect to patients treated with lamivudine. With the intensive efforts in the search for effective antiviral agents against drug-resistant HBV, some nucleotide analogues have been developed and are under clinical evaluation for the treatment of 3TC-resistant HBV infections (Mutimer, 2001, *J. Clin. Virol.* 21:239-242; Levine et al., 2002, *Antimicrob. Agents Chemother.* 46:2525-2532). Although adefovir is a new drug recently approved by the FDA, Angus et al. reported that a novel mutation in the HBV polymerase emerged, which rendered the HBV resistant to the antiviral treatment (Angus et al., 2003, *Gastroenterology* 125 (2):292-297).

RNAi and ribozymes have been used in down regulating HBV RNA and core protein expression (McCaffrey et al., 2003, *Nature Biotechnol.* 21 (6): 639-644: Shlomai et al., 2003, *Hepatology.* 37 (4): 764-770 and Morrisey et al., 2002, *J Viral Hepat.* 9 (6): 411-418). HBV core protein the major capsid protein of HBV. Its phosphorylated form might be important for pregenomic RNA packaging, and its native form is important for viral DNA replication (Lan et al., 1999, *Virology.* 259 (2): 342-348). Core protein also functions as a transcriptional activator of the HBV pregenomic/preC promoter (Kwon et al., 2002, *Biochem Cell Biol.* 80 (4):445-455). Butz et al. developed a peptide aptamer, which can bind to the core protein and interfere with capsid formation (Butz et al., 2001, *Oncogene* 20(45):6579-6586). Deres et al. (Deres et al., 2003, *Science.* 299 (5608): 893-896) discovered a non-nucleoside inhibitor of HBV nucleocapsid maturation. Both studies demonstrated that the inhibition of HBV replication could be achieved by interfering with the assembly of core protein and capsid maturation. McCaffrey and Shlomai also independently observed HBV DNA inhibition by siRNA directed to the core gene (McCaffrey et al., 2003, *Nature Biotechnol.* 21 (6):639-644; Shlomai et al., 2003, *Hepatology.* 37 (4):764-770). They targeted different sequences in the same core gene region and got different degrees of inhibition on HBV replication. However, establishing the RNAi, as a viable therapeutic approach requires resolving several major issues: persistence of the RNAi inhibitory effect, efficient delivery system, viral resistance (Gitlin et al., 2003, *J. Virol.* 77 (13):7159-7165) and stabilization of RNAi.

Flaviviruses

Flaviviruses belong to the genus *Flavivirus* of the family Togaviridae. According to virus taxonomy, about 50 viruses including Hepatitis C virus (HCV), Yellow Fever virus, Dengue Virus, Japanese Encephalitis virus, West Nile virus and related flaviviruses. The viruses belonging to the genus *Flavivirus* are simply called flaviviruses.

The flaviviruses are agents of infectious disease and predominate in East, Southeast and South Asia and Africa, although they may be found in other parts of the world as well. Japanese encephalitis virus is the causative agent of Japanese encephalitis (JE). The mortality rate from JE is rather high and the disease brings heavy sequelae. Although found in Japan, the disease has spread to other parts of Asia and is now found predominantly outside of Japan, primarily in South and Southeast Asia.

Yellow fever is a tropical mosquito-borne viral heptatitis, due to Yellow Fever virus (YFV), with an urban form transmitted by *Aedes aegypti*, and a rural, jungle or sylvatic form from tree-dwelling mammals by various mosquitoes of the *Haemagogus* species complex. Yellow fever is characterized clinically by fever, slow pulse, albuminuria, jaundice, and congestion of the face and hemorrhages, especially hematemesis ("black vomit"). It is fatal in about 5-10% of the cases.

Japanese encephalitis virus ("JEV") is the causative agent of Japanese encephalitis (JE). JE is an epidemic encephalitis or encephalomyelitis of Japan, Russia (Siberia) and other parts of Asia. The mortality rate from JE is rather high and the disease brings heavy sequelae. Although found in Japan, the disease has spread to other parts of Asia and is now found predominantly outside of Japan, primarily in South and Southeast Asia.

West Nile virus is the causative agent of West Nile fever, a disease characterized by headache, fever, masculopapular rash, myalgia, lymphadenopathy and leukopenia. The virus is spread by *Culex* mosquitoes from a reservoir in birds.

Dengue is a disease of tropical and subtropical regions occurring epidemically and caused by Dengue virus, one of a group of arboviruses which causes the hemorrhagic fever syndrome. Four grades of severity are recognized: grade I: fever and constitutional symptoms, grade II: grade I plus spontaneous bleeding (of skin, gums or gastrointestinal tract), grade III: grade II plus agitation and circulatory failure and grade IV: profound shock. The disease is transmitted by a mosquito of the genus *Aedes* (generally *A. aegyptiI*, but frequently, *A. albopictus*). Also called Aden, bouquet, breakbone, dandy, date, dengue (hemorrhagic) or polka, solar fever, stiffneck fever, scarlatina rheumatica or exanthesis arthorosia. "Hemorrhagic dengue" is a more pathogenic epidemic form of dengue that has erupted in a number of epidemic outbreaks in the Pacific region in recent years.

Infection with dengue viruses is a major public health problem in tropical countries, especially in Southeast Asia and the Western Pacific, but dengue viruses may also be found in the Americas. As the dengue virus is transmitted to humans via the *Aedes aegypti* mosquito, it is not unexpected that the tropical and subtropical countries, in particular, those in Southeast Asia are highly endemic for dengue.

A major concern and increasing problem for public health officials has been the occurrence of severe complications which arise from dengue viral infections. Both dengue hemorrhagic fever (DBF) and shock syndrome (DSS) are clinical outcomes related to the presence of pre-existing immunity to a heterologous dengue virus serotype. Dengue hemorrhagic fever is initially characterized by a minor febrile illness lasting approximately 3-5 days. The patient may deteriorate at defervescence into the next phase of the syndrome with hemostatic disorders and increased vascular permeability frequently accompanied by internal bleeding and shock. As many as 1.5 million children are reported to have been hospitalized with 33,000 deaths from this syndrome since it was first recognized in Thailand in the 1950's. DHF/DSS has since continued to persist in South Asia. DHS/DSS is also found in a number of tropical or near tropical countries, including Cuba, Burma, Indonesia, India, Maldives, Sri Lanka and the South Pacific Islands. Dengue outbreaks are usually associated with a density of mosquito vectors, in particular, *Aedes aegypti.*

Dengue viruses can be divided into 4 serotypes which are antigenically very similar to each other, but which differ enough to elicit only partial cross-protection after infection by one serotype. Such an infection by one serotype therefore, does not provide life-long immunity to the other serotypes. Vaccine approaches to preventing dengue infections have been unsuccessful to date.

The term "Hepatitis C Virus" or (HCV) is used throughout the specification to describe the hepatitis virus which is the causative agent of non-A, non-B hepatitis. The Disease in the acute stage is, in general, milder than hepatitis B, but a greater proportion of such infections become chronic. It is clinically diagnosed by a well-defined set of patient symptoms, including jaundice, hepatic tenderness and an increase in the serum levels of alanine aminotransferase and aspartate aminotransferase.

HCV is an enveloped virus containing a positive-sense single-stranded RNA genome of approximately 9.4 kb. The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation. Translation of the HCV genome is initiated by a cap-independent mechanism known as internal ribosome entry. This mechanism involves the binding of ribosomes to an RNA sequence known as the internal ribosome entry site (IRES). An RNA pseudoknot structure has recently been determined to be an essential structural element of the UCV IRES. Viral structural proteins include a nucleocapsid core protein (C) and two envelope glycoproteins, E1 and E2. HCV also encodes two proteinases, a zinc-dependent metalloproteinase encoded by the NS2-NS3 region and a serine proteinase encoded in the NS3 region. These proteinases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown.

Colacino et al. in U.S. Pat. Nos. 5,821,242 and 5,891,874, have developed a series of benzimidazole compounds which inhibit replication in other flaviviruses such as Hepatitis C by interfering with the structure and function of the viral replication complex.

Ribavirin (1-beta-D-ribofuranosyl-1-1,2,4-triazole-3-carboxamide), which is structurally similar to guanosine, has in vitro activity against several DNA and RNA viruses including Flaviviridae (Davis, 2000, Gastroenterology 118:S104-S114). Ribavirin reduces serum amino transferase levels to normal in 40% or patients, but it does not lower serum levels of HCV-RNA (Davis, 2000, Gastroenterology 118:S104-S114). Thus, ribavirin alone is not effective in reducing viral RNA levels. Additionally, ribavirin has significant toxicity and is known to induce anemia.

Interferons (IFNs) are compounds that have been commercially available for the treatment of chronic hepatitis for nearly a decade. IFNs are glycoproteins produced by immune cells in response to viral infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary and a sustained response occurs in only 8%-9% of patients chronically infected with HCV (Davis, 2000, Gastroenterology 118:S104-S114).

A number of patents disclose HCV treatments using interferon-based therapies. For example, U.S. Pat. No. 5,980,884 discloses methods for retreatment of patients afflicted with HCV using consensus interferon. U.S. Pat. No. 5,942,223 discloses an anti-HCV therapy using ovine or bovine interferon-tau. U.S. Pat. No. 5,928,636 discloses the combination therapy of interleukin-12 and interferon alpha for the treatment of infectious diseases including HCV. U.S. Pat. No. 5,908,621 discloses the use of polyethylene glycol modified interferon for the treatment of HCV. U.S. Pat. No. 5,849,696 discloses the use of thymosins, alone or in combination with interferon, for treating HCV. U.S. Pat. No. 5,830,455 discloses a combination HCV therapy employing interferon and a free radical scavenger. U.S. Pat. No. 5,738,845 discloses the use of human interferon tau proteins for treating HCV. Other interferon-based treatments for HCV are disclosed in U.S. Pat. Nos. 5,676,942, 5,372,808 and 5,849,696.

The U.S. FDA has approved Schering's Ribavarin product, Rebetol capsules to treat chronic HCV infection in combination with Schering's alpha interferon products. Hoffman La Roche is selling ribavirin under the name CoPegus, also for use in combination with interferon for the treatment of HCV.

Other approaches have been attempted and are reviewed by Bymock et al., in Antiviral Chemistry & Chemotherapy, 11:2; 79-95 (2000). A few of the more recent approaches attempted are reviewed below.

Specifically, a method for the treatment of hepatitis C infection (2004/0006007) and flaviviruses and pestiviruses) in humans and other host animals is disclosed that includes administering an effective amount of a biologically active 1',2', or 3'-branched beta-D or beta-L nucleosides or a pharmaceutically acceptable salt or prodrug thereof, administered either alone or in combination, optionally in a pharmaceutically acceptable carrier. WO 01/96353 discloses 3'-prodrugs of 2'-deoxy-beta-L-nucleosides for the treatment of HBV. U.S. Pat. No. 4,957,924 discloses various therapeutic esters of acyclovir. Other patent applications disclosing the use of certain nucleoside analogs to treat hepatitis C virus include: WO 01/32153, WO 01/60315, WO 02/057425, WO 02/057287, WO 02/18404. U.S. Pat. No. 6,323,180 and U.S. Pat. Pub. No. 2004/0033959 discloses the use of viral protease inhibitors to inhibit the replication of HCV.

Herpesviruses

Herpesviruses include Herpes Simplex Virus types 1 and 2 (HSV-1 and HSV-2), Human Cytomegalovirus (HCMV), Epstein-Barr Virus (EBV) and Equine herpesviruses 1 and 4 (EHV-1 and EHV-4). The herpesviruses comprise a large family of double stranded DNA viruses. They are also a source of the most common viral illnesses in man. Eight of the herpes viruses, herpes simplex virus types 1 and 2 (HSV-1 and HSV-2), varicella zoster virus (VZV), human cytomegalovirus (HCMV), Epstein-Barr virus (EBV), and human herpes viruses 6, 7, and 8 (HHV-6, HHV-7, and (HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immune-compromised patients such as retinitis, pneumonia, and gastrointestinal disease. VZV is the causitive agent of chicken pox and shingles. EBV causes infectious mononucleosis and can also cause lymphomas in immune-compromised patients. It has been associated with Burkitt's lymphoma, nasopharyngeal carcinoma, and Hodgkins disease. HHV-6 is the causitive agent of roseola and may be associated with multiple sclerosis and chronic fatigue syndrome. HHV-7 disease association However, not all patients are responsive and a large number fail this therapy. In fact, approximately 30-50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regimen as well as intrinsic pharmacological barriers to exposure provides fertile ground for resistance to emerge.

Arylnaphthalene Lignan Lactones

Arylnaphthalene lignan lactones are natural products found in plant species and many of them exhibit diverse biological activities, such as phosphodiesterase inhibition, (Ukita et al., 1999, *J Med. Chem.* 42:1293-1305) leukotriene biosynthesis inhibition, (Thérien et al., 1993, *Bioorg. Med. Chem. Lett.* 3:2063-2066) and hypolipidemic, (Iwasaki et al., 1995, Chem. Pharm. Bull. 43:1701-1705) antitumoral (Ward et al., 1997, *Nat. Prod. Rep.* 14:43-74) and antiviral activities (Cow et al., 2000, *Can. J. Chem.* 78: 553-561, Charlton et al., 1998, *J. Nat. Prod.* 61:1447-1451). Helioxanthin is an arylnaphthalene lignan lactone isolated from the root of *Heliopsis scabra* Dunal (Compositae) (Burden et al., 1968, *Tetrahedron Lett.* 1035-1039) and the whole plant of *Taiwania cryptomerioides* Hayata (Taxodiaceae), (He et al., 1997, *J. Nat. Prod.* 60: 38-40) and the synthesis of which have been carried out by the inter- or intramolecular Diels-Alder reactions (Holmes et al., 1971, *J. Chem. Soc.* (C) 2091-2094; Stevenson et al., 1989, J. Nat. Prod. 52:367-375; Charlton et al., 1996, *J. Org. Chem.* 61:3452-3457) and benzannulation reaction (Mizufune et al., 2001, *Tetrahedron Lett.* 42:439).

U.S. Pat. No. 6,306,899 discloses that helioxanthin and certain analogues decreased the RNA level of HBV and antigen expression as well as selectively inhibited HBV replication in the cell culture model. This class of compound offers unique characteristic in anti-HBV chemotherapy. Therefore, it is of interest to synthesize more analogues of helioxanthin for studying structure-activity relationships and developing more selective, potent antiviral agents.

OBJECTS OF THE INVENTION

It is an object of the present invention to provide compounds, medicaments including compositions (e.g., pharmaceutical compositions) and methods of treating and/or preventing infections from hepadnviruses, flaviviruses, herpesviruses, human immunodeficiency virus and related conditions and/or disease states in patients.

It is an additional object of the present invention to provide, in certain embodiments, a method of preventing the formation of hepadnavirus, flavivirus, herpesvirus or human immunodeficiency virus related tumors in patients exposed to said virus or who have a viral infection. It is still a further object of the present invention to provide a method of treating 3TC (L(−)SddC) resistant HBV infections.

SUMMARY OF THE INVENTION

The invention is directed to an isolated compound of the formula:

I

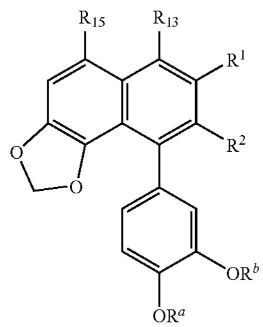

where $R^1$ and $R^2$ are independently $C_1$-$C_6$ alkyl, COO—$Na^+$,

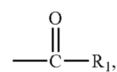

a —$(CH_2)_n$aryl, —$(CH_2)_n$Z-($C_1$-$C_6$)alkyl, —$(CH_2)_n$Z-$(CH_2)$,aryl, each of which groups may be optionally substituted with one or more halogens, OH, COOH, $C_1$-$C_3$ alkyl or CN, a —$(CH_2)_n NR^3R^4$ group, or $R^1$ and $R^2$ together with the adjacent benzene ring form a 5- or 6-membered heterocyclic ring according to the structure:

Ia $$\text{ring: } X^1 - Y - X^2$$

where Y is O, a N—$R^{6a}$ group or a —N($R^7$)—N($R^9$)— group;

$X^1$ and $X^2$ are independently a $CH_2$ or C═O group;

$R_1$ is OH, a —($C_1$-$C_6$)alkyl, a —$(CH_2)_n$aryl, a —$(CH_2)_n$Z-($C_1$-$C_6$)alkyl, a —$(CH_2)_n$Z-$(CH_2)_n$aryl each of which groups may be optionally substituted with one or more halogens, OH, COOH, $C_1$-$C_3$ alkyl or CN, or wherein $R_1$ is a —$(CH_2)_n NR^5R^6$ group;

$R^3$ and $R^4$ are independently selected from H, —($C_1$-$C_6$) alkyl or a

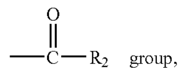

where $R_2$ is H, a —($C_1$-$C_6$)allyl, a —$(CH_2)_n$aryl, —$(CH_2)_j$O—($C_1$-$C_6$)alkyl or a —$(CH_2)_j$O—$(CH_2)_n$alkyl;

$R^5$ and $R^6$ are independently selected from H, —($C_1$-$C_4$) alkyl, —$(CH_2)_n$aryl, —$(CH_2)_j$O—($C_1$-$C_6$)alkyl or —$(CH_2)_j$O—$(CH_2)_n$aryl;

$R^{6a}$ is H, a $C_1$-$C_6$ alkyl optionally substituted with a hydroxyl group or aryloxy group, —$OR^9$ or N—$R^{10}$;

$R^7$, $R^8$, and $R^9$ are independently H or a $C_1$-$C_6$ alkyl group which may be optionally substituted with a hydroxyl group;

$R^{10}$ is H, —($C_1$-$C_6$)alkyl or —C(═O)($C_1$-$C_6$)alkyl;

Z is O or NH;

$R_{13}$ is H, OH, —O($C_1$-$C_4$)alkyl, ($C_1$-$C_4$) alkyl;

$R_{15}$ is H, OH, —O($C_1$-$C_4$)alkyl, ($C_1$-$C_4$) alkyl, F, Cl, Br or I;

$R^a$ and $R^b$ are independently a —($C_1$-$C_6$)alkyl, or together form a —$(CH_2)_k$— group;

j is 1, 2, 3, 4 or 5;

k is 1 or 2; and n is 0, 1, 2, 3, 4 or 5;

with the proviso that when Y is O, $R_{15}$ is Cl, Br or I and when $R^1$ and $R^2$ is COOH, $R_{15}$ is Cl, or I, or their anomers, pharmaceutically acceptable salts, solvates, or polymorphs thereof.

The invention is further directed to compositions comprising these compounds. These compositions may be pharmaceutical compositions for use as antiviral agents and thus comprise an anti-viral effective amount of the compound the present invention. The compositions of the present invention may further comprise other antiviral agents.

The compounds and compositions of the present invention may be used to manufacture medicaments for use in modulating the replication of a virus and/or preventing and/or treating infection of a virus. In a particular embodiment, the virus is a hepadnavirus, flavivirus, or herpesvirus. In another embodiment, the virus is a human immunodeficiency virus, particularly where the compound has the structure:

V

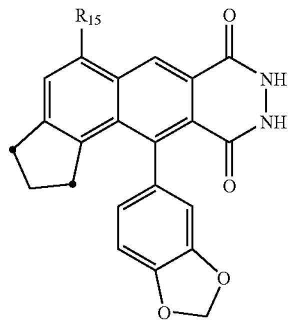

Where $R_{15}$ is H, OH, —O($C_1$-$C_4$)alkyl, ($C_1$-$C_4$) alkyl, F, Cl, Br or I, more preferably H, Br or I.

Thus, the invention is also directed to a method for modulating replication of virus in a host cell infected with said virus comprising administering to said host cell the compound or composition of the present invention in an amount effective to modulate said replication as well as a method for preventing and/or treating infection of virus in a mammal in need thereof comprising administering to said mammal an amount of the compound of the present invention in an amount effective to prevent or treat infection of said virus.

The invention is also directed to a method of preventing hepatoma secondary to a Hepatitis B or Hepatitis C virus infection or tumors secondary to herpesvirus infection such as Burkitt's lymphoma, nasopharyngeal carcinoma, Hodgkins disease, Kaposi's sarcoma, body cavity based lymphomas, and multiple myeloma. In a related aspect, the invention is directed to the use of these compounds for the manufacture of a medicament acting as an antiviral agent, particularly for preventing or inhibiting hepadnavirus, flavivirus and/or herpesvirus infection.

BRIEF DESCRIPTION OF THE FIGURES

FIG. 1A shows the synthetic scheme for compounds 1a and 1-8. 6: $R_3$═O, $R_4$═Bn, $R_5$═$CH_2$ OBn; 7: $R_3$═O, $R_4$═H, $R_5$═$CH_3$; 8: $R_3$═NH, $R_4$═Bn, $R_5$═$CH_2$ OBn. Reagents and conditions: (a) $HO(CH_2)_2OH$, p-TsOH, benzene, reflux; (b) n-BuLi, piperonal, THF, −78° C. to rt; (c) maleic anhydride, AcOH, $AC_2O$, $CH_2Cl_2$, 140° C., 24 h; (d) $NaBH_4$, THF, 0° C., 1 h, and then 10% HCl; (e) aq. NaOH in MeOH, 70° C., 1 h; (f) BnBr, KOH, 140° C., 3 h; (g) NaOH in MeOH: $H_2O$ (4:1), 70° C. 12 h; (h) $HO(CH_2)_3$ OBn (for 6) or $H_2N(CH_2)_3OBn$ (for 8), DCC, DMAP (for 6) or 1-HOBt (for 8) $CH_2Cl_2$, 0° C. to rt, 4-18 h; (i) Pd/C, THF, $H_2$, rt, 14 h.

FIG. 1B shows the synthetic scheme for compounds 1a and 1b and 9-21. 1a: $R_6$, $R_7$═—$CH_2$—; 1b: $R_6$═$R_7$═$CH_3$; 9: $R_6$, $R_7$═—$CH_2$—, $R_8$═H; 10: $R_6$, $R_7$═—$CH_2$—, $R_8$═$(CH_2)_3$ OBn; 11: $R_6$, $R_7$═—$CH_3$, $R_8$═H; 12: $R_6$, $R_7$═—$CH_2$—, —$R_{11}$═$NH_2$; 13: $R_6$, $R_7$═—$CH_2$—, $R_{11}$═$NHCH_3$; 14: $R_6$, $R_7$═—$CH_2$—, $R_{11}$═$N(CH_3)_2$; 15: R═$R_7$═—$CH_3$, $R_{11}$═$NH_2$; 16: $R_6$, $R_7$═—$CH_2$—, $R_8$═H, $R_9$═$CH_2$, $R_{10}$═CO; 17: $R_6$, $R_7$═—$CH_2$—, $R_8$═$CH_3$, $R_9$═$CH_2$, $R_{10}$═CO; 18: $R_6$, $R_7$═—$CH_2$—, $R_8$═H, $R_9$═CO, $R_{10}$═$CH_2$; 19: $R_6$, $R_7$═—$CH_2$—, $R_8$═$CH_3$, $R_9$═CO, $R_{10}$═$CH_2$; 20: $R_6$, $R_7$═—$CH_2$—, $R_8$═$(CH_2)_3OH$, $R_9$═$COR_{10}$═$CH_2$ 21: $R_6$, $R_7$═—$CH_3$, $R_8$═H, $R_9$═CO, $R_{10}$═$CH_2$.

Reagents and conditions: (a) $HO(CH_2)_2OH$, p-TsOH, benzene, reflux; (b) n-BuLi, piperonal (for 9 and 12) or 3,4-dimethoxybenzaldehyde (for 11 and 15), THF, −78° C. to rt; (c) maleimide, AcOH, $Ac_2O$, $CH_2Cl_2$, 140° C., 24 h; (d) $HO(CH_2)_3OBn$, $PPh_3$, DEAD, THF, 0° C. to rt, 30 h; (e) KOH in DMSO, MeI, rt, 24 h; (f) Zn in AcOH, 100° C., 48 h (16 and 18 from 9; 20 from 10; 22 from 11); (g) KOH in DMSO, MeI, rt, 1 h; (h) Pd/C, THF, $H_2$, rt 20 h.

Figure 1A:
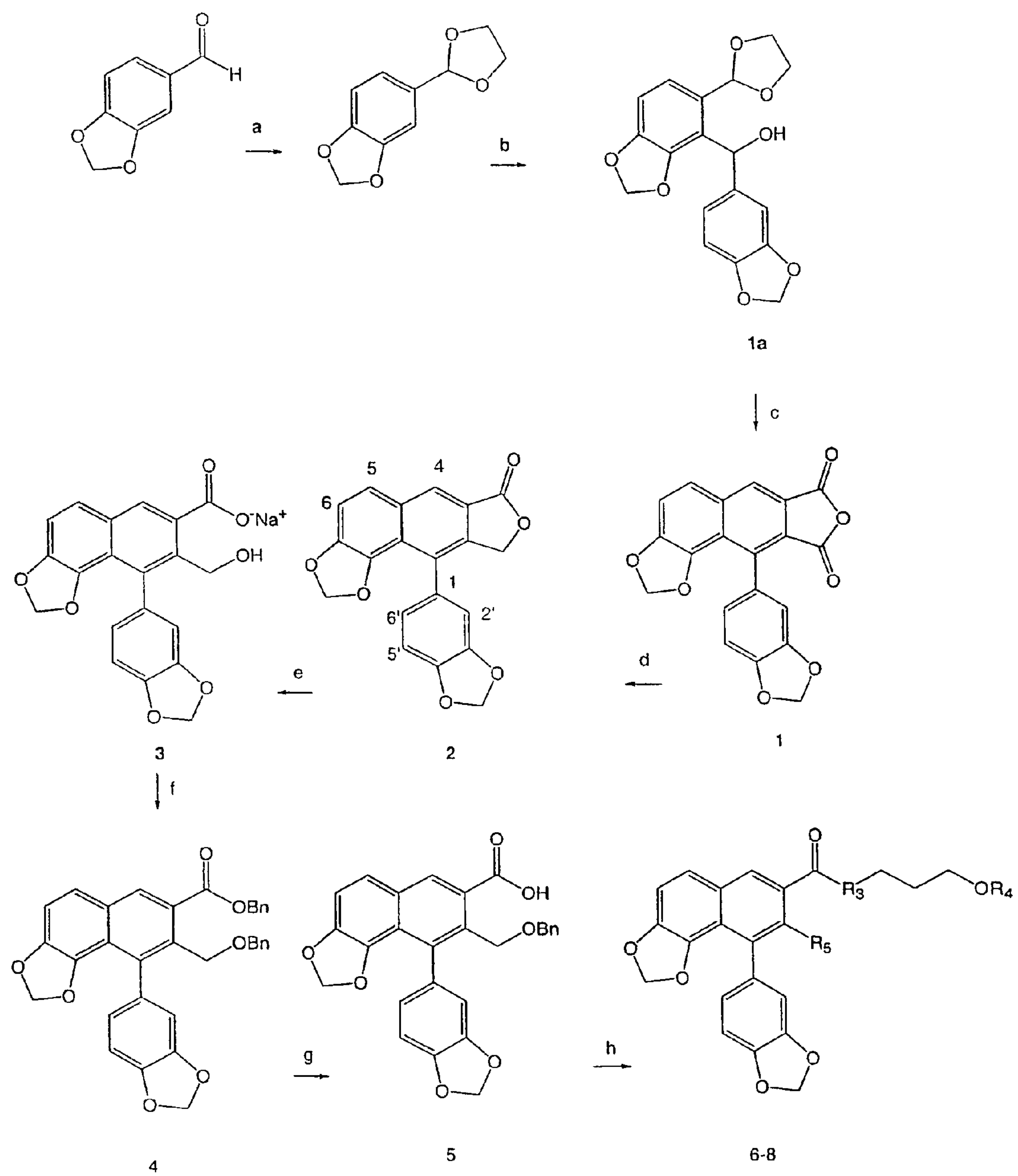
FIGS. 1A-E represent the chemical schemes used for the synthesis of compounds according to the present invention.
Figure 1B:
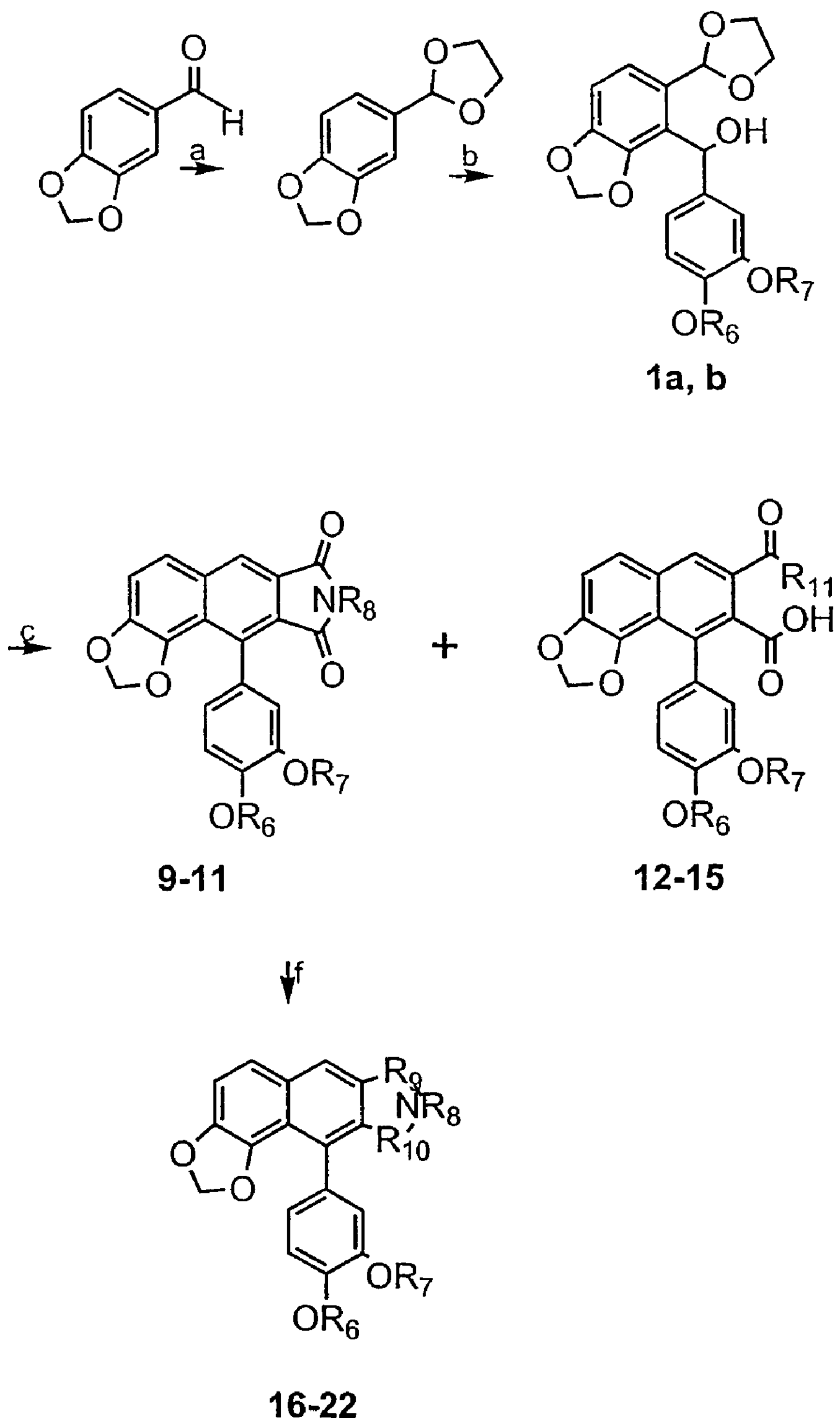
Figure 1C:
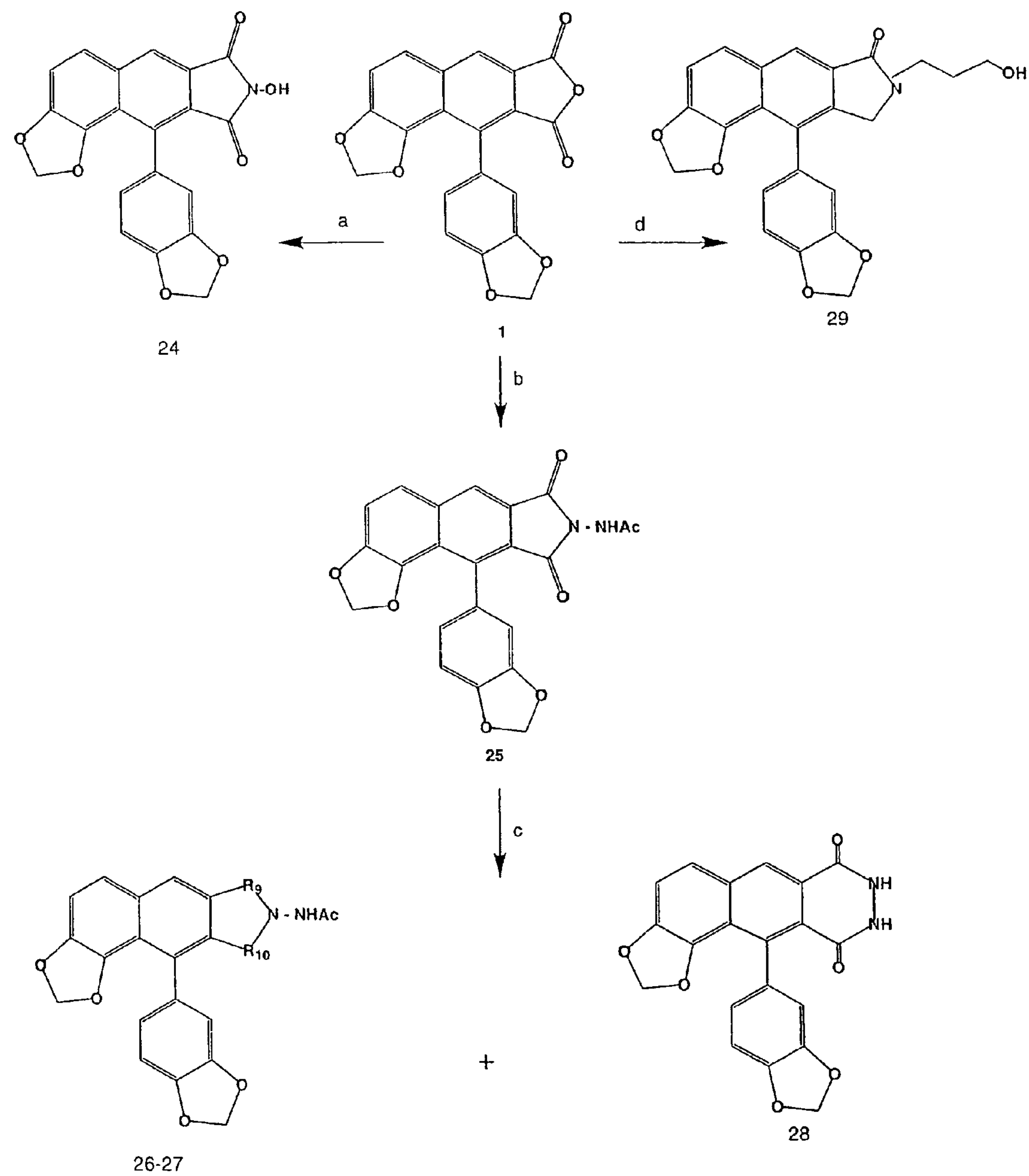

FIG. 1C shows the synthetic scheme for compounds 24-28. 26: $R_9$═CO, $R_{10}$═$CH_2$ 27: $R_9$═$CH_2$ $R_{10}$═CO.

Reagents and conditions: (a) $NH_2OH.HCl$, $N(Et)_3$, EtOH, reflux, 12 h; (b) $NH_2NH_2.H_2O$, AcOH, reflux, 24 h; (c) Zn in AcOH, 100° C., 5 h; (d) $H_2N(CH_2)_3$ OH, toluene, reflux, 3 h.

Figure 1D:
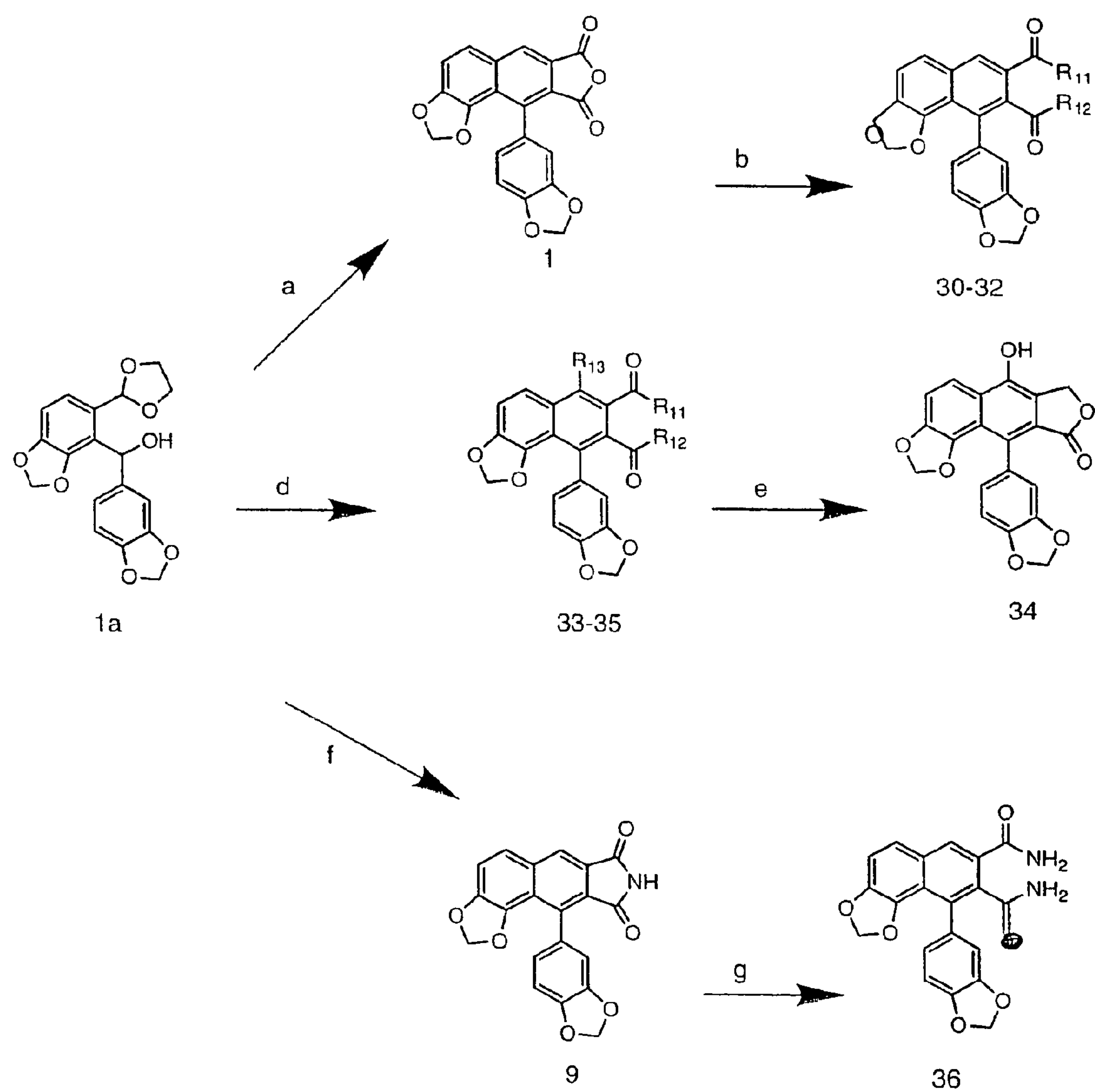

FIG. 1D shows the synthetic scheme for compounds 1, 9, 30-36. 30: $R_{11}$═OMe, $R_{12}$═OMe; 31: $R_{11}$═OH, $R_{12}$═OMe; 31: $R_{11}$═OH, $R_{12}$═OH; 33: $R_{11}$═OEt, $R_{12}$═OEt, $R_{13}$═OH; 35: $R_{11}$═OEt, $R_{12}$═OEt, $R_{13}$═OMe Reagents and conditions: (a) maleic anhydride AcOH, $Ac_2O$, $CH_2$ $Cl_2$, 140° C., 24 h; (b) $TMSCHN_2$, MeOH; THF (1:2), rt, 12 b; (c) KOH in MeOH, reflux, 2-24 h; (d) DEADC, AcOH, $CH_2$ $Cl_2$, 140° C., 24 h; (e) LAH, THF, 0° C. to rt, 2 h; (f) maleimide, AcOH, $Ac_2O$, $CH_2Cl_2$, 140° C., 24 h; (g) $NH_4OH$, THF, 40° C., 72 h.

Figure 1E:
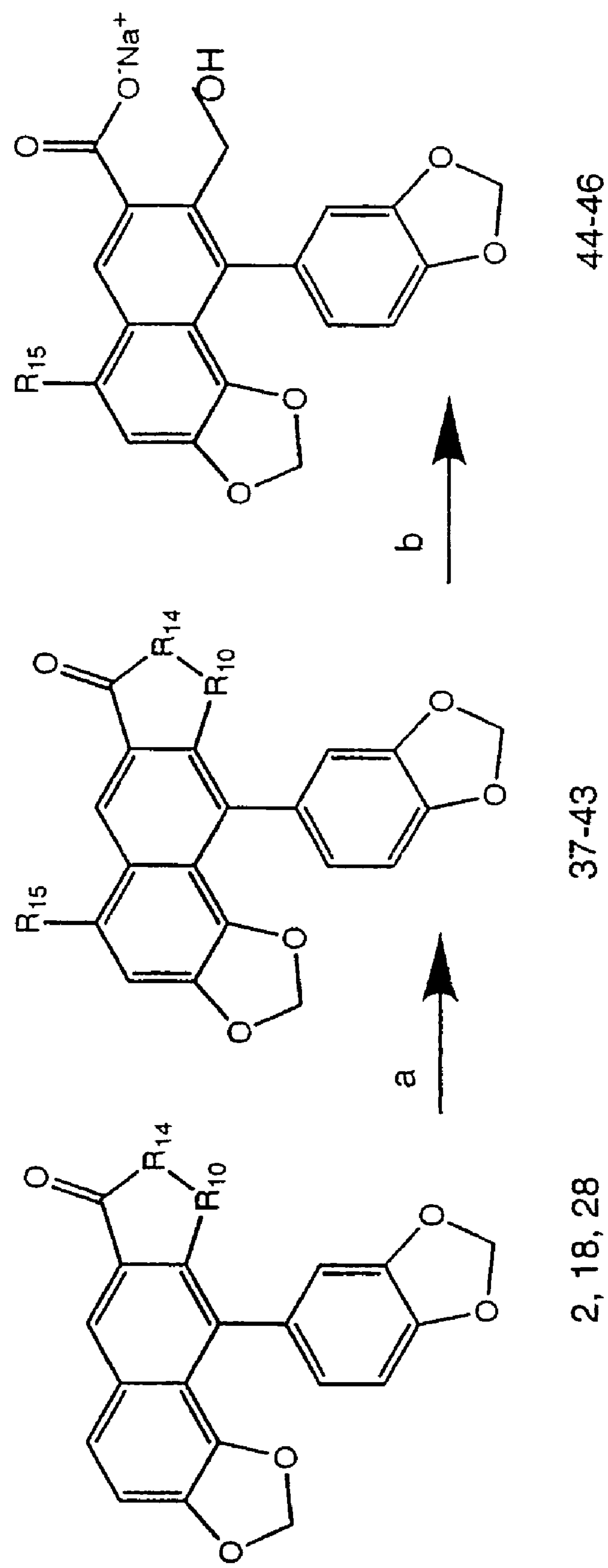

FIG. 1E shows the synthetic scheme for compounds 37-46.2: $R_{10}$=$CH_2$ $R_{14}$=O; 18: $R_{10}$=$CH_2$ $R_{14}$=NH; 28: $R_{10}$=CO, $R_{14}$=NHNH; 37: $R_{10}$=$CH_2$, $R_{14}$=O, $R_{15}$=Cl; 38: $R_{10}$=$CH_2$, R)$_{14}$=O, $R_{15}$=Br; 39: $R_{10}$=$CH_2$, $R_{14}$=O, $R_{15}$=I; 40: $R_{10}$=$CH_2$, $R_{14}$=NH, $R_{15}$=Br; 41: $R_{10}$=CO, $R_{14}$=NHNH, $R_{15}$=Cl; 42: $R_{10}$=CO, $R_{14}$=NHNH, $R_{15}$=Br; 43: $R_{10}$=CO, $R_{14}$=NHNH, $R_{15}$=I; 44: $R_{15}$=Cl; 45: $R_{15}$=Br; 46: $R_{15}$=I Reagents and conditions: (a) N-chlorosuccinimide (for 37 and 41) or N-bronosuccinimide (for 38 and 42) or N-iodosuccinimide (for 39 and 43), $CH_3CN$ or THF, conc $H_2O_4$ (cat.), rt or reflux, 20-48 h (37-39 from 18, 41-43 from 28); (b) aq. NaOH in MeOH, 70° C., 1-3 h (from 37-39).

Figure 2:
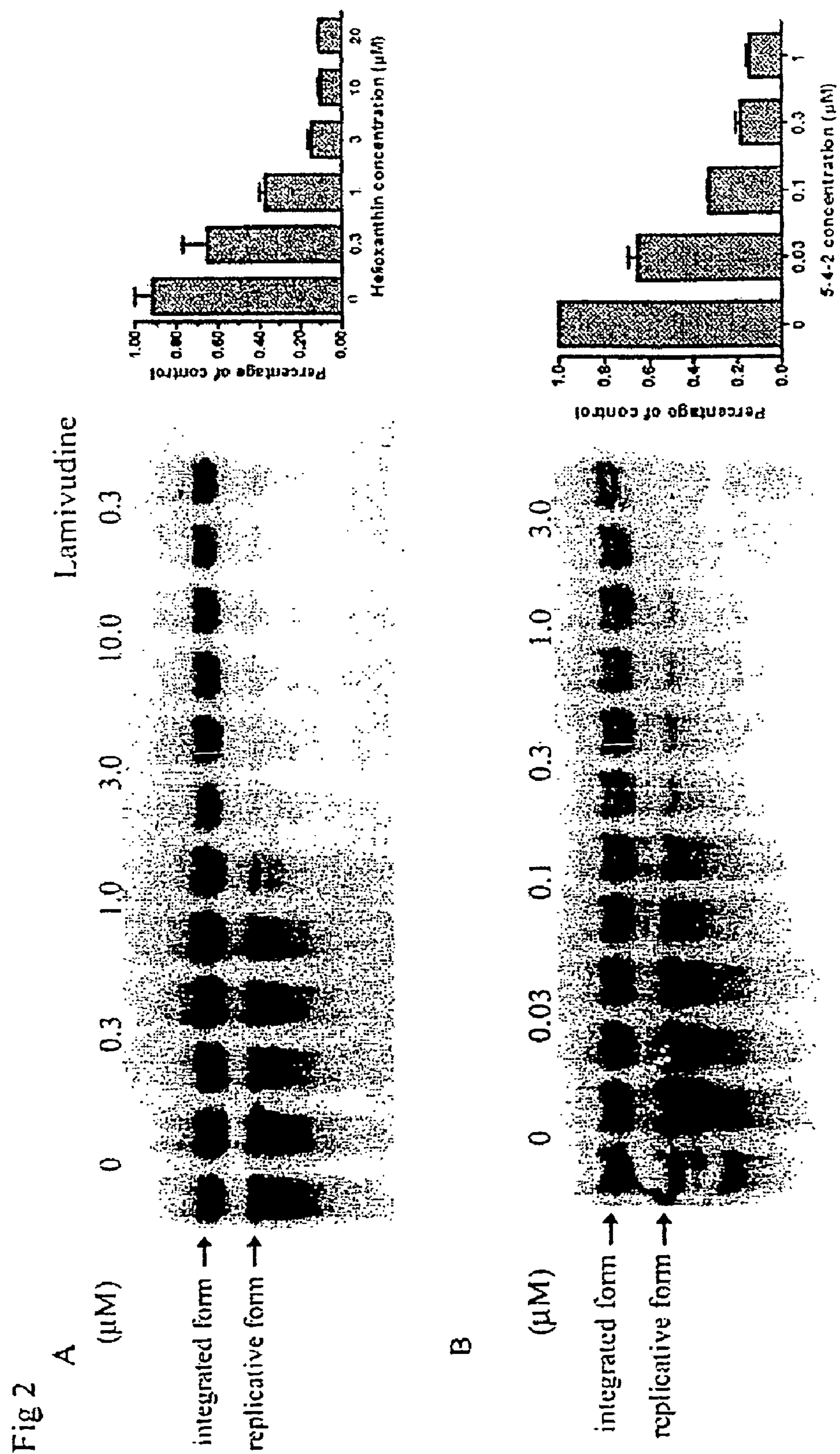

FIG. 2 shows HBV replication inhibition by helioxanthin (A) and 22 (B). Southern blot hybridization analysis of intracellular DNA isolated from HepG.2.2.15 cells after 6-day treatment with different concentrations of Helioxanthin and 22. Both integrated and replicated HBV DNA forms were detected and indicated in the figure. Every concentration was done in duplicate. The mean value at each concentration is plotted on the graph. All the bands were quantified using a Molecular Dynamics Densitometer and normalized by the intensity of the integrated band.

FIG. 3 shows that helioxanthin and 22 also have anti-HBV activity against lamivudine-resistant HBV. W10 (A) and DM2 (B) cells were treated with these two drugs and lamivudine for 6 days. Medium were collected, processed and then underwent real-time PCR. All the values were normalized by determination of β-actin levels. The error bars indicate the standard levels.

Figure 4A:
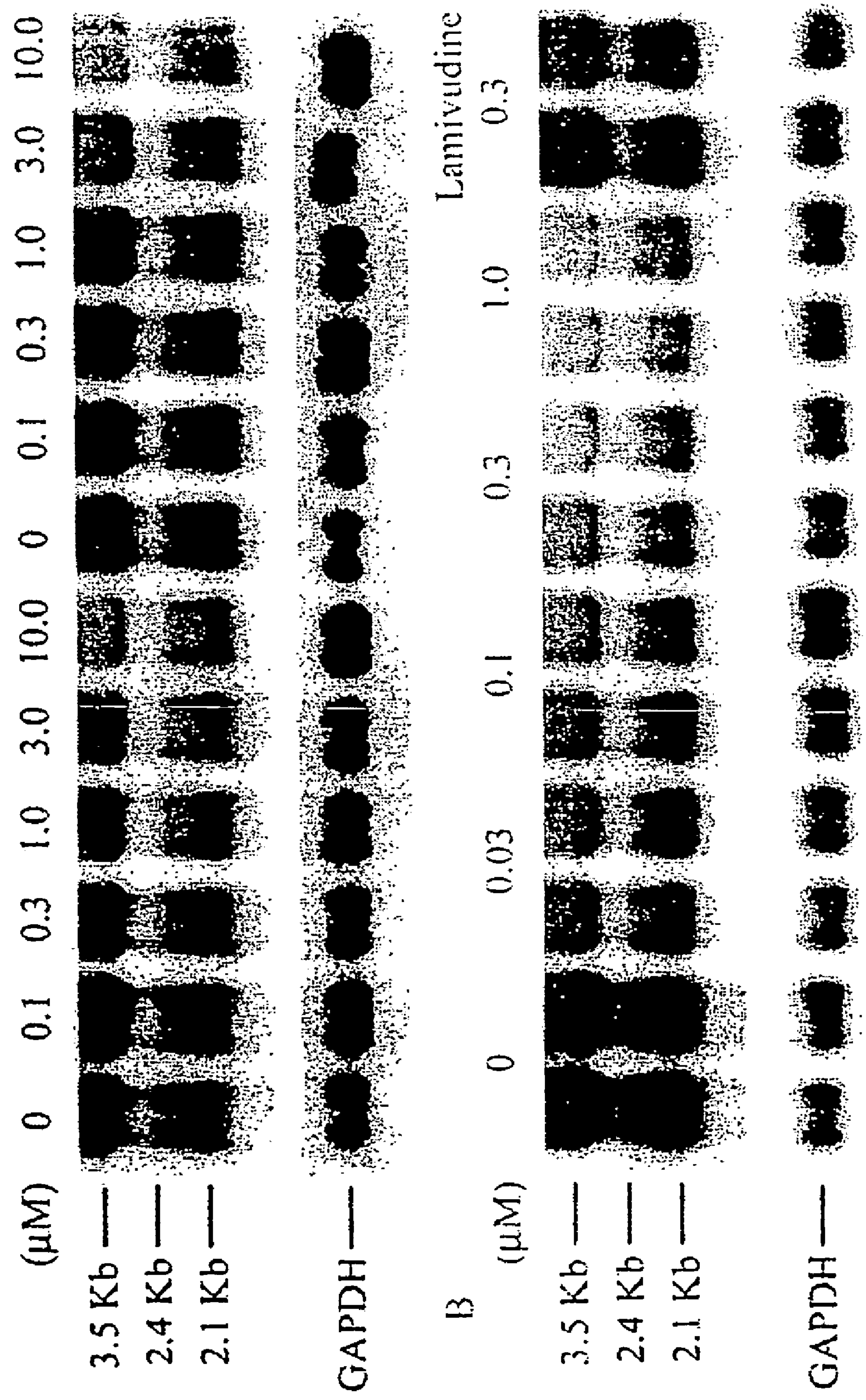

FIG. 4 shows HBV 3.5 kb, 2.4/2.1 kb transcripts were also decreased by helioxanthin (A) and 22 (B). The figure shows the Northern blot hybridization of total cellular RNA in HepG2.2.15 cells treated with various concentrations of helioxanthin and 22. Every concentration was done in duplicate. The last two lanes in (B) are lamivudine control.

Figure 5:
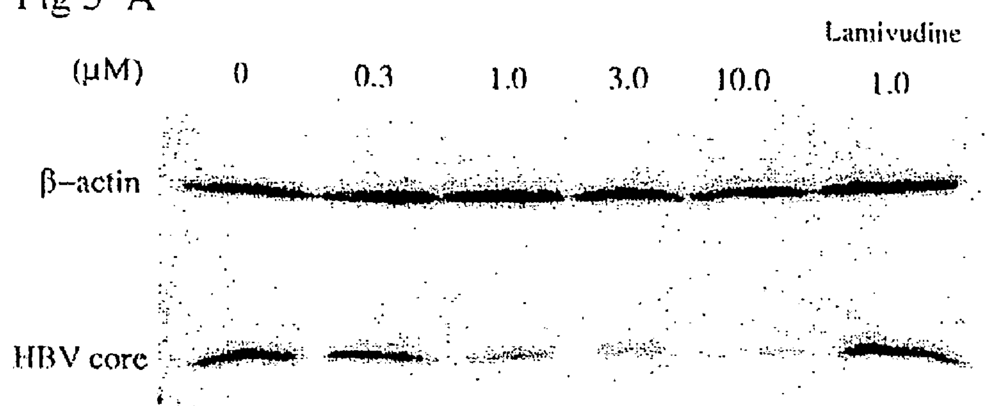
Figure 5:
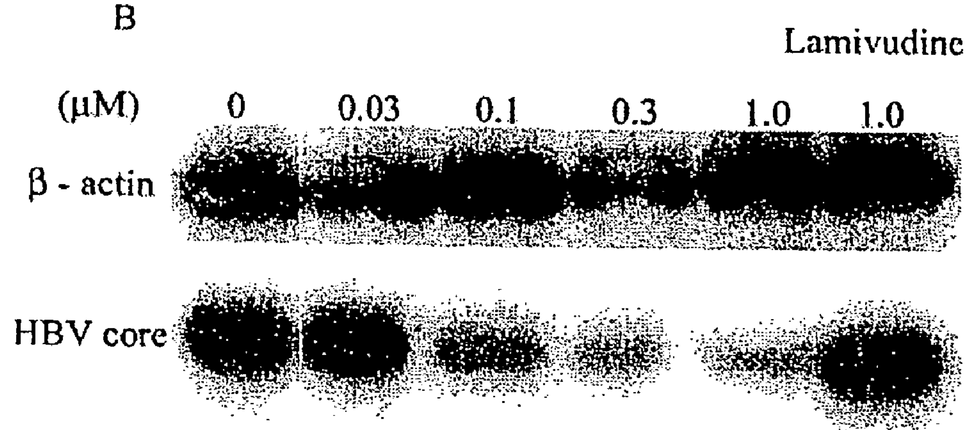

FIG. 5 shows HBV core protein expression was decreased by helioxanthin (A) and 22 (B) treatment in HepG2.2.15 cells via Western blot analysis of HepG2.2.215 cells treated with helioxanthin (A) and 22 for 6 days, using a mouse anti-HBV core antibody.

Figure 6:
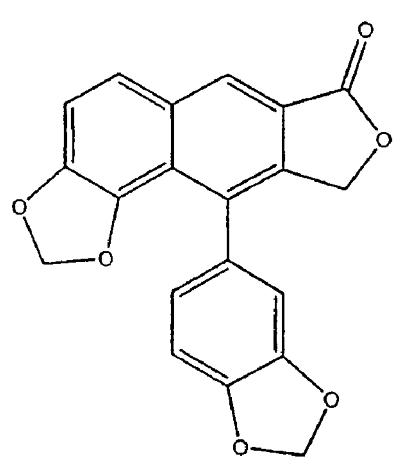
Figure 6:
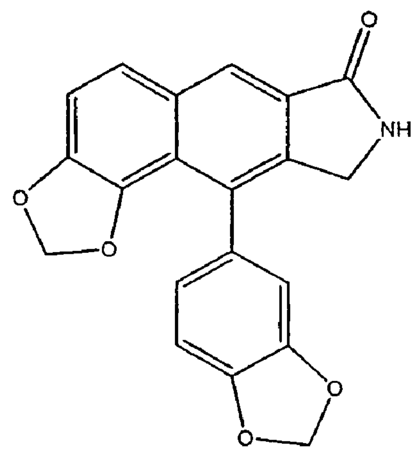

FIG. 6 shows the structure of helioxanthin and 22.

DEFINITIONS

The following definitions will be used throughout the specification to describe the present invention.

The terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

The term "compound" refers to any specific chemical compound disclosed herein. Within its use in context, the term generally refers to a single compound, but in certain instances may also refer to stereoisomers and other positional isomers and/or optical isomers (including racemic mixtures) of disclosed compounds. The compounds of this invention include all stereoisomers where relevant (e.g., cis and trans isomers) and all optical isomers of the present compounds (e.g., R and S enantiomers), as well as racemic, diastereomeric and other mixtures of such isomers, as well as all polymorphs of the present compounds, where applicable.

As defined herein "isolated" refers to material removed from its original environment and is thus, "by the hand of man" from its natural state. As defined herein, an "isolated" compound is a compound essentially free of other compounds, e.g., at least about 90% pure by weight of desired compound, preferably about 95% pure, weight of the desired compound, more preferably at least about 97-98% by weight of the desired compound and even more preferably about 99+% by weight of the desired compound. Pure compounds according to the present invention, are distinguished from compounds which may be found in their natural state, for example, as the metabolic products of biosynthesis by living organisms. Pure compounds include those natural products which have been isolated from a plant or other organism and are in a form which is used to deliver active compound for the treatment of a virus.

The term "pharmaceutically acceptable salt" is used throughout the specification to describe a salt form of the compound of the present invention described herein which are presented to increase the solubility of the compound in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts are particularly preferred as neutralization salts of carboxylic acids.

The term "pharmaceutically acceptable derivative" is used throughout the specification to describe any pharmaceutically acceptable prodrug form (such as an ester or other prodrug group) which, upon administration to a patient, provides directly or indirectly the present compound or an active metabolite of the present compound.

The term "compound" is used herein to refer to any specific chemical compound disclosed herein. Within its use in context, the term generally refers to a single compound, but in certain instances may also refer to stereoisomers and/or optical isomers (including racemic mixtures) of disclosed compounds.

The term "aryl" is used to generally describe a substituted or unsubstituted monovalent aromatic radical having a single ring (e.g., phenyl) or multiple condensed rings (e.g., naphthyl).

The term "modulate" is used to mean alter the amount or rate of for example a biological event such as viral replication.

The term "$C_{1-6}$ alkyl" denotes a straight or branched, saturated hydrocarbon chain having from one to six carbon atoms.

$C_{1-6}$ alkyl groups include, but are not limited to, methyl, ethyl, n-propyl, iso-propyl, n-butyl, iso-butyl, sec-butyl, tert-butyl, n-pentyl, iso-pentyl, 2-methylbutyl, 3-methylbutyl, n-hexyl, iso-hexyl, 4-methylpentyl, neopentyl, 2,2-dimethylpropyl and the like.

The term "acyl" is used throughout the specification to describe a group at the 5' position of the nucleoside analog (i.e., at the free hydroxyl position in the dioxolanyl moiety) which contains a $C_1$ to $C_{20}$ linear, branched, aromatic or cyclic alkyl (e.g., cyclopentyl, cyclohexyl) chain. The acyl group on various positions of the present compounds, in combination with the hydroxyl group to which is generally bound, results in an ester, which, after administration, may be cleaved to produce the free hydroxyl group. Acyl groups according to the present invention are represented by the structure:

$$RC(=O)—$$

where R is a $C_1$ to $C_{20}$ linear, branched, aromatic or cyclic alkyl chain, alkoxyalkyl, aryloxyalkyl, such as phenoxymethyl, aryl, alkoxy, among others. Preferred acyl groups are those where R is $C_1$ to $C_7$. Acyl groups according to the present invention also include, for example, those acyl groups derived from benzoic acid and related acids, 3-chlorobenzoic acid, succinic, capric and caproic, lauric, myristic, palmitic, stearic and oleic, among numerous others including mesylate groups. One of ordinary skill in the art will recognize the acyl groups that will have utility in the present invention, either to synthesize the target pharmaceutical compounds or as prodrug of the nucleosides according to the present invention.

DETAILED DESCRIPTION OF THE INVENTION

The compound of the present invention has the formula:

I

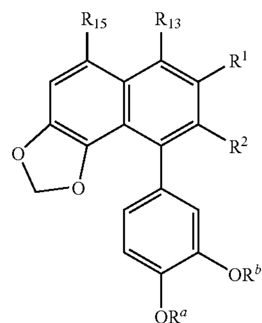

Where $R^1$ and $R^2$ are independently $C_1$-$C_6$ alkyl, COO—Na+,

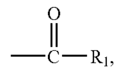

a —$(CH_2)_n$aryl, —$(CH_2)_n$Z-($C_1$-$C_6$)alkyl, —$(CH_2)_n$Z-$(CH_2)_n$aryl, each of which groups may be optionally substituted with one or more halogens, OH, COOH, $C_1$-$C_3$ alkyl or CN, or $R^1$ and $R^2$ is independently a —$(CH_2)_n NR^3R^4$ group, or $R^1$ and $R^2$ together with the adjacent benzene ring form a 5- or 6-membered heterocyclic ring according to the structure:

Ia $$\text{cyclic: } -X^1-Y-X^2-$$

where Y is O, a N—$R^{6a}$ group or a —N($R^7$)—N($R^8$)— group; $X^1$ and $X^2$ are independently a $CH_2$ or C═O group;

$R_1$ is OH, a —($C_1$-$C_6$)allyl, a —$(CH_2)_n$aryl, a —$(CH_2)_n$Z-($C_1$-$C_6$)allyl, a —$(CH_2)_n$Z-$(CH_2)_n$aryl each of which groups may be optionally substituted with one or more halogens, OH, COOH, $C_1$-$C_3$ alkyl or CN, or $R_1$ is a —$(CH_2)_n NR^5R^6$ group, $R^3$ and $R^4$ are independently selected from H, —($C_1$-$C_6$) alkyl or a

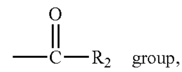

where $R_2$ is H, a —($C_1$-$C_6$)alkyl, a —$(CH_2)_n$aryl, —$(CH_2)_j$O—($C_1$-$C_6$)alkyl or a —$(CH_2)_j$O—$(CH_2)_n$aryl;

$R^5$ and $R^6$ are independently selected from H, —($C_1$-$C_4$) alkyl, —$(CH_2)_n$aryl, —$(CH_2)_j$O—($C_1$-$C_6$)alkyl or —$(CH_2)_j$O—$(CH_2)_n$aryl;

$R^{6a}$ is H, a $C_1$-$C_6$ alkyl optionally substituted with a hydroxyl group or aryloxy group, —$OR^9$ or N—$R^{10}$;

$R^7$, $R^8$, and $R^9$ are independently H or a $C_1$-$C_6$ alkyl group which may be optionally substituted with a hydroxyl group; $R^{10}$ is H, —($C_1$-$C_6$)alkyl or —C(═O)($C_1$-$C_6$)alkyl;

Z is O or NH; $R_{13}$ is H, OH, —O($C_1$-$C_4$)alkyl, ($C_1$-$C_4$) alkyl;

$R_{15}$ is H, OH, —O($C_1$-$C_4$)alkyl, ($C_1$-$C_4$) alkyl, F, Cl, Br or I;

$R^a$ and $R^b$ are independently a —($C_1$-$C_6$)alkyl, or together form a —$(CH_2)_k$— group;

j is 1, 2, 3, 4 or 5, k is 1 or 2; and n is 0, 1, 2, 3, 4 or 5;

with the proviso that when Y is O, $R_{15}$ is Cl, Br or I and when $R^1$ and $R^2$ is COOH, $R_{15}$ is Cl, or, I or their anomers, pharmaceutically acceptable salts, solvates, or polymorphs thereof.

In one specific embodiment, $R^1$ and $R^2$ are independently $C_1$-$C_6$ alkyl and

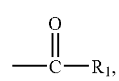

where $R_1$ is OH, a —$(CH_2)_n$Z-($C_1$-$C_6$)alkyl, a —$(CH_2)_n$Z-$(CH_2)_n$aryl each of which groups may be optionally substituted with one or more halogens, OH, COOH, $C_1$-$C_3$ alkyl or CN, Z is O or NH, n is 0, 1, 2, 3, 4 or 5, $R^a$ and $R^b$ are independently —O($C_1$-$C_6$)alkyl, or together form a —$(CH_2)_k$— group; j is 1, 2, 3, 4 or 5, k is 1 or 2; and $R_{13}$ and $R_{15}$ are H.

In another embodiment, $R^1$ and $R^2$ are

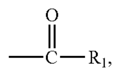

where $R^1$ is OH, a —$(CH_2)_n NR^3R^4$ group, wherein n is 0, 1, 2, 3, 4 or 5 and $R^3$ and $R^4$ are independently selected from H, —$(C_1$-$C_6)$ alkyl or a

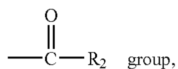

where $R_2$ is H, a —$(C_1$-$C_6)$alkyl, a —$(CH_2)_n$aryl, —$(CH_2)_j$O—$(C_1$-$C_6)$alkyl or a —$(CH_2)_j$O—$(CH_2)_n$aryl; $R^a$ and $R^b$ are independently a —$(C_1$-$C_6)$alkyl and $R_{13}$ and $R_{15}$ are H.

In yet another embodiment, $R^1$ and $R^2$ are

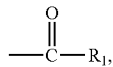

where $R_1$ is OH, $NH_2$, a —$(CH_2)_n$Z-$(C_1$-$C_6)$alkyl, wherein Z is O and n is 0, 1, 2, 3, 4 or 5 $R^a$ and $R^b$ together form a —$(CH_2)_k$— group, wherein k is 1 or 2 and $R_{13}$ and $R_{15}$ are H.

In yet another embodiment, $R^1$ and $R^2$ together with the adjacent benzene ring form a 5- or 6-membered heterocyclic ring according to the structure:

where Y is O, a N—$R^{6a}$ group or a —N($R^7$)—N($R^8$)— group; $X^1$ and $X^2$ are independently a $CH_2$ or C═O group; $R^{6a}$ is H, a $C_1$-$C_6$ alkyl optionally substituted with a hydroxyl group, —$OR^9$ or N—$R^{10}$; $R^7$, $R^8$, and $R^9$ are independently H or a $C_1$-$C_6$ alkyl group which may be optionally substituted with a hydroxyl group; $R^{10}$ is H, —$(C_1$-$C_6)$alkyl or —C(═O)$(C_1$-$C_6)$alkyl; $R_{13}$ and $R^{15}$ are H; $R^a$ and $R^b$ are independently a —$(C_1$-$C_6)$alkyl, or together form a —$(CH_2)_k$— group k is 1 or 2.

In another embodiment, the compound of the present invention has the formula:

V

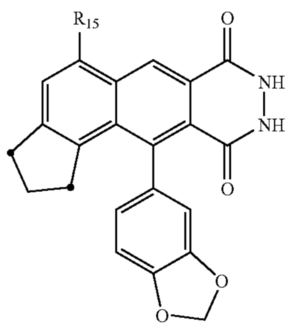

In a more specific embodiment, the compound may be selected from at least one of the group consisting of: 9-benzo[1,3]dioxol-5-yl-8-benzyloxymethyl-naphtho[1,2-d][1,3]dioxole-7-carboxylic acid benzyl ester; 9-benzo[1,3]dioxol-5-yl-8-benzyloxymethyl-naphtho[1,2-d][1,3]dioxole-7-carboxylic acid 3-benzyloxy-propyl ester; 9-benzo[1,3]dioxol-5-yl-8-methyl-naphtho[1,2-d][1,3]dioxole-7-carboxylic acid 3-hydroxy-propyl ester; 9-benzo[1,3]dioxol-5-yl-8-benzyloxymethyl-naphtho[1,2-d][1,3]dioxole-7-carboxylic acid (3-benzyloxy-propyl)-amide; 10-benzo[1,3]dioxol-5-yl-1,3-dioxa-8-aza-dicyclopenta[a,g]naphthalene-7,9-dione; 9-benzo[1,3]dioxol-5-yl-7-carbamoyl-naphtho[1,2-d][1,3]dioxole-8-carboxylic acid; 10-benzo[1,3]dioxol-5-yl-8-(3-benzyloxy-propyl)-1,3-dioxa-8-aza-dicyclopenta[a,g]naphthalene-7,9-dione; 10-(3,4-dimethoxy-phenyl)-1,3-dioxa-8-aza-dicyclopenta[a,g]naphthalene-7,9-dione; 7-carbamoyl-9-(3,4-dimethoxy-phenyl)-naphtho[1,2-d][1,3]dioxole-8-carboxylic acid; 9-benzo[1,3]dioxol-5-yl-7-methylcarbamoyl-naphtho[1,2-d][1,3]dioxole-8-carboxylic acid; 9-Benzo[1,3]dioxol-5-yl-7-dimethylcarbamoyl-naphtho[1,2-c][1,3]dioxole-8-carboxylic acid; 10-benzo[1,3]dioxol-5-yl-7,8-dihydro-1,3-dioxa-8-aza-dicyclopenta[a,g]naphthalen-9-one; 10-benzo[1,3]dioxol-5-yl-8,9-dihydro-1,3-dioxa-8-aza-dicyclopenta[a,g]naphthalen-7-one; 10-benzo[1,3]dioxol-5-yl-8-methyl-7,8-dihydro-1,3-dioxa-8-aza-dicyclopenta[a,g]naphthalen-9-one; 10-benzo[1,3]dioxol-5-yl-8-methyl-8,9-dihydro-1,3-dioxa-8-aza-dicyclopenta[a,g]naphthalen-7-one; 10-benzo[1,3]dioxol-5-yl-8-(3-benzyloxy-propyl)-8,9-dihydro-1,3-dioxa-8-aza-dicyclopenta[a,g]naphthalen-7-one; 10-benzo[1,3]dioxol-5-yl-8-(3-hydroxy-propyl)-8,9-dihydro-1,3-dioxa-8-aza-dicyclopenta[a,g]naphthalen-7-one; 10-(3,4-dimethoxy-phenyl)-8,9-dihydro-1,3-dioxa-8-aza-dicyclopenta[a,g]naphthalen-7-one; 10-benzo[1,3]dioxol-5-yl-7-methoxy-1,3-dioxa-8-aza-dicyclopenta[a,g]naphthalen-9-one; 10-benzo[1,3]dioxol-5-yl-8-hydroxy-1,3-dioxa-8-aza-dicyclopenta[a,g]naphthalene-7,9-dione; N-(10-benzo[1,3]dioxol-5-yl-7,9-dioxo-7,9-dihydro-1,3-dioxa-8-aza-dicyclopenta[a,g]naphthalen-8-yl)-acetamide (25 N-(10-Benzo[1,3]dioxol-5-yl-7-oxo-7,9-dihydro-1,3-dioxa-8-aza-dicyclopenta[a,g]naphthalen-8-yl)-acetamide; N-(10-benzo[1,3]dioxol-5-yl-9-oxo-7,9-dihydro-1,3-dioxa-8-aza-dicyclopenta[a,g]naphthalen-9-yl)-acetamide; 11-benzo[1,3]dioxol-5-yl-8,9-dihydro-1,3-dioxa-8,9-diaza-cyclopenta[a]anthracene-7,10-dione; 10-benzo[1,3]dioxol-5-yl-8-(3-hydroxy-propyl)-1,3-dioxa-8-aza-dicyclopenta[a,g]naphthalene-7,9-dione; 9-benzo[1,3]dioxol-5-yl-naphtho[1,2-d][1,3]dioxole-7,8-dicarboxylic acid dimethyl ester; 9-benzo[1,3]dioxol-5-yl-6-hydroxy-naphtho[1,2-d][1,3]dioxole-7,8-dicarboxylic acid diethyl ester; 9-benzo[1,3]dioxol-5-yl-6-methoxy-naphtho[1,2-d][1,3]dioxole-7,8-dicarboxylic acid diethyl ester; 9-benzo[1,3]dioxol-5-yl-naphtho[1,2-d][1,3]dioxole-7,8-dicarboxylic acid diamide; 10-benzo[1,3]dioxol-5-yl-5-chloro-9H-furo[3',4':6,7]naphtho[1,2-d][1,3]dioxol-7-one; 10-benzo[1,3]dioxol-5-yl-5-bromo-9H-furo[3',4':6,7]naphtho[1,2-d][1,3]dioxol-7-one; 10-benzo[1,3]dioxol-5-yl-5-iodo-9H-furo[3',4':6,7]naphtho[1,2-d][1,3]dioxol-7-one; 10-benzo[1,3]dioxol-5-yl-5-bromo-8,9-dihydro-1,3-dioxa-8-aza-dicyclopenta[a,g]naphthalen-7-one; 11-benzo[1,3]dioxol-5-yl-5-chloro-8,9-dihydro-1,3-dioxa-8,9-diaza-cyclopenta[a]anthracene-7,10-dione; 11-benzo[1,3]dioxol-5-yl-5-bromo-8,9-dihydro-1,3-dioxa-8,9-diaza-cyclopenta[a]anthracene-7,10-dione; 11-benzo[1,3]dioxol-5-yl-5-iodo-8,9-dihydro-1,3-dioxa-8,9-diaza-cyclopenta[a]anthracene-7,10-dione; 9-benzo[1,3]dioxol-5-yl-5-chloro-8-hydroxymethyl-naphtho[1,2-d][1,3]dioxole-7-carboxylic acid monosodium salt; 9-benzo[1,3]dioxol-5-yl-8-hydroxyethyl-5-iodo-naphtho[1,2-c][1,3]dioxole-7-carboxylic acid monosodium salt.

In a more specific embodiment, the compounds are 10-(3,4-dimethoxy-phenyl)-8,9-dihydro-1,3-dioxa-8-aza-dicyclopenta[a,g]naphthalen-7-one and N-(10-Benzo[1,3]dioxol-5-yl-7-oxo-7,9-dihydro-1,3-dioxa-8-aza-dicyclopenta[a,g]naphthalen-8-yl)-acetamide (26), N-(10-Benzo[1,3]dioxol-5-yl-9-oxo-7,9-dihydro-1,3-dioxa-8-aza-dicyclopenta[a,g]naphthalen-8-yl)-acetamide.

Synthesis

During chemical synthesis of the various compositions according to the present invention, one of ordinary skill in the art will be able to practice the present invention without engaging in undue experimentation. In particular, one of ordinary skill in the art will recognize the various steps that should be performed to introduce a particular substituent at the desired position of the naphthalene group or benzene ring, following the specific teachings of the present invention and well-know principles of aromatic chemistry. These steps are well-known in the art. In addition, chemical steps which are taken to "protect" functional groups such as hydroxyl or amino groups, among others, as well as "de-protect" these same functional groups, will be recognized as appropriate within the circumstances of the syntheses. A large number of protecting groups may be used in the present invention. In the case of the introduction of any one or more acyl groups onto a hydroxyl group, standard techniques, well known by those of ordinary skill, may be used. Synthesis of other prodrug forms of the present compounds may also be synthesized by well-known methods in the art.

In general, by way of example, the compounds according to the present invention may be synthesized generally by following the schemes set forth in FIGS. 1A, 1B, 1C and 1D, with modifications well known by those of ordinary skill, where appropriate. The compounds according to formulas I and II of the present invention may be advantageously synthesized according to the schemes set forth in FIG. 1A-1D, with analogous modifications from the other schemes presented, where appropriate. The compounds according to formula III and IV may be advantageously synthesized according to the scheme set forth in FIG. 1B, with analogous modifications, where appropriate. The compounds according to formula V may be advantageously synthesized according to the scheme set forth in 1C, with analogous modifications, where appropriate.

In a specific embodiment, the compound of the present invention has the structure (II)

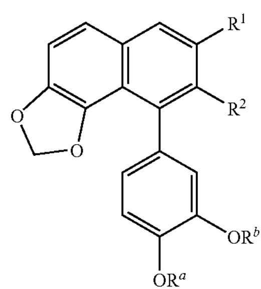

Where $R^1$ and $R^2$ together with the adjacent benzene ring form a 5- or 6-membered heterocyclic ring according to the structure Ia:

where Y is an N—$R^{6a}$ group; $R^{1a}$ is H, a $C_1$-$C_6$ alkyl optionally substituted with a hydroxyl group, —$OR^9$ or N—$R^{10}$; $R^9$ is H or a $C_1$-$C_6$ alkyl group which may be optionally substituted with a hydroxyl group; $R^{10}$ is H, —($C_1$-$C_6$)alkyl or —C(═O)($C_1$-$C_6$)alkyl; $X^1$ and $X^2$ are independently a $CH_2$ or C═O group; $R^a$ and $R^b$ are independently a —($C_1$-$C_6$) alkyl, or together form a —$(CH_2)_k$— group; k is 1 or 2.

Compound II may be obtained by reacting a compound having the formula

III

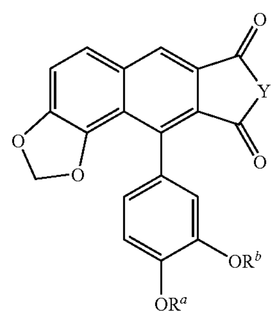

Where $R^1$ and $R^2$ together with the adjacent benzene ring form a 5- or 6-membered heterocyclic ring according to the structure Ia:

wherein Y is an N—$R^{6a}$ group; $R^{6a}$ is H, a $C_1$-$C_6$ alkyl optionally substituted with a hydroxyl group, —$OR^9$ or N—$R^{10}$; $R^9$ is H or a $C_1$-$C_6$ alkyl group which may be optionally substituted with a hydroxyl group; $R^{10}$ is H, —($C_1$-$C_6$)alkyl or —C(═O)($C_1$-$C_6$)alkyl; $R^a$ and $R^b$ are independently a —($C_1$-$C_6$)alkyl, or together form a —$CH_2)_k$— group; k is 1 or 2 with a reducing agent (sodium borohydride at O° C.). A compound encompassed by formula II may be isolated using procedures known in the art including but not limited to column chromatography, precipitation, crystallization for solids, or distillation or molecular vacuum distillation in the case where the derivatives are oils.

In a particular embodiment, $R^a$ and $R^b$ together form a —$(CH_2)_k$— group and Y is NHAc. This compound may be obtained by reacting a compound (IV) with hydrazine hydrate in acetic acid under reflux conditions for 24 hours.

IV

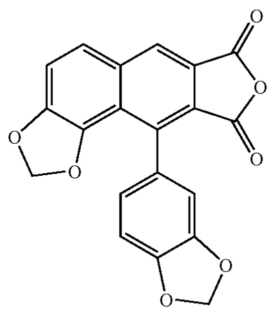

In another embodiment Y is an N—$R^{6a}$ group; $R^{6a}$ is H, a $C_1$-$C_6$ alkyl optionally substituted with a hydroxyl group or aryloxy group, $R^a$ and $R^b$ form a —$(CH_2)_k$— group; k is 1. This compound may be obtained by a Diels Alder reaction of a hydroxy acetal with maleimide to obtain an imide and subsequently reducing said imide.

In yet another embodiment, the compound of the present invention has the formula

V

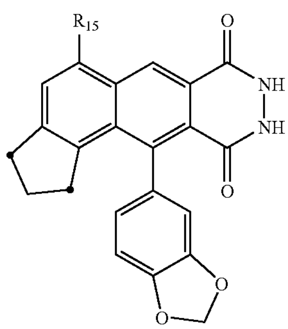

Wherein $R_{15}$ is H, I and Br. This compound may be obtained following the scheme in FIG. 1C by reacting a compound of Formula IV with hydrazine hydrate in acetic acid under reflux conditions for 24 hours. We then treat the resulting compound with zinc in acetic acid to get a rearranged and deacetylated product of Formula V. If $R_{15}$ is halogenated (e.g. Br or I), the compound is made from the rearranged and deacetylated product of Formula V using N-halo succinimide in acetonitrile or THF with acid catalyst at reflux for 24-48 hours according to scheme 1E.

Compositions and Uses

Compounds of the present invention find particular use in combating viral infections which afflict animals, and in particular, humans suffering from hepadnaviruses, e.g., Hepatitis B virus (HBV), flaviviruses, including but not limited to Hepatitis C virus (HCV), Yellow Fever virus, Dengue Virus, Japanese Encephalitis and West Nile virus, herpesviruses, including but not limited to Herpes Simplex Virus 1, Herpes Simplex Virus 2, Epstein Barr Virus, cytomegalovirus, human immunodeficiency virus (e.g., HIV-1 or HIV-2) and their complications. In particular, the compounds of the present invention may be used to treat or prevent 3TC-resistant viral infections (e.g., 3TC resistant HBV). Compounds according to the present invention offer great potential as therapeutic agents against a number of disease states for which there presently are few real therapeutic options. The compounds according to the present invention may be used alone or in combination with agents or other therapeutic treatments.

The present invention also relates to methods for modulating the replication or growth of hepadnaviruses, e.g., Hepatitis B virus (HBV), flaviviruses, including but not limited to Hepatitis C virus (HCV), Yellow Fever virus, Dengue Virus, Japanese Encephalitis and West Nile virus, herpesviruses, including but not limited to Herpes Simplex Virus 1, Herpes Simplex Virus 2, Epstein Barr Virus, cytomegalovirus, human immunodeficiency virus (e.g., HIV-1 or HIV-2) comprising exposing the virus to an inhibitory effective amount or concentration of at least one of the disclosed nucleoside analogs. This method may be used in comparison tests such as assays for determining the activities of related anti-viral compounds as well for determining the susceptibility of a patient's viral infection to one of the compounds according to the present invention.

In a related aspect, the present invention relates to methods for treating or preventing (i.e., reducing the likelihood of infection from) hepadnaviruses, e.g., Hepatitis B virus (HBV), flaviviruses, including but not limited to Hepatitis C virus (HCV), Yellow Fever virus, Dengue Virus, Japanese Encephalitis and West Nile virus, herpesviruses, including but not limited to Herpes Simplex Virus 1, Herpes Simplex Virus 2, Epstein Barr Virus, cytomegalovirus, human immunodeficiency virus (e.g., HIV-1 or HIV-2), comprising administering anti-viral effective amounts of one or more of the compounds according to the present invention to inhibit the growth or replication of the virus in the animal or human patient being treated. In a preferred method aspect according to the present invention, the present compositions are used to prevent or delay the onset of hepadnaviruses, e.g., Hepatitis B virus (HBV), flaviviruses, including but not limited to Hepatitis C virus (HCV), Yellow Fever virus, Dengue Virus, Japanese Encephalitis and West Nile virus, herpesviruses, including but not limited to Herpes Simplex Virus 1, Herpes Simplex Virus 2, Epstein Barr Virus, cytomegalovirus, human immunodeficiency virus (e.g., HIV-1 or HIV-2) infections or related conditions or viral complications in a patient, especially including hepatoma in those patients who have been infected with HBV or HCV.

Compositions, particularly pharmaceutical compositions, based upon these novel chemical compounds, comprise one or more of the above-described compounds in a therapeutically effective amount for treating a viral, generally, a hepadnaviruses, e.g., Hepatitis B virus (HBV), flaviviruses, including but not limited to Hepatitis C virus (HCV), Yellow Fever virus, Dengue Virus, Japanese Encephalitis and West Nile virus, herpesviruses, including but not limited to Herpes Simplex Virus 1, Herpes Simplex Virus 2, Epstein Barr Virus, cytomegalovirus, human immunodeficiency virus (e.g., HIV-1 or HIV-2), optionally in combination with a pharmaceutically acceptable additive, carrier or excipient.

The compounds according to the present invention, in pharmaceutical dosage form, also may be used as prophylactic agents for inhibiting the growth or replication of hepadnaviruses, e.g., Hepatitis B virus (HBV), flaviviruses, including but not limited to Hepatitis C virus (HCV), Yellow Fever virus, Dengue Virus, Japanese Encephalitis and West Nile virus, herpesviruses, including but not limited to Herpes Simplex Virus 1, Herpes Simplex Virus 2, Epstein Barr Virus, cytomegalovirus, human immunodeficiency virus (e.g., HIV-1 or HIV-2). These may be particularly appropriate as anti-viral agents. In certain pharmaceutical dosage forms, the pro-drug form, for example, an acylated form of the compound to promote dissolution, absorptivity or bioavailability may be preferred.

While not being limited by way of theory, it is believed that compounds according to the present invention exhibit their anti-viral activity by virtue of their ability to decrease viral RNA, which leads to a decrease in viral RNA, the expression of the viral gene, a decrease in antigen expression and viral replication. It is unexpected that the present compounds evidence exceptional activity against hepadnaviruses, e.g., Hepatitis B virus (HBV), flaviviruses, including but not limited to Hepatitis C virus (HCV), Yellow Fever virus, Dengue Virus, Japanese Encephalitis and West Nile virus, herpesviruses, including but not limited to Herpes Simplex Virus 1, Herpes Simplex Virus 2, Epstein Barr Virus, cytomegalovirus, human immunodeficiency virus (e.g., HIV-1 or HIV-2).

In contrast to other nucleotide analogs which only inhibit viral DNA synthesis, the compounds according to the present invention inhibit the virus at an early stage of the viral cycle in which the virus replicates via reverse transcription of a 3.5 kb pregenomic RNA as well as viral gene expression in virus DNA expression cells. The compounds could preferentially decrease viral RNA in cells; therefore, viral gene expression and replication could also decrease.

The present compounds are preferably used in pharmaceutical dosage form. In the pharmaceutical aspect according to the present invention, the compound according to the present invention is formulated preferably in admixture with a pharmaceutically acceptable carrier. In general, it is preferable to administer the pharmaceutical composition in orally-administrable form, but certain formulations may be administered via a parenteral, intravenous, intramuscular, transdermal, buccal, subcutaneous, suppository or other route. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, the pro-drug form of the compounds, especially including acylated (acetylated or other) and ether derivatives and various pharmaceutically acceptable salt forms of the present compounds, are preferred. One of ordinary skill in the art will recognize how to readily modify the present compounds to prodrug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

The amount of compound included within therapeutically active formulations according to the present invention is an effective amount for treating the infection or condition, in preferred embodiments, hepadnavirus, e.g., Hepatitis B virus (HBV), flavivirus, including but not limited to Hepatitis C virus (HCV), Yellow Fever virus, Dengue Virus, Japanese Encephalitis and West Nile virus, herpesvirus, including but not limited to Herpes Simplex Virus 1, Herpes Simplex Virus 2, Epstein Barr Virus, cytomegalovirus, human immunodeficiency virus (e.g., HIV-1 or HIV-2) infection. In general, a therapeutically effective amount of the present compound in pharmaceutical dosage form usually ranges from about 0.1 mg/kg to about 100 mg/kg or more, more preferably, slightly less than about 1 mg/kg to about 50 mg/kg of the patient or considerably more, depending upon the compound used, the condition or infection treated and the route of administration. In the case of HBV or HCV infections, the active compound is preferably administered in amounts ranging from about 0.5 mg/kg to about 25 mg/kg of the patient, depending upon the pharmacokinetics of the agent in the patient. This dosage range generally produces effective blood level concentrations of active compound which may range from about 0.05 to about 100 micrograms/cc of blood in the patient. For purposes of the present invention, a prophylactically or preventive effective amount of the compositions according to the present invention falls within the same concentration range as set forth above for therapeutically effective amount and is usually the same as a therapeutically effective amount.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

The active compounds or their pharmaceutically acceptable salts thereof can also be mixed with other active materials that do not impair the desired action, or with materials that supplement the desired action, such as other antivirals, or depending upon the desired target or therapy, antibiotics, antifungals, antinflammatories.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl nucleosides or phosphate ester prodrug forms of the nucleoside compounds according to the present invention.

Preferably, to treat, prevent or delay the onset of virus infections pursuant to the present invention, the compositions may be administered in oral dosage form in amounts ranging from about 250 micrograms up to about 500 mg or more at least once a day, preferably, up to four times a day. The present compounds are preferably administered orally, but may be administered parenterally, topically or in suppository form.

The compounds according to the present invention, because of their low toxicity to host cells, may advantageously be employed prophylactically to prevent or reduce the likelihood of an infection or secondary effects from hepadnavirus, e.g., Hepatitis B virus (HBV), flavivirus, including but not limited to Hepatitis C virus (HCV), Yellow Fever virus, Dengue Virus, Japanese Encephalitis and West Nile virus, herpesvirus, including but not limited to Herpes Simplex Virus 1, Herpes Simplex Virus 2, Epstein Barr Virus, cytomegalovirus and human immunodeficiency virus (e.g., HIV-1 or HIV-2) replication, infection and/or growth. This method is particularly applicable for preventing tumors in those patients with HBV (e.g., hepatoma) or HCV (e.g., hepatoma), Epstein Barr Virus (e.g., Burkitt's Lymphoma) and HHV-8 infections (e.g., sarcoma or lymphoma). In this aspect according to the present invention, the present compositions are used to prevent, reduce the likelihood or delay the onset of an hepadnavirus, e.g., Hepatitis B virus (HBV), flavivirus, including but not limited to Hepatitis C virus (HCV), Yellow Fever virus, Dengue Virus, Japanese Encephalitis and West Nile virus, herpesvirus, including but not limited to Herpes Simplex Virus 1, Herpes Simplex Virus 2, Epstein Barr Virus, cytomegalovirus, human immunodeficiency virus (e.g., HIV-1 or HIV-2) infection or a related disease such as hepatoma or Burkitt's lymphoma, in patients, among others. This prophylactic method comprises administering to a patient in need of such treatment or who is at risk for the development of a hepadnavirus, e.g., Hepatitis B virus (HBV), flavivirus, including but not limited to Hepatitis C virus (HCV), Yellow Fever virus, Dengue Virus, Japanese Encephalitis and West Nile virus, herpesvirus, including but not limited to Herpes Simplex Virus 1, Herpes Simplex Virus 2, Epstein Barr Virus, cytomegalovirus, human immunodeficiency virus (e.g., HIV-1 or HIV-2) infection or related symptoms or diseases an amount of a compound according to the present invention effective for alleviating, preventing or delaying the onset of the viral infection. In the prophylactic treatment according to the present invention, it is preferred that the antiviral compound utilized should be as low in toxicity and preferably non-toxic to the patient. It is particularly preferred in this aspect of the present invention that the compound which is used should be maximally effective against the virus and should exhibit a minimum of toxicity to the patient. In the case of the present compounds, these may be administered within the same dosage range for therapeutic treatment (i.e., about 250 micrograms up to about 500 mg or more from one to four times per day for an oral dosage form) as a prophylactic agent to prevent the proliferation of a virus infection, or to prolong the onset of a virus infection which manifests itself in clinical symptoms.

In addition, compounds according to the present invention may be administered alone or in combination with other agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

As indicated, compounds according to the present invention may be administered alone or in combination with other agents, especially including other compounds of the present invention or compounds which are otherwise disclosed as being useful for the treatment of hepadnavirus, e.g., Hepatitis B virus (HBV), flavivirus, including but not limited to Hepatitis C virus (HCV), Yellow Fever virus, Dengue Virus, Japanese Encephalitis and West Nile virus, herpesvirus, including but not limited to Herpes Simplex Virus 1, Herpes Simplex Virus 2, Epstein Barr Virus, cytomegalovirus, human immunodeficiency virus (e.g., HIV-1 or HIV-2), such as those relevant compounds and compositions which are disclosed in the following United States patents, which are incorporated by reference herein: U.S. Pat. Nos. 5,922,757; 5,830,894; 5,821,242; 5,610,054; 5,532,215; 5,491,135; 5,179,084; 4,902,720; 4,898,888; 4,880,784; 5,929,038; 5,922,857; 5,914,400; 5,922,711; 5,922,694; 5,916,589; 5,912,356; 5,912,265; 5,905,070; 5,892,060; 5,892,052; 5,892,025; 5,883,116; 5,883,113; 5,883,098; 5,880,141; 5,880,106; 5,876,984; 5,874,413; 5,869,522; 5,863,921; 5,863,918; 5,863,905; 5,861,403; 5,852,027; 5,849,800; 5,849,696; 5,847,172; 5,627,160; 5,561,120; 5631,239; 5,830,898; 5,827,727; 5,830,881, 5,837,871, 4,999,428, 5,015,739, 5,777,116, 5,684,010, 5,830,881, 5,726,174, 5,832,872, 5,929,038, 5,980,884, 5,891,874, 4,957,924, 6,323,180, among others. The compounds disclosed in the above-referenced patents may be used in combination with the present compounds for their additive activity or treatment profile against a number of viruses, including Hepatitis B virus (HBV), Hepatitis C virus (HCV), Yellow Fever virus, Dengue Virus, Japanese Encephalitis, West Nile virus and related flavivirus infections and, in certain instances, for their synergistic effects in combination with compounds of the present invention. Preferred secondary or additional compounds for use with the present compounds are those which do not inhibit Hepatitis B virus (HBV), Hepatitis C virus (HCV), Yellow Fever virus, Dengue Virus, Japanese Encephalitis, West Nile virus and related flavivirus infection by the same mechanism as those of the present invention.

EXAMPLES

Synthesis of Helioxanthin Analogs

Synthetic schemes are shown in FIGS. 1A-1E.

As shown in FIG. 1A, helioxanthin (2) was synthesized using procedure described in the literature, (Charlton et al., 1996, *J. Org. Chem.* 61:3452-3457), hydrolyzed with alkali, and then esterified with a mixture of alkali hydroxide and benzyl bromide to yield compound 4. The benzyl ester group of compound 4 was cleaved by alkaline hydrolysis to corresponding carboxylic acid, which was coupled with 3-benzyloxy-1-propanol by using 1,3-dicyclohexylcarbodiimide (DCC) and 4-dimethylaminopyridine (DMAP) to afford compound 6. Similarly, coupling of compound 5 to 3-(benzyloxy)propylamine in the presence of DCC and 1-hydroxybenzotriazole hydrate (1-HOBt) in $CH_2Cl_2$ gave compound 8.

The cyclic imides, 9 and 11, which are regarded as existing in a imide/imidol tautomeric mixtures, respectively, were prepared by the Diels-Alder reactions of hydroxyacetals and maleimide as depicted in FIG. 1B. Compounds 12 and 15, the acid-hydrolyzed products of imides 9 and 11, were also formed during the Diels-Alder reactions. The lactams 16 and 18, and 22 were prepared by the selective reduction of imides 9 and 11 with zinc dust in glacial acetic acid. Compounds 12, 16 and 18 were reacted with iodomethane in KOH/DMSO to afford their N-methylated products 13 and 14, 17, and, 19. Similarly, the reaction of imide 9 with trimethylsilyldiazomethane ($TMSCHN_2$) gave its O-methylated product 23.

The Mitsunobu reaction of benzyloxyalkylalcohol with imide 9 in the presence of diethyl azodicarboxylate (DEAD) and triphenylphosphine ($PPh_3$) in THF afforded a N-(benzyloxyalkyl)imide 10, which was selectively reduced with zinc dust in acetic acid to give a corresponding lactam, 20. The debenzylation of compound 20 with Pd/C under hydrogen atmosphere provided a N-(hydroxyalkyl)lactam 21.

The N-hydroxyimide 24 and N-(hydroxyalkyl)imide 29 were synthesized by reacting the anhydride 1 with the corresponding hydroxyamine and hydroxyalkylamine, respectively, as shown in FIG. 1C. The reaction of the anhydride 1 with hydrazine hydrate in glacial acetic acid gave a N-acetoimidoimide 25, which was converted to the cyclic hydrazide product 28 as well as the lactams 26 and 27 by reacting with zinc dust in acetic acid.

The anhydride 1 was reacted with $TMSCHN_2$ in a methanolic THF solution to give a bis-ester 30, which was hydrolyzed with KOH in MeOH to yield compounds 31 and 32 (FIG. 1D). The hydroxyacetal 1a was subjected to Diels-Alder addition with diethyl acetylenedicarboxylate (DEADC) to afford compound 33, which was converted to lactone 34 by reducing with lithium aluminum hydride (LAH). The conversion of imide 9 to the diamide 36 was performed with a mixture of concentrated ammonium hydroxide and THF at 40° C.

Treatment of compounds 2, 18 and 28 with N-halosuccinimides in the presence of a catalytic amount of concentrated sulfuric acid afforded corresponding compounds 37-43 which were selectively halogenated at the C-5 position (FIG. 1D). The 5-halolactones 37-39 were hydrolyzed with NaOH in MeOH to yield compounds 44-46.

Experimental

General Methods

All solvents and reagents were obtained from commercial suppliers and were used without purification. Unless otherwise specified, reactions were performed under a nitrogen atmosphere with exclusion of moisture. All reaction mixtures were magnetically stirred and monitored by TLC using Si250F precoated plates from J. T. Baker (0.25 mm). Flash column chromatography was performed on 32-63 D 60 Å silica gel from ICN SiliTech (ICN Biomedicals GmbH). Melting points were determined with an Electrothermal capillary melting point apparatus and are uncorrected $^1H$ NMR spectra were recorded on a Bruker AM-400 (400 MHz) or GE QE-plus 300 (300 MHz) spectrometer. Chemical shifts (δ) are reported in parts per million (ppm) using chloroform-d (δ 7.24 ppm) or DMSO-$d_6$ (2.50 ppm), and signals are reported as s (singlet), d (doublet), t (triplet), q (quartet), m (multiplet), or br s (broad singlet). All coupling constants are described in Hz. Mass spectra were conducted at the Mass Spectrometry Laboratory of the University of Illinois.

10-Benzo[1,3]dioxol-5-yl-9H-furo[3',4':6,7]naphtho[1,2-d][1,3]dioxol-7-one (2)

10-Benzo[1,3]dioxol-5-yl-furo[3',4':6,7]naphtho[1,2-d][1,3]dioxole-7,9-dione (1) was synthesized using procedure described in the literature (Charlton, J. L.; Oleschuk, C. J.; Chee, G. L. Hindered rotation in arylnaphthalene lignans. *J. Org. Chem.* 1996, 61, 3452-3457). The compound 1 (1.90 g, 5.25 mmol) in dry THF (100 mL) at 0° C. was added dropwise to a mixture of sodium borohydride (218 mg, 5.8 mmol) in dry THF (100 mL). The mixture was stirred at room temperature for 1 h and then acidified to pH 1-2 with 10% aqueous HCl solution. After stirring for 1 h, the mixture was extracted with ether (3×100 mL), concentrated in vacuo, and chromatographed using $CHCl_3$ to give a lactone 2 (1.44 g, 79%) as a pale yellow powder. mp 242-244° C.; $^1H$ NMR (DMSO-$d_6$) δ 8.56 (s, 1H, H4), 7.93 (d, 1H, H5, J=8.4 Hz), 7.50 (d, 1H, H6, J=8.4 Hz), 7.01 (d, 1H, H2', J=1.5 Hz), 6.95 (d, 1H, H5', J=8.1 Hz), 6.87 (dd, 1H, H6', J=1.5, 8.1 Hz), 6.08 (AB, 2H, 3',4'-$OCH_2O$—, Δδ=15.6 Hz, J=0.9 Hz), 5.99 (AB, 2H, 7,8-$OCH_2O$—, Δδ=6.0 Hz, J=0.9 Hz), 5.28 (s, 2H, lactone-$CH_2$—); MS (FAB, positive) m/z 349 $[M+H]^+$.

9-Benzo[1,3]dioxol-5-yl-8-hydroxymethyl-naphtho[1,2-d][1,3]dioxole-7-carboxylic acid monosodium salt (3)

1 N aqueous NaOH solution (2.9 mL) was added to the solution of 2 (100 mg, 0.29 mmol) in MeOH (10 mL). The mixture was stirred at 70° C. for 1 h. The solvent was evaporated to give a crude product, which was purified by silica gel column chromatography using $CH_2Cl_2$/MeOH (3:1, v/v) to afford 3 (110 mg, 98%) as a white powder. mp 128-130° C.; $^1H$ NMR (DMSO-$d_6$) δ 8.16 (s, 1H, H4), 7.52 (d, 1H, H5, J=8.7 Hz), 7.24 (d, 1H, H6, J=8.7 Hz), 6.88 (d, 1H, H5', J=8.4 Hz), 6.73 (s, 1H, H2'), 6.64 (d, 1H, H6', J=8.4 Hz), 6.05 (AB, 2H, 3',4'-$OCH_2O$—, Δδ=18.9 Hz), 5.79 (AB, 2H, 7,8-$OCH_2O$—, Δδ=8.4 Hz), 4.16 (s, 2H, —$CH_2OH$).

9-Benzo[1,3]dioxol-5-yl-8-benzyloxymethyl-naphtho[1,2-d][1,3]-dioxole-7-carboxylic acid benzyl ester (4)

A mixture of 3 (78 mg, 0.2 mmol) and benzyl bromide (0.38 mL, 3.2 mmol), and powdered KOH (168 mg) was heated at 140° C. for 3 h, and then cooled to room temperature. The mixture was diluted with water (100 mL) and extracted with EtOAc (3×100 mL). The extract was washed with water (3×100 mL), dried over $MgSO_4$, and concentrated in vacuo. The residue was purified by column chromatography on silica gel using $CH_2Cl_2$ to give 4 (56 mg, 51%) as a colorless liquid. $^1H$ NMR ($CDCl_3$) δ 8.27 (s, 1H, H4), 7.51 (d, 1H, H5, J=8.4 Hz), 7.23-7.44 (m, 10H, 2×$OCH_2Ph$), 7.22 (d, 1H, H6, J=8.4 Hz), 6.82 (d, 1H, H5', J=7.8 Hz), 6.77 (d, 1H, H2', J=1.5 Hz), 6.71 (dd, 1H, H6', J=1.5, 7.8 Hz), 6.05 (AB, 2H, 3',4'-$OCH_2O$—, Δδ=10.2 Hz, J=1.2 Hz), 5.84 (AB, 2H, 7,8-$OCH_2O$—, Δδ=4.8 Hz, J=1.2 Hz), 5.34 (s, 2H, 3-$COOCH_2Ph$), 4.67 (s, 2H, 2-$CH_2OCH_2Ph$), 4.32 (s, 2H, 2-$CH_2OBn$); MS (EI) m/z 546 $[M]^+$.

9-Benzo[1,3]dioxol-5-yl-8-benzyloxymethyl-naphtho[1,2-d][1,3]dioxole-7-carboxylic acid (5)

A solution of 4 (56 mg, 0.11 mmol) and NaOH (16 mg, 0.4 mmol) in MeOH/$H_2O$ (4:1, 2 mL) was heated at 70° C. for 12 h. The solvent was evaporated to dryness, and the residue was dissolved in water. The aqueous solution was acidified to pH 1-2 with 10% aqueous HCl solution and then extracted with ether (3×50 mL). The extract was washed with water and brine, and dried over $MgSO_4$. The evaporation of solvent yielded 5 (32 mg, 70%) as a white powder. mp 219-221° C.; $^1$H NMR (DMSO-$d_6$) δ 8.27 (s, 1H, H4), 7.70 (d, 1H, H5, J=8.7 Hz), 7.38 (d, 1H, H6, J=8.7 Hz), 7.17-7.25 (m, 5H, $OCH_2Ph$), 6.89 (d, 1H, H5', J=8.1 Hz), 6.79 (d, 1H, H2', J=1.5 Hz), 6.65 (dd, 1H, H6', J=1.5, 8.1 Hz), 6.06 (AB, 2H, 3',4'-$OCH_2O$—, Δδ=18.0 Hz, J=0.6 Hz), 5.85 (AB, 2H, 7,8-$OCH_2O$—, Δδ=9.3 Hz, J=0.9 Hz), 4.53 (s, 2H, 2-$CH_2OCH_2Ph$), 4.24 (s, 2H, 2-$CH_2OBn$); MS (FAB, positive) m/z 457 $[M+H]^+$.

9-Benzo[1,3]dioxol-5-yl-8-benzyloxymethyl-naphtho[1,2-d][1,3]dioxole-7-carboxylic acid 3-benzyloxy-propyl ester (6)

Compound 5 (54.8 mg, 0.12 mmol) in $CH_2Cl_2$ (2 mL) at 0° C. was added dropwise to a stirred solution of 3-benzyloxy-1-propanol (16.6 mg, 0.1 mmol), 1,3-dicyclohexylcarbodiimide (31 mg, 0.15 mmol) and 4-dimethylaminopyridine (14.6 mg, 0.12 mmol) in dry $CH_2Cl_2$ (1 mL). The mixture was stirred for 4 h at room temperature and concentrated in vacuo. The residue was chromatographed over silica gel using $CH_2Cl_2$/MeOH (50:1, v/v) to give 6 (61.2 mg, 84%) as a yellow liquid. $^1$H NMR ($CDCl_3$) δ 8.16 (s, 1H, H4), 7.47 (d, 1H, H5, J=8.7 Hz), 7.20-7.45 (m, 11H, H6+2×$OCH_2Ph$), 6.82 (d, 1H, H5', J=7.8 Hz), 6.76 (d, 1H, H2', J=1.5 Hz), 6.70 (dd, 1H, H6', J=1.5, 7.8 Hz), 6.06 (AB, 2H, 3',4'-$OCH_2O$—, Δδ=9.9 Hz, J=1.5 Hz), 5.84 (AB, 2H, 7,8-$OCH_2O$—, Δδ=4.5 Hz, J=1.5 Hz), 4.65 (s, 2H, $OCH_2Ph$), 4.53 (s, 2H, $OCH_2Ph$), 4.42 (t, 2H, 3-$COOCH_2(CH_2)_2OBn$, J=6.3 Hz), 4.35 (s, 2H, 2-$CH_2OBn$), 3.62 (t, 2H, 3-$COO(CH_2)_2CH_2OBn$, J=6.3 Hz), 2.06 (quintet, 2H, 3-$COOCH_2CH_2CH_2OBn$, J=6.3 Hz); MS (EI) m/z 604 $[M]^+$.

9-Benzo[1,3]dioxol-5-yl-8-methyl-naphtho[1,2-d][1,3]dioxole-7-carboxylic acid 3-hydroxy-propyl ester (7)

A mixture of 6 (48 mg, 0.079 mmol) and 10% Pd/C (12 mg) in dry THF (5 mL) was stirred for 14 h at room temperature under 1 atm of hydrogen. The mixture was filtered, and the filtrate evaporated at reduced pressure. The residue was purified by column chromatography on silica gel using $CH_2Cl_2$/MeOH (40:1, v/v) to yield 7 (30 mg, 93%) as a yellow oil. $^1$H NMR ($CDCl_3$) δ 8.32 (s, 1H, H4), 7.50 (d, 1H, H5, J=8.7 Hz), 7.18 (d, 1H, H6, J=8.7 Hz), 6.87 (d, 1H, H5', J=7.8 Hz), 6.72 (d, 1H, H2', J=1.5 Hz), 6.68 (dd, 1H, H6', J=1.5, 7.8 Hz), 6.05 (AB, 2H, 3',4'-$OCH_2O$—, Δδ=9.6 Hz, J=1.5 Hz), 5.83 (AB, 2H, 7,8-$OCH_2O$—, Δδ=1.5 Hz, J=1.5 Hz), 4.54 (t, 2H, 3-$COOCH_2(CH_2)_2OH$, J=6.3 Hz), 3.83 (t, 2H, 3-$COO(CH_2)_2CH_2OH$, J=6.3 Hz), 2.34 (s, 3H, 2-$CH_3$), 2.06 (quintet, 2H, 3-$COOCH_2CH_2CH_2OH$, J=6.3 Hz); MS (EI) m/z 408 $[M]^+$.

9-Benzo[1,3]dioxol-5-yl-8-benzyloxymethyl-naphtho[1,2-d][1,3]dioxole-7-carboxylic acid (3-benzyloxy-propyl)-amide (8)

A 60% sodium hydride dispersion in mineral oil (4 g, 0.1 mol) in a small portion at room temperature was added to a stirred solution of 3-amino-1-propanol (7.51 g, 0.1 mol) in THF (150 mL). The mixture was stirred for 30 min under nitrogen, and benzyl bromide (11.9 mL, 0.1 mol) was added. The mixture was stirred for 10 h at room temperature, and concentrated in vacuo. The residue was partitioned between 1 N aqueous HCl solution and $CH_2Cl_2$. The aqueous layer was adjusted to pH 10 with 10% aqueous NaOH solution, and extracted with $CH_2Cl_2$ (3×100 mL). The extract was dried over $MgSO_4$ and concentrated in vacuo. The residue was purified by silica gel column chromatography using $CH_2Cl_2$/MeOH (3:1 to 2:1, v/v) to give 3-(benzyloxy)propylamine (1.37 g, 8.3%) as a yellow oil. 1,3-Dicyclohexylcarbodiimide (14.4 mg, 0.07 mmol) in $CH_2Cl_2$ (2 mL) at 0° C. was added dropwise to a mixture of 5 (32 mg, 0.07 mmol) and 3-(benzyloxy)propylamine (11.6 mg, 0.07 mmol), and 1-hydroxybenzotriazole hydrate (9.5 mg, 0.07 mmol) in $CH_2Cl_2$ (5 mL). The reaction mixture was stirred for 18 h at room temperature and concentrated in vacuo. The residue was purified by silica gel column chromatography using $CH_2Cl_2$/MeOH (30:1, v/v) to afford 8 (36 mg, 85%) as a pale yellow liquid. $^1$H NMR ($CDCl_3$) δ 8.05 (s, 1H, H4), 7.44 (d, 1H, H5, J=8.7 Hz), 7.19-7.28 (m, 11H, H6+2×$OCH_2Ph$), 6.78-6.82 (m, 3H, H2'+H5'+H6'), 6.06 (AB, 2H, 3',4'-$OCH_2O$—, Δδ=6.9 Hz, J=1.5 Hz), 5.84 (AB, 2H, 7,8-$OCH_2O$—, Δδ=4.2 Hz, J=1.5 Hz), 4.45 (s, 4H, 2×$OCH_2Pb$), 4.38 (s, 2H, 2-$CH_2OBn$), 3.55 (m, 4H, 3-$CONHCH_2CH_2CH_2OBn$), 1.87 (quintet, 2H, 3-$CONHCH_2CH_2CH_2OBn$. J=6.3 Hz); MS (FAB, positive) m/z 604 $[M+H]^+$.

10-Benzo[1,3]dioxol-5-yl-1,3-dioxa-8-aza-dicyclopenta[a,g]naphthalene-7,9-dione (9) and 9-Benzo[1,3]dioxol-5-yl-7-carbamoyl-naphtho[1,2-d][1,3]dioxole-8-carboxylic acid (12)

The hydroxyacetal 1a (7.34 g, 21.3 mmol), maleimide (2.07 g, 21.3 mmol), acetic anhydride (7 mL), $CH_2Cl_2$ (7 mL), and glacial acetic acid (3 mL) was heated at 140° C. for 24 h. The cooled mixture was diluted with $CH_2Cl_2$ (100 mL), washed with 5% $NaHCO_3$ solution (3×100 mL), dried over $MgSO_4$, and concentrated under vacuum. The silica gel column chromatography of the crude product using $CH_2Cl_2$/acetone (30:1 to 3:1, v/v) gave two fractions. The first fraction eluted with $CH_2Cl_2$/acetone (30:1, v/v) gave a yellow solid which was then recrystallized from acetone to give an imide 9 (1.33 g, 17%). mp 306-308° C.; $^1$H NMR (DMSO-$d_6$) δ 8.61 (s, 1H, H4), 7.98 (d, 1H, H5, J=8.7 Hz), 7.62 (d, 1H, H6, J=8.7 Hz), 6.93 (d, 1H, H2', J=1.5 Hz), 6.92 (d, 1H, H5', J=7.8 Hz), 6.79 (dd, 1H, H6', J=1.5, 7.8 Hz), 6.09 (AB, 2H, 3',4'-$OCH_2O$—, Δδ=5.7 Hz), 5.99 (AB, 2H, 7,8-$OCH_2O$—, Δδ=4.5 Hz); MS (FAB, positive) m/z 362 $[M+H]^+$.

The second fraction eluted with $CH_2Cl_2$/acetone (3:1, v/v) afforded a pale yellow solid (12, 1.66 g, 21%) which was identified as the acid hydrolysis product of imide 9. mp 207-209° C.; $^1$H NMR ($CDCl_3$) δ 8.31 (s, 1H, H4), 7.62 (s, 1H, 2-COOH), 7.60 (d, 1H, H5, J=8.4 Hz), 7.27 (d, 1H, H6, J=8.4 Hz), 6.87-6.92 (m, 3H, H2'+H5'+H6'), 6.03 (s, 2H, 3',4'-$OCH_2O$—), 5.97 (s, 2H, 7,8-$OCH_2O$—); MS (FAB, positive) m/z 336 $[M-CONH_2+H]^+$.

10-Benzo[1,3]dioxol-5-yl-8-(3-benzyloxy-propyl)-1,3-dioxa-8-aza-dicycloplenta[a,g]naphthalene-7,9-dione (10)

A solution of diethyl azodicarboxylate (52 mg, 0.3 mmol) in dry THF (3 mL) was added dropwise to a stirred solution of 9 (108 mg, 0.3 mmol), 3-benzyloxy-1-propanol (50 mg, 0.3 mmol), and triphenylphosphine (79 mg, 0.3 mmol) in dry THF (6 mL) at 0° C. over 30 min. The mixture was stirred at room temperature for 30 h, and then concentrated under reduced pressure. The residue was purified by column chromatography on silica gel, eluting with n-hexane/EtOAc (2:1, v/v) to give 10 (56 mg, 37%) as a yellow powder. mp 153-155° C.;

$^1$H NMR ($CDCl_3$) δ 8.24 (s, 1H, H4), 7.66 (d, 1H, H5, J=8.4 Hz), 7.35 (d, 1H, H6, J=8.4 Hz), 7.24-7.26 (m, 5H, $OCH_2Ph$), 6.78-6.91 (m, 3H, H2'+H5'+H6'), 6.07 (AB, 2H, 3',4'-$OCH_2O$—, Δδ=15.3 Hz, J=1.5 Hz), 5.95 (AB, 2H, 7,8-$OCH_2O$—, Δδ=5.4 Hz, J=1.2 Hz), 4.45 (s, 2H, $OCH_2Ph$), 3.80 (t, 2H, $NCH_2(CH_2)_2OBn$, J=6.0 Hz), 3.54 (t, 2H, $N(CH_2)_2CH_2OBn$, J=6.0 Hz), 2.01 (quintet, 2H, $NCH_2CH_2CH_2OBn$, J=6.0 Hz); MS (EI) m/z 509 $[M]^+$.

10-(3,4-Dimethoxy-phenyl)-1,3-dioxa-8-aza-dicyclopenta[a,g]naphthalene-7,9-dione (11) and 7-Carbamoyl-9-(3,4-dimethoxy-phenyl)-naphtho[1,2-d][1,3]dioxole-8-carboxylic acid (15)

The acetal (2.25 g, 11.6 mmol) of piperonal was dissolved in dry THF (40 mL) under nitrogen, and cooled to −78° C., and n-butyllithium (1.6 M in hexanes, 7.98 mL, 12.8 mmol) was added dropwise over 30 min. The mixture was stirred for 15 min and then at 0° C. for 20 min. The mixture was again cooled to −78° C., followed by dropwise addition of 3,4-dimethoxybenzaldehyde (1.93 g, 11.6 mmol) in THF (15 mL). After stirring for 20 min, the solution was gradually warmed to room temperature and stirred for another 1.5 h, followed by the addition of water (100 mL). The resulting mixture was extracted with ether (3×100 mL), dried over $MgSO_4$, and concentrated to provide a crude hydroxyacetal 1b (4.18 g). The crude product was employed in following reaction without further purification.

The hydroxyacetal 1b (4.18 g, 11.6 mmol), maleimide (1.13 g, 11.6 mmol), acetic anhydride (4 mL), $CH_2Cl_2$ (4 mL), and glacial acetic acid (1.8 mL) were heated at 140° C. for 24 h. The cooled mixture was diluted with $CH_2Cl_2$ (100 mL), washed with 5% $NaHCO_3$ solution (3×100 mL), dried over $MgSO_4$, and concentrated in vacuo. The silica gel column chromatography of the crude product using $CH_2Cl_2$/acetone (30:1 to 3:1, v/v) gave two fractions. The first fraction eluted with $CH_2Cl_2$/acetone (30:1, v/v) gave a yellow solid which was then recrystallized from acetone to give an imide 11 (800 mg, 18%). mp 288-290° C.; $^1$H NMR (DMSO-$d_6$) δ 8.60 (s, 1H, H4), 7.98 (d, 1H, H5, J=8.7 Hz), 7.62 (d, 1H, H6, J=8.7 Hz), 6.88-6.96 (m, 3H, H2'+H5'+H6'), 5.98 (AB, 2H, 7,8-$OCH_2O$—, Δδ=3.3 Hz), 3.81, 3.68 (each s, 2×3H, 3'-$OCH_3$+4'-$OCH_3$); MS (FAB, positive) m/z 378 $[M+H]^+$.

The second fraction eluted with $CH_2Cl_2$/acetone (3:1, v/v) afforded a white solid (15, 213 mg, 5%) which was identified as the acid hydrolysis product of imide 11. mp 240-242° C.;

$^1$H NMR (DMSO-$d_6$) δ 8.42 (s, 1H, H4), 7.70 (d, 1H, H5, J=8.7 Hz), 7.41 (d, 1H, H6, J=8.7 Hz), 6.96-7.00 (m, 3H, H2'+H5'+H6'), 5.98 (s, 2H, 7,8-$OCH_2O$—), 3.79, 3.74 (each s, 2×3H, 3'-$OCH_3$+4'-$OCH_3$); MS (FAB, positive) m/z 352 $[M-CONH_2+H]^+$.

9-Benzo[1,3]dioxol-5-yl-7-methylcarbamoyl-naphtho[1,2-d][1,3]dioxole-8-carboxylic acid (13) and 9-Benzo[1,3]dioxol-5-yl-7-dimethylcarbamoyl-naphtho[1,2-d][1,3]dioxole-8-carboxylic acid (14)

Powdered KOH (64 mg, 1.1 mmol) was added to DMSO (3 mL) was added. After stirring for 5 min, compound 12 (108 mg, 0.28 mmol) was added, followed immediately by iodomethane (0.035 mL, 0.57 mmol). The mixture was stirred for 24 h and poured into water (30 mL), and then extracted with $CH_2Cl_2$ (3×30 mL). The combined organic extract was washed with water (5×30 mL), dried over $MgSO_4$, and concentrated in vacuo. The resulting product was purified by column chromatography on silica gel using $CH_2Cl_2$/acetone (10:1, v/v) to yield 13 (20 mg, 18%) as a pale yellow powder and 14 (80 mg, 71%) as a pale yellow oil, respectively. 13: mp 223-225° C.; $^1$H NMR ($CDCl_3$) δ 8.26 (s, 1H, H4), 7.60 (d, 1H, H5, J=8.7 Hz), 7.57 (s, 1H, 2-COOH), 7.25 (d, 1H, H6, J=8.7 Hz), 6.87-6.92 (m, 3H, H2'+H5'+H6'), 6.04 (s, 2H, 3',4'-$OCH_2O$—), 5.97 (s, 2H, 7,8-$OCH_2O$—), 3.07 (d, 3H, 3-$CONHCH_3$, J=4.8 Hz). 14: $^1$H NMR ($CDCl_3$) δ 7.85 (s, 1H, H4), 7.52 (d, 1H, H5, J=8.7 Hz), 7.32 (s, 1H, 2-COOH), 7.25 (d, 1H, H6, J=8.7 Hz), 6.86-6.92 (m, 3H, H2'+H5'+H6'), 6.03 (s, 2H, 3',4'-$OCH_2O$—), 5.95 (s, 2H, 7,8-$OCH_2O$—), 3.12 (s, 6H, 3-$CON(CH_3)_2$).

10-Benzo[1,3]dioxol-5-yl-7,8-dihydro-13-dioxa-8-aza-dicyclopenta[a,g]naphthalen-9-one (16) and 10-Benzo[1,3]dioxol-5-yl-8,9-dihydro-1,3-dioxa-8-aza-dicyclopenta[a,g]naphthalen-7-one (18)

Compound 9 (181 mg, 0.5 mmol) was dissolved in glacial acetic acid (5 mL) and the freshly activated zinc dust (328 mg) was added thereto, and then heated in an oil bath at 100° C. for 48 h. The insoluble solid was filtered off and the majority of acetic acid removed with a rotary evaporator. The obtained residue was neutralized to pH 7 with 10% aqueous NaOH solution, and then extracted with $CHCl_3$ (3×100 mL). The extract was washed with water, dried over $MgSO_4$, and concentrated in vacuo. The crude product was purified by column chromatography on silica gel, eluting with $CH_2Cl_2$/acetone (3:1 to 2:1, v/v) to give two fractions. The first (minor) and the second (major) fractions afforded a retro-lactam 16 (12 mg, 7%) and a lactam 18 (56 mg, 32%) as pale yellow solids, respectively. 16: Mp 267-269° C.; $^1$H NMR (DMSO-$d_6$) δ 8.48 (s, 1H, NH), 7.99 (s, 1H, H4), 7.64 (d, 1H, H5, J=8.7 Hz), 7.42 (d, 1H, H6, J=8.7 Hz), 6.83 (d, 1H, H5', J=7.8 Hz), 6.80 (d, 1H, H2', J=1.5 Hz), 6.66 (dd, 1H, H6', J=1.5, 7.8 Hz), 6.04 (AB, 2H, 3',4'-$OCH_2O$—, Δδ=3.9 Hz), 5.86 (AB, 2H, 7,8-$OCH_2O$—, Δδ=5.4 Hz), 4.38 (br s, 2H, lactam-$CH_2$—); MS (FAB, positive) m/z 348 $[M+H]^+$. 18: mp 252-254° C.; $^1$H NMR (DMSO-$d_6$) δ 8.59 (s, 1H, NH), 8.27 (s, 1H, H4), 7.83 (d, 1H, H5, J=8.7 Hz), 7.41 (d, 1H, H6, J=8.7 Hz), 6.98 (s, 1H, H2'), 6.94 (d, 1H, H5', J=7.8 Hz), 6.84 (d, 1H, H6', J=7.8 Hz), 6.07 (AB, 2H, 3',4'-$OCH_2O$—, Δδ=14.4 Hz), 5.93 (AB, 2H, 7,8-$OCH_2O$—, Δδ=6.0 Hz), 4.17 (br s, 2H, lactam-$CH_2$—); MS (FAB, positive) m/z 348 $[M+H]^+$.

10-Benzo[1,3]dioxol-5-yl-8-methyl-7,8-dihydro-1,3-dioxa-8-aza-dicyclopenta[a,g]naphthalen-9-one (17)

Powdered KOH (11.2 mg, 0.2 mmol) was added to DMSO (1 mL). After stirring for 5 min, compound 16 (18 mg, 0.05 mmol) was added, followed immediately by iodomethane (0.006 mL, 0.1 mmol). The mixture was stirred for 1 h and poured into water (15 mL), and then extracted with $CH_2Cl_2$ (3×20 mL). The combined organic extract was washed with water (5×20 mL), dried over $MgSO_4$, and then concentrated in vacuo. The residue was purified by column chromatography on silica gel using $CH_2Cl_2$/acetone (10:1, v/v) to provide 17 (12 mg, 66%) as a pale yellow powder. mp 242-244° C.; $^1H$ NMR ($CDCl_3$) δ 7.79 (s, 1H, H4), 7.50 (d, 1H, H5, J=8.4 Hz), 7.29 (d, 1H, H6, J=8.4 Hz), 6.83-6.88 (m, 3H, H2'+H5'+H6'), 6.04 (AB, 2H, 3',4'-$OCH_2O$—, Δδ=21.6 Hz, J=1.5 Hz), 5.89 (AB, 2H, 7,8-$OCH_2O$—, Δδ=2.4 Hz), 4.46 (s, 2H, lactam-$CH_2$), 3.14 (s, 3H, $NCH_3$); MS (FAB, positive) m/z 362 $[M+H]^+$.

10-Benzo[1,3]dioxol-5-yl-8-methyl-8,9-dihydro-1,3-dioxa-8-aza-dicyclopenta[a,g]naphthalen-7-one (19)

Powdered KOH (11.2 mg, 0.2 mmol) was added to DMSO (1 mL). After stirring for 5 min, compound 18 (18 mg, 0.05 mmol) was added, followed immediately by iodomethane (0.006 mL, 0.1 mmol). The mixture was stirred for 1 h and poured into water (15 mL), and then extracted with $CH_2Cl_2$ (3×20 mL). The combined organic extract was washed with water (5×20 mL), dried over $MgSO_4$, and then concentrated in vacuo. The residue was purified by column chromatography on silica gel using $CH_2Cl_2$/acetone (10:1, v/v) to give 19 (12 mg, 66%) as a pale yellow powder. mp 234-236° C.; $^1H$ NMR ($CDCl_3$) δ 8.30 (s, 1H, H4), 7.66 (d, 1H, H5, J=8.4 Hz), 7.26 (d, 1H, H6, J=8.4 Hz), 6.81-6.91 (m, 3H, H2'+H5'+H6'), 6.06 (AB, 2H, 3',4'-$OCH_2O$—, Δδ=8.4 Hz, J=1.2 Hz), 5.92 (AB, 2H, 7,8-$OCH_2O$—, Δδ=7.8 Hz, J=1.5 Hz), 4.26 (q, 2H, lactam-$CH_2$—, J=6.3 Hz), 3.18 (s, 3H, $NCH_3$); MS (EI) m/z 361 $[M]^+$.

10-Benzo[1,3]dioxol-5-yl-8-(3-benzyloxy-propyl)-8,9-dihydro-1,3-dioxa-8-aza-dicyclopenta[a,g]naphthalen-7-one (20)

Compound 10 (40 mg, 0.08 mmol) was dissolved in glacial acetic acid (3 mL) and the freshly activated zinc dust (206 mg) was added thereto, and then heated in an oil bath at 100° C. for 48 h. The insoluble solid was filtered off and the majority of acetic acid removed with a rotary evaporator. The obtained residue was neutralized to pH 7 with 10% aqueous NaOH solution, and then extracted with $CHCl_3$ (3×50 mL). The combined organic extract was washed with water (2×100 mL), dried over $MgSO_4$, and concentrated in vacuo. The crude product was chromatographed with n-hexane/EtOAc (2:1 to 1:1, v/v) to afford 20 (26 mg, 66%) as a yellow oil. $^1H$ NMR ($CDCl_3$) δ 8.30 (s, 1H, H4), 7.66 (d, 1H, H5, J=8.4 Hz), 7.28 (d, 1H, H6, J=8.4 Hz), 7.25 (br s, 5H, $OCH_2Ph$), 6.77-6.90 (m, 3H, H2'+H5'+H6'), 6.06 (AB, 2H, 3',4'-$OCH_2O$—, Δδ=9.6 Hz, J=1.2 Hz), 5.92 (AB, 2H, 7,8-$OCH_2O$—, Δδ=4.8 Hz, J=1.2 Hz), 4.47 (s, 2H, $OCH_2Ph$), 4.25 (q, 2H, q, lactam-$CH_2$—, J=6.6 Hz), 3.73 (t, 2H, $NCH_2(CH_2)_2OBn$, J=6.0 Hz), 3.56 (t, 2H, $N(CH_2)_2CH_2OBn$, J=6.0 Hz), 1.98 (quintet, 2H, $NCH_2CH_2CH_2OBn$, J=6.0 Hz); MS (EI) m/z 495 $[M]^+$.

10-Benzo[1,3]dioxol-5-yl-8-(3-hydroxy-propyl)-8,9-dihydro-1,3-dioxa-8-aza-dicyclopenta[a,g]naphthalen-7-one (21)

The mixture of 20 (16 mg, 0.032 mmol) and 10% Pd/C (4 mg) in dry THF (3 mL) was stirred for 20 h at room temperature under 1 atm of hydrogen. The Pd/C was removed by filtration, and the solvent was evaporated under reduced pressure. The residue was purified by column chromatography on silica gel using $CH_2Cl_2$/acetone (3:1 to 2:1, v/v) to yield 21 (9 mg, 69%) as a white solid. mp 213-215° C.; $^1H$ NMR ($CDCl_3$) δ 8.31 (s, 1H, H4), 7.67 (d, 1H, H5, J=8.4 Hz), 7.28 (d, 1H, H6, J=8.4 Hz), 6.82-6.92 (m, 3H, H2'+H5'+H6'), 6.07 (AB, 2H, 3',4'-$OCH_2O$—, Δδ=8.7 Hz, J=1.2 Hz), 5.93 (AB, 2H, 7,8-$OCH_2O$—, Δδ=4.8 Hz, J=1.2 Hz), 4.28 (q, 2H, lactam-$CH_2$—, J=4.8 Hz), 3.77 (t, 2H, $NCH_2(CH_2)_2OH$, J=4.8 Hz), 3.59 (t, 2H, $N(CH_2)_2CH_2OH$, J=4.8 Hz), 2.65 (br s, 1H, OH), 1.81 (quintet, 2H, $NCH_2CH_2CH_2OH$, J=4.8 Hz); MS (EI) m/z 405 $[M]^+$.

10-(3,4-Dimethoxy-phenyl)-8,9-dihydro-1,3-dioxa-8-aza-dicyclopenta[a,g]naphthalen-7-one (22)

Compound 11 (400 mg, 1.06 mmol) was dissolved in glacial acetic acid (10 mL) and the freshly activated zinc dust (695 mg) was added thereto, and then heated in an oil bath at 100° C. for 48 h. The insoluble solid was filtered off and the majority of acetic acid was removed with a rotary evaporator. The obtained residue was neutralized to pH 7 with 10% aqueous NaOH solution, and then extracted with $CHCl_3$ (3×100 mL). The extract was washed with water, dried over $MgSO_4$, and concentrated in vacuo. The crude product was purified by column chromatography on silica gel, eluting with $CH_2Cl_2$/acetone (3:1 to 2:1, v/v) to give 22 (95 mg, 25%) as a pale yellow solid. mp 258° C. (decomp.); $^1H$ NMR ($CDCl_3$) δ 8.36 (s, 1H, H4), 7.69 (d, 1H, H5, J=8.7 Hz), 7.29 (d, 1H, H6, J=8.7 Hz), 6.86-6.95 (m, 3H, H2'+H5'+H6'), 5.90 (s, 2H, 7,8-$OCH_2O$—), 4.35 (q, 2H, lactam-$CH_2$—, J=22.8 Hz), 3.99, 3.88 (each s, 2×3H, 3'-$OCH_3$+4'-$OCH_3$); MS (FAB, positive) m/z 364 $[M+H]^+$.

10-Benzo[1,3]dioxol-5-yl-7-methoxy-1,3-dioxa-8-aza-dicyclopenta[a,g]naphthalen-9-one (23)

Compound 9 (29 mg, 0.08 mmol) was dissolved in a mixture of MeOH (3 mL) and THF (6 mL). Trimethylsilyldiazomethane (2 M in hexanes, 0.2 mL, 0.4 mmol) was added to the solution. The mixture was stirred for 18 h at room temperature, and then concentrated in vacuo. The crude material was purified by column chromatography on silica gel using $CH_2Cl_2$/MeOH (30:1, v/v) to provide 23 (22 mg, 73%) as a yellow powder. mp 306-308° C.;

$^1H$ NMR ($CDCl_3$) δ 8.27 (s, 1H, H4), 7.67 (d, 1H, H5, J=8.4 Hz), 7.35 (d, 1H, H6, J=8.4 Hz), 6.83-6.92 (m, 3H, H2'+H5'+H6'), 6.07 (AB, 2H, 3',4'-$OCH_2O$—, 9Δδ=15.6 Hz, J=1.5 Hz), 5.96 (AB, 2H, 7,8-$OCH_2O$—, Δδ=4.2 Hz, J=1.5 Hz), 3.15 (s, 3H, $OCH_3$); MS (EI) m/z 375 $[M]^+$.

10-Benzo[1,3]dioxol-5-yl-8-hydroxy-1,3-dioxa-8-aza-dicyclopenta[a,g]naphthalene-7,9-dione (24)

Hydroxyamine hydrochloride (20.9 mg, 0.3 mmol) and triethylamine (0.04 mL, 0.3 mmol) were dissolved in EtOH (30 mL). After stirring for 10 min, anhydride 1 (109 mg, 0.3 mmol) was added. The mixture was refluxed overnight and then concentrated in vacuo. The resulting product was purified by silica gel column chromatography using $CH_2Cl_2$/acetone (2:1, v/v) to afford 24 (16 mg, 15%) as a yellow powder. mp 255° C. (decomp.); $^1H$ NMR (DMSO-$d_6$) δ 10.78 (s, 1H, OH), 8.40 (s, 1H, H4), 7.89 (d, 1H, H5, J=8.7 Hz), 7.54 (d, 1H, H6, J=8.7 Hz), 6.94 (s, 1H, H2'), 6.90 (d, 1H, H5', J=7.8 Hz), 6.79 (d, 1H, H6', J=7.8 Hz), 6.08 (s, 2H, 3',4'-$OCH_2O$—), 5.96 (AB, 2H, 7,8-$OCH_2O$—, Δδ=5.7 Hz); MS (FAB, positive) m/z 378 $[M+H]^+$.

N-(10-Benzo[1,3]dioxol-5-yl-7,9-dioxo-7,9-dihydro-1,3-dioxa-8-aza-dicyclopenta[a,g]naphthalen-8-yl)-acetamide (25)

A solution of anhydride 1 (145 mg, 0.4 mmol) in glacial acetic acid (10 mL) was refluxed with hydrazine hydrate (0.023 mL, 0.48 mmol) for 24 h under nitrogen and then poured, after cooling, into ice water. The resulting precipitate was filtered and dried under reduced pressure. The residue was purified by column chromatography on silica gel using $CH_2Cl_2$/MeOH (30:1 to 20:1, v/v) to give 25 (143 mg, 86%) as a yellow solid. mp 281-283° C.; $^1$H NMR ($CDCl_3$) δ 8.34 (s, 1H, H4), 7.69 (d, 1H, H5, J=8.7 Hz), 7.46 (s, 1H, NHAc), 7.38 (d, 1H, H6, J=8.7 Hz), 6.84-6.87 (m, 3H, H2'+H5'+H6'), 6.06 (AB, 2H, 3',4'-$OCH_2O$—, Δδ=16.5 Hz, J=1.5 Hz), 5.98 (AB, 2H, 7,8-$OCH_2O$—, Δδ=5.4 Hz, J=1.2 Hz), 2.17 (s, 3H, $NHCOCH_3$); MS (EI) m/z 418 $[M]^+$.

N-(10-Benzo[1,3]dioxol-5-yl-7-oxo-7,9-dihydro-1,3-dioxa-8-aza-dicyclopenta[a,g]naphthalen-8-yl)-acetamide (26). N-(10-Benzo[1,3]dioxol-5-yl-9-oxo-7,9-dihydro-1,3-dioxa-8-aza-dicyclopenta[a,g]naphthalen-8-yl)-acetamide (27) and 11-Benzo[1,3]dioxol-5-yl-8,9-dihydro-1,3-dioxa-8,9-diaza-cyclopenta[a]anthracene-7,10-dione (28)

Compound 25 (113 mg, 0.27 mmol) was dissolved in glacial acetic acid (2 mL) and the freshly activated zinc dust (196 mg) was added thereto, and then heated in an oil bath at 100° C. for 5 h. The insoluble solid was filtered off and the majority of acetic acid removed with a rotary evaporator. The obtained residue was neutralized to pH 7 with 10% aqueous NaOH solution, and then extracted with $CHCl_3$ (3×100 mL). The extract was washed with water, dried over $MgSO_4$, and concentrated in vacuo. The residue was chromatographed on silica gel using $CH_2Cl_2$/acetone (7:1 to 1:1, v/v) to afford a lactam 26 (52 mg, 48%, pale yellow powder), a retro-lactam 27 (16 mg, 15%, yellow powder), and a hydrazino compound 28 (20 mg, 20%, yellow powder), respectively. 26: mp 274-276° C.; $^1$H NMR ($CDCl_3$) δ 8.51 (s, 1H, NHAc), 8.34 (s, 1H, H4), 7.64 (d, 1H, H5, J=8.7 Hz), 7.28 (d, 1H, H6, J=8.7 Hz), 6.78-6.89 (m, 3H, H2'+H5'+H6'), 6.06 (AB, 2H, 3',4'-$OCH_2O$—, Δδ=11.1 Hz, J=1.2 Hz), 5.94 (AB, 2H, 7,8-$OCH_2O$—, Δδ=5.1 Hz, J=1.2 Hz), 4.54 (m, 2H, lactam-$CH_2$—), 2.14 (s, 3H, $NHCOCH_3$); MS (EI) m/z 404 $[M]^+$. 27: mp 278-280° C.; $^1$H NMR ($CDCl_3$) δ 8.44 (s, 1H, NHAc), 7.79 (s, 1H, H4), 7.50 (d, 1H, H5, J=8.7 Hz), 7.30 (d, 1H, H6, J=8.7 Hz), 6.74-6.84 (m, 3H, H2'+H5'+H6'), 6.02 (AB, 2H, 3',4'-$OCH_2O$—, Δδ=18.3 Hz, J=0.9 Hz), 5.89 (AB, 2H, 7,8-$OCH_2O$—, Δδ=1.2 Hz), 4.72 (s, 2H, lactam-$CH_2$—), 1.99 (s, 3H, $NHCOCH_3$); MS (EI) 72/z 404 $[M]^+$. 28: mp 318-320° C.; $^1$H NMR ($CDCl_3$) δ 9.71 (s, 1H, NH), 8.98 (s, 1H, NH), 7.93 (s, 1H, H4), 7.81 (d, 1H, H5, J=8.7 Hz), 7.43 (d, 1H, H6, J=8.7 Hz), 6.93 (d, 1H, H5', J=7.8 Hz), 6.86 (d, 1H, H2', J=1.2 Hz), 6.82 (dd, 1H, H6', J=1.2, 7.8 Hz), 6.11 (AB, 2H, 3',4'-$OCH_2O$—, Δδ=9.4 Hz, J=1.2 Hz), 5.97 (AB, 2H, 7,8-$OCH_2O$—, Δδ=6.3 Hz, J=1.2 Hz); MS (EI) m/z 376 $[M]^+$.

10-Benzo[1,3]dioxol-5-yl-8-(3-hydroxy-propyl)-1,3-dioxa-8-aza-dicyclopenta[a,g]naphthalene-7,9-dione (29)

3-Amino-1-propanol (27 mg, 0.36 mmol) in toluene (5 mL) at 0° C. was added dropwise to a stirred solution of anhydride 1 (109 mg, 0.3 mmol) in toluene (40 mL). The mixture was stirred at room temperature for 1 h and then heated under Dean-Stark trap for 3 h. After water ceased to distill, the reaction mixture was cooled, washed successively with water (2×50 mL), 5% aqueous $NaHCO_3$ solution (2×50 mL), and water (2×50 mL), and then dried over $MgSO_4$. The solvent was removed in vacuo, and the resulting product was purified by column chromatography on silica gel using $CH_2Cl_2$/acetone (3:1 to 1:1, v/v) to provide 29 (10 mg, 11%) as a pale yellow powder. mp 150-152° C.; $^1$H NMR ($CDCl_3$) δ 8.27 (s, 1H, H4), 7.56 (d, 1H, H5, J=8.4 Hz), 7.26 (d, 1H, H6, J=8.4 Hz), 6.86-6.91 (m, 3H, H2'+H5'+H6'), 6.04 (s, 2H, 3',4'-$OCH_2O$—), 5.97 (s, 2H, 7,8-$OCH_2O$—), 3.69-3.76 (m, 4H, $NCH_2CH_2CH_2OH$), 1.83 (m, 2H, $NCH_2CH_2CH_2OH$).

9-Benzo[1,3]dioxol-5-yl-naphtho[1,2-d][1,3]dioxole-7,8-dicarboxylic acid dimethyl ester (30)

Compound 1 (108.6 mg, 0.3 mmol) was dissolved to a mixture of MeOH (4 mL) and THF (8 mL). Trimethylsilyldiazomethane (2 M in hexanes, 1.0 mL, 2.0 mmol) was added to the solution. The mixture was stirred for 12 h at room temperature, and then concentrated in vacuo. The residue was purified by chromatography on silica gel using n-hexane/EtOAc (2:1, v/v) to afford 30 (67 mg, 55%) as a pale yellow powder. mp 157-159° C.; $^1$H NMR ($CDCl_3$) δ 8.53 (s, 1H, H4), 7.58 (d, 1H, H5, J=8.7 Hz), 7.27 (d, 1H, H6, J=8.7 Hz), 6.79-6.82 (m, 3H, H2'+H5'+H6'), 6.03 (AB, 2H, 3',4'-$OCH_2O$—, Δδ=10.2 Hz, J=1.5 Hz), 5.89 (AB, 2H, 7,8-$OCH_2O$—, Δδ=7.2 Hz, J=1.5 Hz), 3.94, 3.66 (each s, 2×3H, 2×$OCH_3$); MS (EI) m/z 408 $[M]^+$.

9-Benzo[1,3]dioxol-5-yl-naphtho[1,2-d][1,3]dioxole-7,8-dicarboxylic acid 8-methyl ester (31)

Compound 30 (20 mg, 0.05 mmol) was refluxed with 1 M solution of KOH in MeOH (10 mL) for 2 h. The solution was cooled, and the solvent was removed under reduced pressure. The remaining solid was dissolved in water (10 mL) and then acidified to pH 1-2 with 10% aqueous HCl solution. The precipitate was collected by filtration, washed with water, and dried. The product was purified by column chromatography on silica gel using $CH_2Cl_2$/MeOH (20:1 to 10:1, v/v) to give 31 (11 mg, 56%) as a pale yellow powder. mp 273-275° C.; $^1$H NMR ($CDCl_3$) δ 8.54 (s, 1H, H4), 7.49 (d, 1H, H5, J=8.1 Hz), 7.20 (d, 1H, H6, J=8.1 Hz), 6.76-6.82 (m, 3H, H2'+H5'+H6'), 6.03 (AB, 2H, 3',4'-$OCH_2O$—, Δδ=11.1 Hz), 5.88 (AB, 2H, 7,8-$OCH_2O$—, Δδ=7.2 Hz), 3.62 (s, 3H, $OCH_3$); MS (FAB, positive) m/z 395 $[M+H]^+$.

9-Benzo[1,3]dioxol-5-yl-naphtho[1,2-d][1,3]dioxole-7,8-dicarboxylic acid (32)

Compound 30 (20 mg, 0.05 mmol) was refluxed with 1 M solution of KOH in MeOH (10 mL) for 24 h. Completion of the reaction, followed by the workup as described for the isolation of 31, gave a residue, which was purified by silica gel column chromatography. Elution with $CH_2Cl_2$/MeOH (2:1, v/v) as eluent yielded 32 (12 mg, 63%) as a yellow powder. mp 253° C. (decomp.); $^1$H NMR (DMSO-$d_6$) δ 8.25 (s, 1H, H4), 7.53 (d, 1H, H5, J=8.7 Hz), 7.24 (d, 1H, H6, J=8.7 Hz), 6.72-6.82 (m, 3H, H2'+H5'+H6'), 5.99 (AB, 2H, 3',4'-$OCH_2O$—, Δδ=18.9 Hz), 5.81 (AB, 2H, 7,8-$OCH_2O$—, Δδ=6.0 Hz); MS (FAB, positive) m/z 381 $[M+H]^+$.

9-Benzo[1,3]dioxol-5-yl-6-hydroxy-naphtho[1,2-d][1,3]dioxole-7,8-dicarboxylic acid diethyl ester (33)

Hydroxyacetal 1a (3.44 g, 10 mmol), diethyl acetylenedicarboxylate (1.70 g, 10 mmol), $CH_2Cl_2$ (4.5 mL), and glacial acetic acid (3 mL) were heated at 140° C. for 24 h. The cooled mixture was diluted with $CH_2Cl_2$ (100 mL), washed with 5% $NaHCO_3$ solution (3×100 mL), dried over $MgSO_4$, and concentrated under vacuum. The residue was chromatographed over silica gel using n-hexane/EtOAc/triethylamine (3:1:0.1, v/v/v), followed by crystallization from ether to afford 33 (741 mg, 16%) as a white powder. mp 192-194° C.; $^1H$ NMR ($CDCl_3$) δ 12.76 (s, 1H, 4OH), 8.15 (d, 1H, H5, J=8.7 Hz), 7.21 (d, 1H, H6, J=8.7 Hz), 6.77-6.81 (m, 3H, H2'+H5'+H6'), 6.01 (AB, 2H, 3',4'-$OCH_2O$—, Δδ=13.5 Hz, J=1.5 Hz), 5.86 (AB, 2H, 7,8-$OCH_2O$—, Δδ=5.7 Hz, J=1.5 Hz), 4.41, 4.01 (each q, 2×2H, 2×$OCH_2CH_3$, J=7.2 Hz), 1.37, 1.06 (each t, 2×3H, 2×$OCH_2CH_3$, J=7.2 Hz); MS (EI) m/z 452 $[M]^+$.

10-Benzo[1,3]dioxol-5-yl-6-hydroxy-7H-furo[3',4':6,7]naphtho[1,2-d][1,3]dioxol-9-one (34)

A solution of 33 (45.2 mg, 0.1 mmol) in THF (1 mL) was added dropwise to a suspension of lithium aluminum hydride (7.6 mg, 0.2 mmol) in THF (1 mL) at 0° C. The mixture was stirred at room temperature for 2 h and quenched with aqueous saturated $Na_2SO_4$ solution, and then extracted with $CHCl_3$ (2×30 mL). After evaporation of organic solvent, the residue was purified by column chromatography on silica gel using $CH_2Cl_2$/MeOH (20:1, v/v) to give 34 (36 mg, 99%) as a yellow powder. mp 257° C. (decomp.); $^1H$ NMR (DMSO-$d_6$) δ 10.67 (s, 1H, 4OH), 7.94 (d, 1H, H5, J=9.0 Hz), 7.44 (d, 1H, H6, J=9.0 Hz), 6.84 (d, 1H, H5', J=8.1 Hz), 6.79 (d, 1H, H2', J=1.5 Hz), 6.66 (dd, 1H, H6', J=1.5, 8.1 Hz), 6.04 (AB, 2H, 3',4'-$OCH_2O$—, Δδ=6.0 Hz, J=0.6 Hz), 5.88 (AB, 2H, 7,8-$OCH_2O$—, Δδ=6.3 Hz, J=0.9 Hz), 5.32 (s, 2H, lactone-$CH_2$—); MS (FAB, positive) m/z 365 $[M+H]^+$.

9-Benzo[1,3]dioxol-5-yl-6-methoxy-naphtho[1,2-d][1,3]dioxole-7,8-dicarboxylic acid diethyl ester (35)

Compound 33 (95 mg, 0.21 mmol) was dissolved in a mixture of MeOH (3 mL) and THF (6 mL). (Trimethylsilyl) diazomethane (2 M in hexanes, 0.6 mL, 1.2 mmol) was added to the solution. The mixture was stirred for 12 h at room temperature, and then concentrated in vacuo. The crude material was purified by column chromatography on silica gel using $CH_2Cl_2$ to afford 35 (97 mg, 99%) as a yellow oil. $^1H$ NMR ($CDCl_3$) δ 7.86 (d, 1H, H5, J=8.7 Hz), 7.26 (d, 1H, H6, J=8.7 Hz), 6.75-6.82 (m, 3H, H2'+H5'+H6'), 6.00 (AB, 2H, 3',4'-$OCH_2O$—, Δδ=11.7 Hz, J=1.2 Hz), 5.87 (AB, 2H, 7,8-$OCH_2O$—, Δδ=9.0 Hz, J=1.2 Hz), 4.39 (q, 2H, $OCH_2CH_3$, J=7.2 Hz), 4.06 (s, 3H, 4-$OCH_3$), 4.03 (q, 2H, $OCH_2CH_3$, J=7.2 Hz), 1.38, 1.04 (each t, 2×3H, 2×$OCH_2CH_3$, J=7.2 Hz); MS (EI) m/z 466 $[M]^+$.

9-Benzo[1,3]dioxol-5-yl-naphtho[1,2-d][1,3]dioxole-7,8-dicarboxylic acid diamide (36)

Compound 9 (72 mg, 0.2 mmol) was added to a mixture of concentrated ammonium hydroxide (2 mL) and THF (2 mL). The suspension was stirred at 40° C. for 72 h, and then concentrated in vacuo Silica gel column chromatography of the crude product using $CH_2Cl_2$/MeOH (4:1 to 1:1, v/v) provided 36 (23 mg, 30%) as a pale yellow powder. mp 298° C. (decomp.); $^1H$ NMR ($CD_3OD$) δ 8.18 (s, 1H, H4), 7.55 (d, 1H, H5, J=8.4 Hz), 7.21 (d, 1H, H6, J=8.4 Hz), 6.72-6.86 (m, 3H, H2'+H5'+H6'), 5.93 (AB, 2H, 3',4'-$OCH_2O$—, Δδ=13.2 Hz, J=0.9 Hz), 5.80 (AB, 2H, 7,8-$OCH_2O$—, Δδ=7.2 Hz, J=0.9 Hz); MS (FAB, positive), m/z 402 $[M+H+Na]^+$.

10-Benzo[1,3]dioxol-5-yl-5-chloro-9H-furo[3',4':6,7]naphtho[1,2-d][1,3]dioxol-7-one (37)

A stirred solution of 2 (104 mg, 0.3 mmol), N-chlorosuccinimide (80 mg, 0.6 mmol) and concentrated $H_2SO_4$ (10 μL) in THF (5 mL) was heated to reflux for 24 h, and then diluted with $CHCl_3$ (50 mL). The reaction mixture was washed with 10% aqueous $Na_2S_2O_3$ solution (50 mL) and water (2×50 mL), dried over $MgSO_4$, and concentrated in vacuo. The product was purified by column chromatography on silica gel eluting with $CHCl_3$ to afford 37 (56 mg, 49%) as a brown solid. mp 267° C. (decomp.); $^1H$ NMR ($CDCl_3$) δ 8.91 (s, 1H, H4), 7.47 (s, 1H, H6), 6.76-6.91 (m, 3H, H2'+H5'+H6'), 6.08 (AB, 2H, 3',4'-$OCH_2O$—, Δδ=8.7 Hz, J=1.5 Hz), 5.97 (AB, 2H, 7,8-$OCH_2O$—, Δδ=8.7 Hz, J=1.5 Hz), 5.22 (q, 2H, lactone-$CH_2$—, J=8.7 Hz); MS (EI) m/z 384 $[M+2]^+$, 382 $[M]^+$.

10-Benzo[1,3]dioxol-5-yl-5-bromo-9H-furo[3',4':6,7]naphtho[1,2-d][1,3]dioxol-7-one (38)

N-bromosuccinimide (10.7 mg, 0.06 mmol) and concentrated $H_2SO_4$ (5 μL) were added to a solution of 2 (15.4 mg, 0.044 mmol) in THF (1 mL). The solution was stirred at room temperature for 20 h, and then diluted with EtOAc (30 μL). The same workup and purification procedure as described for the isolation of 37 gave 38 (12 mg, 64%) as a pale yellow powder. mp 256° C. (decomp.); $^1H$ NMR ($CDCl_3$) δ 8.89 (s, 1H, H4), 7.65 (s, 1H, H6), 6.76-6.91 (m, 3H, H2'+H5'+H6'), 6.08 (AB, 2H, 3',4'-$OCH_2O$—, Δδ=8.7 Hz, J=1.5 Hz), 5.97 (AB, 2H, 7,8-$OCH_2O$—, Δδ=7.8 Hz, J=1.5 Hz), 5.22 (q, 2H, lactone-$CH_2$—, J=8.4 Hz); MS (EI) m/z 428 $[M+2]^+$, 426 $[M]^+$.

10-Benzo[1,3]dioxol-5-yl-5-iodo-9H-furo[3',4':6,7]naphtho[1,2-d][1,3]dioxol-7-one (39)

N-iodosuccinimide (13.6 mg, 0.06 mmol) and concentrated $H_2SO_4$ (5 μL) was added to a solution of 2 (14 mg, 0.04 mmol) in acetonitrile (1 mL). The mixture was stirred at room temperature for 36 h, concentrated at reduced pressure, and then diluted with ether (30 mL). The same workup and purification procedure as described for the isolation of 37 afforded 39 (10.5 mg, 55%) as a yellow powder. mp 255° C. (decomp.); $^1H$ NMR ($CDCl_3$) δ 8.78 (s, 1H, H4), 7.93 (s, 1H, H6), 6.75-6.90 (m, 3H, H2'+H5'+H6'), 6.08 (AB, 2H, 3',4'-$OCH_2O$—, Δδ=8.7 Hz, J=1.5 Hz), 5.97 (AB, 2H, 7,8-$OCH_2O$—, Δδ=7.8 Hz, J=1.5 Hz), 5.23 (q, 2H, lactone-$CH_2$—, J=8.7 Hz); MS (EI) m/z 474 $[M]^+$.

10-Benzo[1,3]dioxol-5-yl-5-bromo-8,9-dihydro-1,3-dioxa-8-aza-dicyclopenta[a,g]naphthalen-7-one (40)

N-bromosuccinimide (11 mg, 0.06 mmol) and concentrated $H_2SO_4$ (10 μL) was added to a solution of 18 (14 mg, 0.04 mmol) in THF (5 mL). The solution was stirred at room temperature for 24 h, and then diluted with EtOAc (30 mL). Completion of the reaction, followed by the workup as described for the isolation of 37, gave a residue, which was purified by silica gel column chromatography. Elution with $CH_2Cl_2$/acetone (10:1 to 5:1, v/v) as eluent yielded 40 (12 mg, 70%) as a pale brown solid. mp 285° C. (decomp.); $^1H$ NMR ($CDCl_3$) δ 8.81 (s, 1H, H4), 7.63 (s, 1H, H6), 6.77-6.91 (m, 3H, H2'+H5'+H6'), 6.07 (AB, 2H, 3',4'-$OCH_2O$—, Δδ=7.5 Hz, J=1.2 Hz), 5.93 (AB, 2H, 7,8-$OCH_2O$—, Δδ=6.0 Hz, J=1.2 Hz), 4.34 (m, 2H, lactam-$CH_2$—); MS (FAB, positive) m/z 428 $[M+2]^+$, 426 $[M]^+$.

11-Benzo[1,3]dioxol-5-yl-5-chloro-8,9-dihydro-1,3-dioxa-8,9-diaza-cyclopenta[a]anthracene-7,10-dione (41)

N-chlorosuccinimide (28 mg, 0.21 mmol) and concentrated $H_2SO_4$ (10 μL) was added to a solution of 28 (39.5 mg, 0.11 mmol) in THF (1 mL). The solution was stirred at room temperature for 48 h, and then diluted with EtOAc (30 mL). Completion of the reaction, followed by the workup as described for the isolation of 37, gave a residue, which was purified by silica gel column chromatography. Elution with $CH_2Cl_2$/acetone (10:1, v/v) as eluent afforded 41 (15.6 mg, 35%) as a yellow powder. mp 316° C. (decomp.); $^1$H NMR (DMSO-$d_6$) δ 12.58 (s, 1H, NH), 9.10 (s, 1H, NH), 8.01 (s, 1H, H4), 7.73 (s, 1H, H6), 7.04 (d, 1H, H5', J=7.8 Hz), 7.03 (d, 1H, H2', J=1.5 Hz), 6.86 (dd, 1H, H6', J=1.5, 7.8 Hz), 6.14 (AB, 2H, 3',4'-$OCH_2O$—, Δδ=23.1 Hz), 6.05 (AB, 2H, 7,8-$OCH_2O$—, Δδ=12.2 Hz); MS (EI) m/z 396 $[M-NH_2+2]^+$, 394 $[M-NH_2]^+$.

11-Benzo[1,3]dioxol-5-yl-5-bromo-8,9-dihydro-[1,3]dioxa-8,9-diaza-cyclopenta[a]anthracene-7,10-dione (42)

N-bromosuccinimide (9.4 mg, 0.053 mmol) and concentrated $H_2SO_4$ (5 μL) were added to a solution of 28 (13 mg, 0.035 mmol) in THF (1 mL). The solution was stirred at room temperature for 48 h, and then diluted with EtOAc (20 mL). The same workup and purification procedure as described for the isolation of 41 gave 42 (9 mg, 57%) as a yellow powder. mp 310° C. (decomp.); $^1$H NMR (DMSO-$d_6$) δ 12.54 (s, 1H, NH), 9.04 (s, 1H, NH), 8.13 (s, 1H, H4); 7.69 (s, 1H, H6), 7.00 (d, 1H, H5', J=7.8 Hz), 6.99 (d, 1H, H2', J=1.5 Hz), 6.82 (dd, 1H, H6', J=1.5, 7.8 Hz), 6.11 (AB, 2H, 3',4'-$OCH_2O$—, Δδ=17.4 Hz, J=0.6 Hz), 6.02 (AB, 2H, 7,8-$OCH_2O$—, Δδ=9.3 Hz, J=0.9 Hz); MS (FAB, positive) m/z 441 $[M-NH_2+H+2]^+$, 439 $[M-NH_2+H]^+$.

11-Benzo[1,3]dioxol-5-yl-5-iodo-8,9-dihydro-1,3-dioxa-8,9-diaza-cyclopenta[a]anthracene-7,10-dione (43)

N-iodosuccinimide (11.9 mg, 0.053 mmol) and concentrated $H_2SO_4$ (5 μL) were added to a solution of 28 (13.3 mg, 0.035 mmol) in acetonitrile (1 mL). The solution was stirred at room temperature for 48 h, and then diluted with EtOAc (20 mL). The same workup and purification procedure as described for the isolation of 41 yielded 43 (9 mg, 51%) as a brown solid. mp 300° C. (decomp.); $^1$H NMR (DMSO-$d_6$) δ 12.59 (s, 1H, NH), 9.10 (s, 1H, NH), 8.38 (s, 1H, H4), 7.79 (s, 1H, H6), 7.10 (d, 1H, H5', J=7.8 Hz), 7.09 (d, 1H, H2', J=1.7 Hz), 6.92 (dd, 1H, H6', J=1.7, 7.8 Hz), 6.22 (AB, 2H, 3',4'-$OCH_2O$—, Δδ=22.8 Hz, J=0.7 Hz), 6.10 (AB, 2H, 7,8-$OCH_2O$—, Δδ=13.5 Hz, J=0.9 Hz); MS (EI) m/z 486 $[M-NH_2]^+$.

9-Benzo[1,3]dioxol-5-yl-5-chloro-8-hydroxymethyl-naphtho[1,2-d][1,3]dioxole-7-carboxylic acid monosodium salt (44)

1 N aqueous NaOH solution (1.56 mL) was added to the solution of 37 (57 mg, 0.15 mmol) in MeOH (25 mL). The mixture was stirred at 70° C. for 1 h. The solvent was evaporated to give a crude product, which was purified by silica gel column chromatography using $CH_2Cl_2$/MeOH (3:1, v/v) to afford 44 (55 mg, 87%) as a white powder. mp 220° C. (decomp.); $^1$H NMR (DMSO-$d_6$) δ 8.39 (s, 1H, H4), 7.54 (s, 1H, H6), 6.89 (d, 1H, H5', J=8.7 Hz), 6.73 (d, 1H, H2', J=1.5 Hz), 6.63 (dd, 1H, H6', J=1.5, 8.7 Hz), 6.05 (AB, 2H, 3',4'-$OCH_2O$—, Δδ=18.9 Hz), 5.81 (AB, 2H, 7,8-$OCH_2O$—, A5=8.1 Hz), 4.12 (s, 2H, 2-$CH_2OH$); MS (FAB, positive) m/z 425 $[M+H+2]^+$, 423 $[M+H]^+$.

9-Benzo[1,3]dioxol-5-yl-5-bromo-8-hydroxymethyl-naphtho[1,2-d][1.3]dioxole-7-carboxylic acid monosodium salt (45)

Conversion of 38 (65 mg, 0.15 mmol) to 45 was accomplished using a procedure similar to that described for 44. The residue obtained was purified by silica gel column chromatography using $CH_2Cl_2$/MeOH (3:1, v/v) to provide 45 (64 mg, 91%) as a yellow powder. mp 205° C. (decomp.); $^1$H NMR (DMSO-$d_6$) δ 8.29 (s, 1H, H4), 7.69 (s, 1H, H6), 6.88 (d, 1H, H5', J=7.8 Hz), 6.72 (d, 1H, H2', J=1.5 Hz), 6.62 (dd, 1H, H6', J=1.5, 7.8 Hz), 6.05 (AB, 2H, 3',4'-$OCH_2O$—, Δδ=18.6 Hz), 5.81 (AB, 2H, 7,8-$OCH_2O$—, Δδ=8.4 Hz), 4.13 (s, 2H, 2-$CH_2OH$); MS (FAB, positive) m/z 469 $[M+H+2]^+$, 467 $[M+H]^+$.

9-Benzo[1,3]dioxol-5-yl-8-hydroxymethyl-5-iodo-naphtho[1,2-d][1,3]dioxole-7-carboxylic acid monosodium salt (46)

Conversion of 39 (64 mg, 0.135 mmol) to 46 was accomplished using a procedure similar to that described for 44. The residue obtained was purified by silica gel column chromatography using $CH_2Cl_2$/MeOH (3:1, v/v) to give 46 (62 mg, 89%) as a pale yellow powder. mp 212° C. (decomp.); $^1$H NMR (DMSO-$d_6$) δ 8.27 (s, 1H, H4), 7.86 (s, 1H, H6), 6.88 (d, 1H, H5', J=7.8 Hz), 6.71 (d, 1H, H2', J=1.2 Hz), 6.62 (dd, 1H, H6', J=1.2, 7.8 Hz), 6.04 (AB, 2H, 3',4'-$OCH_2O$—, Δδ=18.3 Hz), 5.79 (AB, 2H, 7,8-$OCH_2O$—, Δδ=8.4 Hz), 4.13 (s, 2H, 2-$CH_2OH$); MS (FAB, positive) m/z 515 $[M+H]^+$.

Antiviral Effects

Experimental

In Vitro Antiviral Assays

The antiviral assays for HBV, (Doong et al., 1991, *Proc. Natl. Acad. Sci. U.S.A.* 88:8495-8499) HSV-1, (Bastow et al., 1983, *Antimicrob. Agents Chemother.* 23: 914-917) HSV-2, (Bastow et al., 1983, *Antimicrob. Agents Chemother.* 23:914-917) EBV, (Yao et al., 1993, *Antimicrob. Agents Chemother.* 37:1420-1425), CMV (Andreoni et al., 2002, *J. Med. Virol.* 67:33-40) and HIV (Mellors et al., 1992, *Mol. Pharmacol.* 41: 446-451) were performed according to the previously reported procedures. Anti-HCV activities were tested in Huh-Luc/neo cell line. Cells were seeded into 48-well plates and grown until confluent. Different concentrations of drugs were added into media (DMEM, 10% dFBS) and incubated for 3 days. At the end of 3-day treatment, medium were removed and 50 μl of Passive lysis buffer (Promega) were added. Cell lysate was shaken at room temperature for 15 min. 30 μl/well of cell lysate was transferred to another 96-well plate, 100 μl/well of luciferase activity assay substrate was added into plate and read by a luminometer (Amersham) immediately.

Southern blot hybridization was used to measure the effects of compounds on HBV DNA. Total DNA from cells was extracted using Dneasy Tissue kit (Qiagen Inc. Valencia, Calif.) and separated on a 0.8% agarose gel. Separated DNA was transferred to a Hybond-N+membrane (Amersham Pharmacia Biotech Inc. Piscataway, N.J.). Inhibition of viral DNA replication was assessed by comparison of the replicative HBV DNA from drug-treated versus untreated cultures using hybridization of the membrane with a [α-$^{32}$P] dCTP labeled whole HBV DNA probe followed by autoradiography. Quantitative densitometry was performed on a Molecular Dynamics Densitometer (Amersham Pharmacia Biotech Inc. Piscataway, N.J.) using ImageQuaNT image analysis software. The integrated HBV genome was used as the internal control to normalize the amount of DNA loaded. Northern blot hybridization was used to measure the effects of the compounds on HBV RNA. Total intracellular RNA was extracted from cells using Rneasy kit (Qiagen Inc. Valencia, Calif.). RNA was separated in a 1.2% formaldehyde agarose gel and transferred to a Hybond-N+ membrane (Amersham Pharmacia Biotech Inc. Piscataway, N.J.). The membrane was hybridized with the same probe mentioned above at 65° C. followed by autoradiography. GAPDH RNA level was used as an internal control to normalize the amount of RNA loaded. The decrease of HBV core protein expression was assessed by western blot. A cellular crude extract of HepG2.2.12 cells was separated on a 12% SDS-PAGE gel and transferred onto a nitrocellulose membrane (Bio-rad Laboratories, Hercules, Calif.). Anti-HBV core antibody (DAKO Corp. Carpinteria, Calif.) and anti rabbit IgG secondary antibody (Sigma. St. Louis, Mo.) were added. Actin protein level was used as the internal control.

Cell Culture

Hep.G2.2.15 is a hepatoblastoma cell line stably transfected with a HBV genome (ayw strain) (Sells et al., 1987, *Proc Natl Acad Sci USA.* 84 (4):1005-1009). W10, a HepG2 cell line, was transfected with an adr HBV strain (Fu et al., 2000, *Antimicrob Agents Chemother* 44 (12): 3402-3407; Fu et al., 1999, *Biochem Pharmacol.* 57 (12): 1351-1359). These cell lines were used to assess the antiviral activity of helioxanthin and 22. Various concentrations of the drugs in minimal essential medium with Earle's salts (MEME) containing 10% fetal bovine serum (FBS) were tested in 6-day-old cultures. The drugs were left in the culture medium for 3 days, then the medium was removed and fresh medium containing the same concentration of the drugs was added. At the end of another 3-day period, the culture medium and cells were harvested to measure the HBV replication level. The Lamivudine resistant cell line DM2 (Fu et al., 2000, *Antimicrob Agents Chemother* 44 (12): 3402-3407) is also a hepatoblastoma cell line stably transfected with HBV genome (adr strain) which contains the L526M/M550V double mutation. The culture conditions of DM2 are the same as that of HepG.2.2.15.

Cell Cytotoxicity Assays

Cytotoxicities of test compounds on MT-2 (Mellors et al., 1992 *Mol. Pharmacol.* 41:446-451) and CEM (Grove et al., 1995, *Cancer Res.* 55:3008-3011) cells were determined according to the previously reported procedures. Hepg2 cells were seeded at a density of $10^4$ cells/ml/well in 24-well plates and cultured in MEME supplemented with 10% FBS at 37° C. and 5% $CO_2$. Each test compound at different concentrations was added on the second day of the culture and the cells were incubated for another 3 days. At the end of the incubation period, the medium was removed and 0.5 ml of 0.5% methylene blue in 50% ethanol (v/v) was added to each well and set at room temperature for 30-60 minutes. The methylene blue was removed; the plates were washed with water and allowed to air dry. Once dry, 1% sarcosyl was added to dissolve the stained cell layer. The absorbance at 595 nm was measured with a microplate reader (Molecular Devices Corp. Sunnyvale, Calif.). The cytotoxicity to CEM cell was calculated as described previously (Grove et al., 1995, *Cancer Res.* 55 (14): 3008-3011).

Effect of Helioxanthin and 22 on the wt HBV Cell Line W10 and Lamivudine Resistant Cell Line DM2

Quantitative real-time PCR was used to determine the extracellular HBV copy number in the medium of DM2 cells with and without drug treatment. The protocol for drug treatment was the same as the above description except that the cells were seeded onto a 96-well plate. After a 6-day treatment, 100 μl of medium per sample was transferred to thin-wall 96-well PCR plates. 8 μl of 2.2 mg/ml Pronase (Sigma. St. Louis, Mo.) was added into the medium and was incubated at 37° C. for 1.5 hours. 1 unit of Dnase I (Roche Applied Science. Indianapolis, Ind.) was added per well for an additional hour at 37° C. After incubating the medium at 95° for 5 min, 3 μl of the sample was added into a 50 μl real-time PCR reaction. The sequence of primers and probe used in the real-time PCR was as follows: Sense primer 5'-attcctatgggagtgggc-3'; Anti sense primer 5'-gaggtaaaaagggactcaag-3'; Probe 5' ctgccatttgttcagtggttcgggcag-3' (Cy5 labeled). The components of the 50 μl PCR reaction were 25 μl of SuperMix UDG (Invitrogen life technologies. Carlsbad, Calif.), 300 nM of sense and anti sense primers, 100 nM of probe (Biosearch technologies, Inc. Novato, Calif.) and $H_2O$. The PCR was performed using iCycler (Bio-rad Laboratories, Hercules, Calif.) according to the following protocol: 50° C. for 2 min, 95° C. for 8.5 min, 40 cycles of 95° C. for 15 sec and 56° C. for 1 min. Quantification of the copy number was determined by comparing the sample amount to a standard curve generated in each run. Sample amounts were normalized using β-actin as the internal control.

Results and Discussion

In Vitro Studies

The results of the in vitro studies are summarized in Table 1.

TABLE 1

Antiviral Activities of Helioxanthin and its Analogues

| Compd | Antiviral Activities ($EC_{50}$, μM) | | | | | | | Cytotoxity ($ID_{50}$, μM) | |
|---|---|---|---|---|---|---|---|---|---|
| | HBV | HCV[a] | HSV-1 | HSV-2 | EBV | CMV | HIV[b] | MT-2 | CEM |
| 1 | >10 | >10 | >50 | >50 | >20 | 17.6 | >100 | >100 | >50 |
| 2 | 1.0 | 3(64) | 2 | 35 | >20 | 7.3 | >2.5(T) | 2.5 | 31 |
| 3 | 3.4 | 10(25) | 9 | 25 | >20 | 2.5 | >10(T) | 10 | 30 |
| 4 | >10 | 10(71) | >50 | >50 | >20 | — | >100 | >100 | >50 |
| 5 | >10 | >10 | >25 | >25 | >20 | — | >48(T) | 48 | >50 |
| 6 | >10 | 10(55) | >50 | >50 | >20 | — | >100 | >100 | >50 |
| 7 | >23 | >10 | >25 | >25 | >15 | — | >10(T) | 10 | 46 |
| 8 | >10 | >10 | >25 | >25 | >15 | 3.7 | >100 | >100 | 10 |

TABLE 1-continued

| Antiviral Activities of Helioxanthin and its Analogues | | | | | | | | | |
|---|---|---|---|---|---|---|---|---|---|
| | Antiviral Activities ($EC_{50}$, μM) | | | | | | | Cytotoxicity ($ID_{50}$, μM) | |
| Compd | HBV | HCV[a] | HSV-1 | HSV-2 | EBV | CMV | HIV[b] | MT-2 | CEM |
| 9[d] | — | — | — | — | — | — | — | N-D | N-D |
| 10 | >10 | 10(62) | >50 | >50 | >5 | — | >100 | >100 | >100 |
| 11[d] | — | — | — | — | — | — | — | N-D | N-D |
| 12 | 0.8 | 3(58) | 0.15 | <0.1 | 9 | 0.45 | >5(T) | 5 | 8.4 |
| 13 | >20 | >10 | 12 | >25 | >20 | — | >26(T) | 26 | 29 |
| 14 | >10 | >10 | >50 | >50 | >20 | — | >70(T) | 70 | 76 |
| 15 | 0.8 | 3(64) | 0.8 | >3 | >20 | — | >10(T) | 10 | 3 |
| 16 | >10 | >10 | >50 | >50 | >20 | — | >100 | >100 | 90 |
| 17 | >10 | 3(29) | 14 | 14 | >20 | — | >26(T) | 26 | 27 |
| 18 | 0.08 | 1(55) | 0.29 | 0.16 | 11 | — | >4(T) | 4 | 4.5 |
| 19 | 1.6 | >3 | 0.67 | 1 | >20 | — | >8(T) | 8 | 6 |
| 20 | >20 | 10(85) | 13 | >20 | >20 | — | >28(T) | 28 | 67 |
| 21 | >20 | 10(58) | 5 | 7 | >20 | — | 5 | 22 | 22 |
| 22 | 0.9 | 3(80) | 0.6 | 0.5 | >20 | — | >16(T) | 16 | 5 |
| 23 | >10 | >10 | >50 | >50 | >20 | — | >100 | >100 | >100 |
| 24 | >5 | >10 | >30 | >30 | >5 | 4.1 | >16(T) | 16 | 17 |
| 25 | >10 | >10 | >40 | >40 | >20 | — | >100 | >100 | 93 |
| 26 | 1 | >10 | 5 | 10 | 13 | — | >7(T) | 7 | 40 |
| 27 | >20 | 10(25) | 17 | 40 | >20 | — | >25(T) | 25 | 32 |
| 28 | 0.03 | 10(74) | 1.4 | 1.4 | >25 | — | 15(T) | 16 | 50 |
| 29 | >5 | >10 | >30 | >30 | >5 | 8.1 | >22(T) | 22 | 27 |
| 30 | >20 | 10(93) | >50 | >50 | >20 | — | >28(T) | 28 | 50 |
| 31 | >20 | >10 | >50 | >50 | >20 | — | >90(T) | 90 | 74 |
| 32 | >20 | >10 | >50 | >50 | >20 | — | >100 | >100 | >100 |
| 33 | >10 | 10(62) | >50 | >50 | >10 | — | >15(T) | 15 | 39 |
| 34 | >10 | >10 | 23 | 28 | >10 | — | >13(T) | 13 | 31 |
| 35 | >20 | 10(60) | >50 | >50 | >20 | — | >24(T) | 24 | >100 |
| 36 | >20 | >10 | >50 | >50 | >20 | — | >100 | >100 | >100 |
| 37 | >10 | >10 | 23 | >25 | >20 | 8.8 | >50(T) | 50 | 27 |
| 38 | >60 | >10 | >50 | >50 | >15 | — | >100 | >100 | 100 |
| 39 | >40 | >10 | >25 | >25 | >10 | — | >80(T) | 80 | 70 |
| 40 | >20 | 10(32) | 6.5 | >20 | >20 | — | >54(T) | 54 | 38 |
| 41 | >10 | 10(60) | 7 | >40 | >20 | — | >30(T) | 30 | >100 |
| 42 | >20 | 3(45) | 16 | >20 | >20 | — | 6 | >100 | 28 |
| 43 | >10 | 10(52) | >40 | >40 | >20 | — | 2 | 35 | 40 |
| 44 | >10 | >10 | >50 | >50 | >20 | >20 | >60(T) | 60 | >100 |
| 45 | >10 | — | >50 | >50 | >20 | >20 | >50(T) | 50 | 46.5 |
| 46 | >18 | 10(36) | >50 | >50 | >20 | >20 | >80(T) | 80 | >100 |
| ACV | — | — | 8 | 21 | — | — | — | N-D | N-D |
| 3TC | 0.02 | — | — | — | 0.4 | — | — | N-D | N-D |
| ddC | — | — | — | — | — | — | 0.8 | 70 | 5 |
| Interferon | — | 10 u/ml (90) | — | — | — | — | — | N-D | N-D |

[a]The values in the parentheses mean the percent of inhibition.
[b](T) means toxic
[d]low solubility.

The lactam 18 and the cyclic hydrazide 28 derivatives of helioxanthin (2) exhibited significant in vitro anti-HBV activities ($EC_{50}$=0.08 and 0.03 μM, respectively), and compound 18 showed the most potent anti-HCV activity (55% inhibition at 1.0 M). Compound 12, the acid-hydrolyzed product of the cyclic imide 9, was more active than helioxanthin against HBV ($EC_{50}$=0.8 μM). Compounds 15 and 22 containing dimethoxy moieties instead of methylenedioxy groups in the C ring of compounds 12 and 18 displayed potent antiviral activities against HCV (64 and 80% inhibition at 3.0 μM, respectively) as well as HBV ($EC_{50}$=0.8 and 0.9 μM, respectively). The most potent anti-HSV compounds were 12 and 18, which showed marked inhibition of HSV-1 ($EC_{50}$=0.15 and 0.29 μM, respectively) and HSV-2 ($EC_{50}$<0.1 and 0.16 μM, respectively). Compound 12 was found to exhibit broad-spectrum antiviral activity against HSV-1 ($EC_{50}$=0.15 μM), HSV-2 ($EC_{50}$<0.1 μM), EBV ($EC_{50}$=9.0 μM), and CMV ($EC_{50}$=0.45 μM). It was about 140 and 210 times more potent than the reference drug acylclovir ($EC_{50}$=21 μM) against HSV-1 and HSV-2, respectively. The cyclic hydrazide 28 and its brominated product 42 showed moderately potent anti-HIV activities ($EC_{50}$=2.7 and 2.5 μM, respectively).

Compound 12, the acid-hydrolyzed product of cyclic imide 9, exhibited potent antiviral activities against HBV and CMV as well as HSV. The reduction of imide 9 yielded a lactam 18 and a retro-lactam 16. The lactam 18 was more potent than compound 12 against HBV and HCV, and as potent as compound 12 against HSV. In contrast, the retro-lactam 16 was not active at all. This finding indicated that the "up" carbonyl group of the lactam 18 is an important feature for the antiviral activity.

The cyclic hydrazide 28 showed the most potent anti-HBV activity among the tested helioxanthin analogues. In addition, compound 28 exhibited moderately potent activity against HIV.

Anti-HBV Effects of Helioxanthin and 22

The effect of helioxanthin and 22 on HBV DNA in HepG2.2.15 cells, which is stably transfected with the HBV genome, was assessed. Structures of helioxanthin and 22 are shown in FIG. 6. The cells were treated with various concentration of the drugs for 6 days. The results of HBV DNA inhibition are shovel in FIG. 2. The level of HBV replicative intermediates in cells was estimated from the ratio of the HBV replicative intermediates to the integrated HBV genome. Antiviral effects are shown as a percentage of untreated control values. The $EC_{50}$ of helioxanthin and 22 were approximately 1 and 0.08 μM respectively (see Table 2).

TABLE 2

The $EC_{50}$ and $IC_{50}$ helioxanthin, 22, and lamivudine for different HBV strains.

| | $EC_{50}$ (μM) | | | $IC_{50}$ (μM) | |
|---|---|---|---|---|---|
| Compound | wt[a] (adr)[b] | L526M/M550V (adr)[c] | wt (ayw)[d] | CEM | HepG2 |
| Helioxanthin | 0.4 ± 0.1 | 0.1 ± 0.2 | 1 ± 0.2 | 32 ± 1.4 | 6 ± 1.2 |
| 22 | 0.004 ± 0.002 | 0.0003 ± 0.0001 | 0.08 ± 0.01 | 3.6 ± 1.2 | 2 ± 0.3 |
| Lamivudine | 0.02 ± 0.03 | >3 | 0.05 ± 0.03 | >100 | >100 |

[a]wild type.

[b]Anti-HBV activity tested in W10 cells.

[c]Anti-HBV activity tested in DM2 cells.

[d]Anti-HBV activity tested in HepG2 cells.

The results showed that helioxanthin and its derivative had very potent anti-HBV effects.

Cytotoxicity

The concentrations of helioxanthin and 22 that inhibited 50% of cell growth ($IC_{50}$) were 6 μM and 2 μM respectively (Table 2). However in CEM cells, helioxanthin was less toxic, with the $IC_{50}$ of 32 μM. The cytotoxicity of 22 was similar for HepG2 and CEM cells.

Lamivudine-Resistant HBV is Susceptible to Helioxanthin

W10 and DM2 cells (Fu et al., 2000, *Antimicrob Agents Chemother* 44 (12): 3402-3407), were used to evaluate the effects of these two compounds on wt HBV (adr strain) and its lamivudine-resistant HBV. W10 is a HepG2 cell line stably transfected with a wild type (wt) adr strain of HBV genome, the most common one in Asia. DM2 is a HepG2 cell line stably transfected with the HBV adr strain containing the L526M/M550V double mutation in the DNA polymerase region. These two cell lines were treated with different concentrations of helioxanthin and 22. After a 6-day treatment, the amount of HBV DNA, which was secreted into the medium, was evaluated using real-time PCR (FIG. 3). Cells were also treated with lamivudine, which served as the control. The real-time PCR method was validated by comparing the results of intracellular HBV DNA levels obtained from the Southern blot hybridization analysis to the results from real-time PCR that measured HBV DNA copies in the HepG2.2.15 medium with or without treatment of lamivudine. The $EC_{50}$ values estimated by both methods were consistent. Interestingly, helioxanthin and 22, especially 22, were more inhibitory against the lamivudine-resistant HBV than the wt strain. The $EC_{50}$ of helioxanthin against wt adr and L526M/M550V HBV were 0.4 μM and 0.1 μM respectively, while the $EC_{50}$ of 22 against wt adr and adr L526M/M550V HBV were 0.004 μM and 0.0003 μM respectively.

Helioxanthin and 22 Decreased HBV mRNA

Since helioxanthin and its derivatives are a unique class of chemical with anti-HBV activity, the mechanism of HBV inhibition was examined by first assessing their impact on HBV mRNA. The HepG2.2.15 cells treated with these two drugs for 6 days, then a Northern blot analysis on the total cellular RNA was performed with a HBV specific [$\alpha$-$^{32}$P] dCTP labeled probe. FIG. 4 shows the result from cells with helioxanthin and 22 treatments. Both compounds decreased 3.5 kb, 2.4/2.1 kb HBV transcripts in a dose-dependent manner, with $EC_{50}$ for the 3.5 kb transcript being 0.09 μM and 1 μM respectively. Lamivudine had no effect on HBV RNA level.

Helioxanthin and 22 Inhibited HBV Viral Protein Expression in HepG2.2.15 Cells

Since 3.5 kb HBV transcript was decreased after drug treatment, it was anticipated that this class of compounds would also affect viral protein expression. HepG2.2.15 cells were treated with helioxanthin and 22 for 6 days. Western blot analysis was performed using anti HBV core protein antibody to see if the drugs would suppress core protein expression in the cells. As depicted in FIG. 5, the core protein expression decreased in a dose-dependent manner. Lamivudine had no effect on HBV core protein expression.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. An isolated compound of the formula:

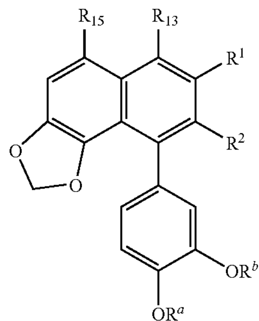

Where $R^1$ and $R^2$ together with the adjacent benzene ring form a 6-membered heterocyclic ring according to the structure Ia:

$$\text{Ia: ring containing } X^1, Y, X^2$$

where Y is a —N($R^7$)—N($R^8$)— group;

$X^1$ and $X^2$ are each a C═O group;

$R^7$ and $R^8$ are each independently H or a $C_1$-$C_6$ alkyl group which may be optionally substituted with a hydroxyl group;

$R^a$ and $R^b$ together form a —$(CH_2)_k$— group;

k is 1 or 2;

$R_{13}$ is H, OH, —O($C_1$-$C_4$)alkyl, ($C_1$-$C_4$) alkyl; and $R_{15}$ is H, OH, —O($C_1$-$C_4$)alkyl, ($C_1$-$C_4$) alkyl, F, Cl, Br or I;

or their anomers or pharmaceutically acceptable salts thereof.

2. The composition according to claim 1 wherein $R_7$ and $R_8$ are independently H or $CH_3$.

3. The compound according to claim 1 wherein $R_7$ is H.

4. The compound according to claim 2 wherein $R_7$ is H.

5. The compound according to claim 1 wherein $R_8$ is H.

6. The compound according to claim 2 wherein $R_8$ is H.

7. The compound according to claim 1 wherein $R_7$ and $R_8$ are H.

8. The compound according to claim 1 wherein $R^{13}$ is H.

9. The compound according to claim 2 wherein $R^{13}$ is H.

10. The compound according to claim 3 wherein $R^{13}$ is H.

11. The compound according to claim 4 wherein $R^{13}$ is H.

12. The compound according to claim 1 wherein $R^{15}$ is H, F, Cl, Br or I.

13. The compound according to claim 2 wherein $R^{15}$ is H, F, Cl, Br or I.

14. The compound according to claim 3 wherein $R^{15}$ is H, F, Cl, Br or I.

15. The compound according to claim 7 wherein $R^{15}$ is H, F, Cl, Br or I.

16. The compound according to claim 8 wherein $R^{15}$ is H or Br.

17. The compound according to claim 9 wherein $R^{15}$ is H or Br.

18. The compound according to claim 1 wherein $R^{15}$ is H or Br.

19. The compound according to claim 1 wherein $R^{15}$ is H.

20. The compound according to claim 2 wherein $R^{15}$ is H.

21. The compound according to claim 9 wherein $R^{15}$ is H.

22. A compound according to claim 1 which is:

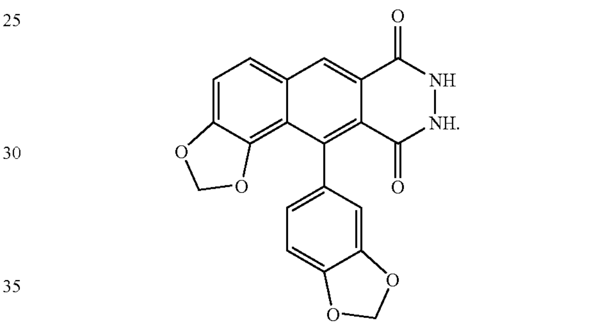

23. A pharmaceutical composition comprising an effective amount of a compound according to any of claims 1-22 in combination with a pharmaceutically acceptable additive, carrier or excipient.

24. The composition according to claim 23 further comprising an additional antiviral agent.

25. The composition according to claim 24 wherein said additional antiviral agent is selected from the group consisting of AZT, ddC, ddI, d4T, 3TC, delvaridine, nevirapine, and efravirenz saquinavir, ritonavir, indinavir, nelfinavir, amprenivir and mixtures thereof.

* * * * *